United States Patent
Chen et al.

(10) Patent No.: US 10,246,719 B2
(45) Date of Patent: Apr. 2, 2019

(54) MODULATING LACCASE ENZYME TO REGULATE CELL WALL BIOSYNTHESIS AND RECALCITRANCE IN PLANTS

(71) Applicant: UT-Battelle, LLC, Oak Ridge, TN (US)

(72) Inventors: Jin-Gui Chen, Oak Ridge, TN (US); Lee E. Gunter, Oak Ridge, TN (US); Sara S. Jawdy, Oak Ridge, TN (US); Xiaohan Yang, Knoxville, TN (US); Gerald A. Tuskan, Oak Ridge, TN (US); Anthony Christian Bryan, Oak Ridge, TN (US)

(73) Assignee: UT-BATTELLE, LLC, Oak Ridge, TN (US)

(*) Notice: Subject to any disclaimer, the term of this patent is extended or adjusted under 35 U.S.C. 154(b) by 0 days.

(21) Appl. No.: 15/647,819

(22) Filed: Jul. 12, 2017

(65) Prior Publication Data

US 2018/0016592 A1  Jan. 18, 2018

Related U.S. Application Data

(60) Provisional application No. 62/361,541, filed on Jul. 13, 2016.

(51) Int. Cl.
| | | |
|---|---|---|
| *C12N 15/82* | (2006.01) | |
| *C07K 14/415* | (2006.01) | |
| *C12N 5/04* | (2006.01) | |
| *C12N 15/52* | (2006.01) | |
| *C12Q 1/68* | (2018.01) | |
| *C12N 9/02* | (2006.01) | |
| *C12Q 1/6895* | (2018.01) | |
| *A01H 1/00* | (2006.01) | |
| *A01H 5/00* | (2018.01) | |

(52) U.S. Cl.
CPC ........ *C12N 15/8255* (2013.01); *C07K 14/415* (2013.01); *C12N 5/04* (2013.01); *C12N 9/0061* (2013.01); *C12N 15/52* (2013.01); *C12N 15/8213* (2013.01); *C12N 15/8218* (2013.01); *C12Q 1/68* (2013.01); *C12Q 1/6895* (2013.01); *A01H 1/00* (2013.01); *A01H 5/00* (2013.01); *C12Q 2600/13* (2013.01)

(58) Field of Classification Search
None
See application file for complete search history.

(56) References Cited

PUBLICATIONS

Lu et al 2013 PNAS 110:10848-10853 (Year: 2013).*
Wang et al 2015 Biotechnol Biofuels 8:1-11 (Year: 2015).*
Ranocha et al., "Laccase down-regulation causes alterations in phenolic metabolism and cell wall structure in poplar", Plant Physiology, May 2002, vol. 129, pp. 145-155.
Biswal et al., "Downregulation of GAUT12 in Populus deltoides by RNA silencing results in reduced recalcitrance, increased growth and reduced xylan and pectin in a woody biofuel feedstock", Biotechnology for Biofuels, 2015, vol. 8, No. 41, pp. 1-25.
Zhao et al., "Laccase is necessary and nonredundant with Peroxidase for lignin polymerization during vascular development in *Arabidopsis*", The Plant Cell, Oct. 2013, vol. 25, pp. 3976-3987.
Lu et al., "Ptr-miR397a is a negative regulator of laccase genes affecting lignin content in Populus trichocarpa", PNAS, Jun. 25, 2013, vol. 110, No. 26, pp. 10848-10853.
Ranocha et al., "Biochemical characterization, molecular cloning and expression of laccases—a divergent gene family—in poplar", Eur. J. Biochem, 1999, vol. 259, pp. 485-495.
Sterjiades et al., "Laccase from sycamore maple (*Acer pseudoplatanus*) polymerizes monolignols", Plant Physiology, 1992, vol. 99, pp. 1162-1168.
McCaig et al., "Gene strcture and molecular analysis of the laccase-like multicopper oxidase (LMCO) gene family in *Arabidopsis thaliana*", Planta, 2005, vol. 221, pp. 619-636.
Turlapati et al. "The laccase multigene family in *Arabidopsis thaliana*: towards addressing the mystery of their gene function(s)", Planta, vol. 233, pp. 439-470.

* cited by examiner

*Primary Examiner* — Brent T Page
(74) *Attorney, Agent, or Firm* — Scully Scott Murphy & Presser

(57) ABSTRACT

This disclosure provides genetically modified plants having desirable levels of sugar release and syringyl/guaiacyl (S/G) ratio; methods of genetically modifying plants to modulate sugar release and S/G ratio; and uses of such plants. The inventors have determined that genetic modification of a laccase gene (LAC2) from *Populus*, encoded by locus Potri.008G064000 resulted in transgenic *Populus* trees with changes in syringyl/guaiacyl ratios as well as altered sugar release phenotypes. Plants with altered sugar release, and S/G ratio, based on modulation of the expression or activity of the LAC2 gene, have divergent uses including pulp and paper production, and biofuel and bioproducts production.

11 Claims, 4 Drawing Sheets

Specification includes a Sequence Listing.

SEQUENCE LISTING

<160> NUMBER OF SEQ ID NOS: 67

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide

<400> SEQUENCE: 1
gtatcgtata gtctgaagat ctgg                                          24

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
ggaatcaaag tgccaaatcc                                               20

<210> SEQ ID NO 3
<211> LENGTH: 23
<212> TYPE: DNA
<213> ORGANISM: Artificial Sequence
<220> FEATURE:
<223> OTHER INFORMATION: Oligonucleotide

<400> SEQUENCE: 3
aattgttggt cttcaacgag gaa                                           23

<210> SEQ ID NO 4
<211> LENGTH: 21
<212> TYPE: DNA
<213> ORGANISM: Artificial Sequence
<220> FEATURE:
<223> OTHER INFORMATION: Oligonucleotide

<400> SEQUENCE: 4
aaagggcagg gacgtagtca a                                             21

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide

<400> SEQUENCE: 5
cttgcgctat aagggaacca                                               20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide

<400> SEQUENCE: 6
cccgacaccg atagtgaagt                                               20

<210> SEQ ID NO 7
<211> LENGTH: 556
<212> TYPE: PRT
<213> ORGANISM: Populus trichocarpa

```
<400> SEQUENCE: 7

Met Glu Asn Tyr Arg Ala Arg Ala Ile Leu Leu Leu Val Ile Phe Ile
1               5                   10                  15

Phe Pro Ala Leu Val Glu Cys Glu Val Arg Leu Tyr Asp Phe Arg Val
            20                  25                  30

Val Leu Thr Asn Thr Thr Lys Leu Cys Ser Thr Lys Ser Ile Val Thr
        35                  40                  45

Ile Asn Gly Lys Phe Pro Gly Pro Thr Ile Tyr Ala Arg Glu Gly Asp
    50                  55                  60

Asn Val Asn Ile Lys Leu Thr Asn His Val Gln Tyr Asn Val Thr Ile
65                  70                  75                  80

His Trp His Gly Val Arg Gln Leu Arg Thr Gly Trp Ser Asp Gly Pro
                85                  90                  95

Ala Tyr Ile Thr Gln Cys Pro Ile Arg Pro Gly Gln Ser Tyr Leu Tyr
            100                 105                 110

Asn Phe Thr Leu Thr Gly Gln Arg Gly Thr Leu Leu Trp His Ala His
        115                 120                 125

Ile Ser Trp Leu Arg Ala Thr Ile His Gly Ala Ile Val Ile Leu Pro
    130                 135                 140

Gln Lys Gly Val Pro Tyr Pro Phe Pro Lys Pro Asp Lys Glu Lys Ile
145                 150                 155                 160

Ile Ile Leu Gly Glu Trp Trp Lys Ala Asp Val Glu Ala Val Val Asn
                165                 170                 175

Gln Ala Thr Gln Thr Gly Leu Pro Pro Asn Ile Ser Asp Ala His Ile
            180                 185                 190

Val Asn Gly Gln Thr Gly Ala Val Pro Gly Cys Pro Ser Pro Gly Phe
        195                 200                 205

Thr Leu His Val Glu Ser Gly Lys Thr Tyr Leu Leu Arg Ile Ile Asn
    210                 215                 220

Ala Ala Leu Asn Asp Glu Leu Phe Phe Lys Ile Ala Gly His Asn Ile
225                 230                 235                 240

Thr Val Val Glu Val Asp Ala Ala Tyr Thr Lys Pro Phe Ser Thr Asp
                245                 250                 255

Thr Ile Phe Ile Gly Pro Gly Gln Thr Thr Asn Ala Leu Leu Thr Ala
            260                 265                 270

Asp Lys Ser Val Gly Lys Tyr Leu Met Ala Val Ser Pro Phe Met Asp
        275                 280                 285

Thr Val Val Ala Val Asp Asn Val Thr Ala Ile Ala Phe Leu Arg Tyr
    290                 295                 300

Lys Gly Thr Ile Ala Phe Ser Pro Pro Val Leu Thr Thr Thr Pro Ala
305                 310                 315                 320

Ile Asn Ala Thr Pro Val Thr Ser Thr Phe Met Asp Asn Leu Arg Ser
                325                 330                 335

Leu Asn Ser Lys Lys Phe Pro Ala Asn Val Pro Leu Thr Val Asp His
            340                 345                 350

Ser Leu Tyr Phe Thr Ile Gly Val Gly Ile Asp Pro Cys Ala Thr Cys
        355                 360                 365

Val Asn Gly Ser Lys Ala Val Gly Ala Ile Asn Asn Ile Ser Phe Ile
    370                 375                 380

Met Pro Thr Thr Ala Leu Leu Gln Ala His Tyr Tyr Ser Ile Ser Gly
385                 390                 395                 400

Val Phe Thr Asp Asp Phe Pro Ala Met Pro Pro Asn Ser Phe Asn Tyr
```

```
                405                 410                 415
Thr Gly Asn Asn Thr Ala Leu Asn Leu Gln Thr Ile Asn Gly Thr Arg
            420                 425                 430

Thr Tyr Arg Leu Ala Phe Asn Ser Thr Val Gln Leu Val Leu Gln Gly
        435                 440                 445

Thr Thr Ile Ile Ala Pro Glu Ser His Pro Phe His Leu His Gly Phe
    450                 455                 460

Asn Phe Phe Val Val Gly Lys Gly Phe Gly Asn Phe Asp Ala Asp Asn
465                 470                 475                 480

Asp Pro Lys Lys Phe Asn Leu Ala Asp Pro Val Glu Arg Asn Thr Ile
                485                 490                 495

Ser Val Pro Thr Ala Gly Trp Ala Ala Ile Arg Phe Arg Ala Asp Asn
            500                 505                 510

Pro Gly Val Trp Phe Leu His Cys His Leu Glu Val His Thr Thr Trp
        515                 520                 525

Gly Leu Lys Met Val Phe Val Val Asp Asn Gly Glu Gly Pro Asp Glu
    530                 535                 540

Ser Leu Leu Pro Pro Ser Asp Leu Pro Asn Cys
545                 550                 555

<210> SEQ ID NO 8
<211> LENGTH: 555
<212> TYPE: PRT
<213> ORGANISM: Populus trichocarpa

<400> SEQUENCE: 8

Met Glu Tyr Tyr Gln Ala Arg Thr Met Leu Leu Val Ile Phe Ile Phe
1               5                   10                  15

Pro Ala Leu Val Glu Cys Lys Val Arg Leu Tyr Asn Phe Arg Val Val
            20                  25                  30

Leu Thr Asn Thr Thr Lys Leu Cys Ser Thr Lys Ser Ile Pro Thr Ile
        35                  40                  45

Asn Gly Lys Phe Pro Gly Pro Thr Ile Tyr Ala Arg Glu Gly Asp Asn
    50                  55                  60

Val Asn Ile Arg Leu Thr Asn Gln Val Gln Tyr Asn Val Thr Val His
65                  70                  75                  80

Trp His Gly Val Arg Gln Leu Arg Thr Gly Trp Ala Asp Gly Pro Ala
                85                  90                  95

Tyr Ile Thr Gln Cys Pro Ile Gln Pro Gly Gln Ser Tyr Leu Tyr Asn
            100                 105                 110

Phe Thr Leu Thr Gly Gln Arg Gly Thr Leu Leu Trp His Ala His Ile
        115                 120                 125

Ser Trp Leu Arg Ala Thr Ile His Gly Ala Ile Val Ile Phe Pro Lys
    130                 135                 140

Lys Gly Val Pro Tyr Pro Phe Pro Lys Pro Asp Lys Glu Lys Ile Ile
145                 150                 155                 160

Ile Leu Ser Glu Trp Trp Lys Ala Asp Val Glu Ala Val Val Asn Gln
                165                 170                 175

Ala Thr Met Thr Gly Leu Pro Pro Asn Ile Ser Asp Ala His Thr Val
            180                 185                 190

Asn Gly His Thr Gly Ala Val Pro Gly Cys Thr Ser Pro Gly Phe Thr
        195                 200                 205

Leu His Val Glu Ser Gly Lys Thr Tyr Leu Leu Arg Ile Ile Asn Ala
    210                 215                 220
```

```
Ala Leu Asn Asp Glu Leu Phe Phe Lys Ile Ala Gly His Asn Ile Thr
225                 230                 235                 240

Val Val Glu Val Asp Ala Thr Phe Thr Lys Pro Phe Ser Thr Asp Thr
            245                 250                 255

Ile Phe Ile Gly Pro Gly Gln Thr Thr Asn Ala Leu Leu Thr Ala Asp
            260                 265                 270

Lys Ser Ile Gly Lys Tyr Leu Ile Ala Val Ser Pro Phe Met Asp Thr
            275                 280                 285

Val Val Ala Val Asp Asn Val Thr Ala Ile Ala Phe Leu Arg Tyr Lys
            290                 295                 300

Gly Thr Leu Ala Phe Ser Pro Pro Val Leu Thr Thr Thr Pro Ala Ile
305                 310                 315                 320

Asn Ala Thr Pro Ala Thr Ser Thr Phe Met Asp Lys Leu Arg Ser Leu
                325                 330                 335

Asn Ser Lys Lys Tyr Pro Ala Asn Val Pro Leu Thr Val Asp His Asp
                340                 345                 350

Leu Tyr Phe Thr Ile Gly Val Gly Ile Asp Pro Cys Ala Thr Cys Thr
            355                 360                 365

Asn Gly Ser Lys Ala Val Ala Asp Ile Asn Asn Val Ser Phe Ile Met
370                 375                 380

Pro Thr Thr Ala Leu Leu Gln Ala His Tyr Tyr Asn Ile Ser Gly Val
385                 390                 395                 400

Phe Thr Asp Asp Phe Pro Ala Lys Pro Ile Ser Phe Asn Tyr Thr
                405                 410                 415

Gly Asn Asn Thr Ala Met Asn Leu Lys Thr Thr Asn Gly Thr Arg Ala
            420                 425                 430

Tyr Arg Leu Ala Phe Asn Ser Ala Val Gln Val Val Leu Gln Gly Thr
            435                 440                 445

Thr Ile Ile Ala Pro Glu Ser His Pro Phe His Leu His Gly Phe Asn
450                 455                 460

Phe Phe Val Val Gly Lys Gly Ile Gly Asn Phe Asp Pro Asp Asn Asp
465                 470                 475                 480

Pro Lys Lys Phe Asn Leu Ala Asp Pro Val Glu Arg Asn Thr Val Ser
                485                 490                 495

Val Pro Thr Ala Gly Trp Ile Ala Ile Arg Phe Lys Ala Asp Asn Pro
            500                 505                 510

Gly Val Trp Phe Leu His Cys His Leu Glu Val His Thr Thr Trp Gly
            515                 520                 525

Leu Lys Met Ala Phe Val Val Asp Asn Gly Lys Gly Pro Asn Glu Ser
            530                 535                 540

Ile Leu Pro Pro Ser Asp Leu Pro Thr Cys
545                 550                 555
```

<210> SEQ ID NO 9
<211> LENGTH: 556
<212> TYPE: PRT
<213> ORGANISM: Populus trichocarpa

<400> SEQUENCE: 9

```
Met Asp Met Ala Pro Trp Ile Arg Val Leu Val Leu Ala Cys Leu
1               5                   10                  15

Phe Pro Ala Ser Val Glu Ser Met Val Arg His Tyr Lys Phe Asn Val
            20                  25                  30

Val Met Lys Asn Ser Thr Lys Leu Cys Ser Thr Lys Pro Ile Val Thr
            35                  40                  45
```

```
Val Asn Gly Gln Phe Pro Gly Pro Thr Leu Val Ala Arg Glu Asp Asp
 50                  55                  60

Thr Val Leu Val Lys Val Asn His Val Lys Tyr Asn Val Ser Ile
 65                  70                  75                  80

His Trp His Gly Ile Arg Gln Leu Arg Thr Gly Trp Ala Asp Gly Pro
                     85                  90                  95

Ala Tyr Ile Thr Gln Cys Pro Ile Gln Pro Gly Gln Ser Phe Val Tyr
             100                 105                 110

Asn Phe Thr Ile Thr Gly Gln Arg Gly Thr Leu Leu Trp His Ala His
         115                 120                 125

Ile Leu Trp Leu Arg Ala Thr Val His Gly Ala Ile Val Ile Leu Pro
     130                 135                 140

Lys Arg Gly Val Pro Tyr Pro Phe Pro Thr Pro Arg Lys Glu Lys Val
145                 150                 155                 160

Ile Ile Leu Gly Glu Trp Trp Lys Ser Asp Val Glu Ala Val Ile Asn
                 165                 170                 175

Glu Ala Thr Lys Ser Gly Ile Ala Pro Asn Val Ser Asp Ala His Thr
             180                 185                 190

Ile Asn Gly His Pro Gly Pro Val Ser Ala Cys Ser Ser His Gly Gly
         195                 200                 205

Tyr Asn Leu Ser Val His Pro Gly Lys Thr Tyr Met Leu Arg Ile Ile
     210                 215                 220

Asn Ala Ala Leu Asn Glu Glu Leu Phe Phe Lys Ile Ala Gly His Gln
225                 230                 235                 240

Leu Thr Val Val Glu Val Asp Ala Thr Tyr Val Lys Pro Phe Lys Ile
                 245                 250                 255

Asp Thr Val Val Ile Ala Pro Gly Gln Thr Thr Asn Val Leu Val Thr
             260                 265                 270

Ala Asn Arg Gly Ser Gly Gln Tyr Leu Val Ala Ala Ser Pro Phe Met
         275                 280                 285

Asp Ala Pro Ile Ala Val Asp Asn Val Thr Ala Thr Ala Thr Leu His
     290                 295                 300

Tyr Ser Gly Thr Leu Ala Ser Thr Ile Thr Thr Leu Thr Val Pro Pro
305                 310                 315                 320

Ala Lys Asn Ala Thr Pro Val Ala Thr Asn Phe Thr Asn Ala Leu Arg
                 325                 330                 335

Ser Leu Asn Ser Ile Lys Tyr Pro Ala Arg Val Pro Leu Lys Ile Asp
             340                 345                 350

His Ser Leu Phe Phe Thr Val Gly Leu Gly Val Asn Pro Cys Ala Thr
         355                 360                 365

Cys Ile Asn Gly Ser Arg Val Val Ala Asp Ile Asn Asn Val Thr Phe
     370                 375                 380

Val Met Pro Thr Ile Ala Leu Leu Gln Ala His Val Phe Asn Ile Ser
385                 390                 395                 400

Gly Val Phe Thr Asp Asp Phe Pro Ala Asn Pro Thr Pro Phe Asn
                 405                 410                 415

Tyr Thr Gly Thr Gln Pro Thr Asn Phe Gln Thr Val Lys Gly Thr Lys
             420                 425                 430

Leu Tyr Arg Leu Ala Tyr Asn Asn Thr Val Gln Leu Val Leu Gln Asp
         435                 440                 445

Thr Gly Met Leu Thr Pro Glu Asn His Pro Val His Leu His Gly Phe
     450                 455                 460
```

```
Asn Phe Phe Glu Val Gly Arg Gly Val Gly Asn Phe Asp Pro Asn Lys
465                 470                 475                 480

Asp Pro Lys Lys Phe Asn Leu Val Asp Pro Val Glu Arg Asn Thr Ile
            485                 490                 495

Gly Val Pro Ala Gly Gly Trp Thr Ala Ile Arg Phe Ile Ala Asp Asn
        500                 505                 510

Pro Gly Val Trp Phe Met His Cys His Leu Glu Val His Thr Thr Trp
    515                 520                 525

Gly Leu Lys Met Ala Phe Val Val Asp Asn Gly Lys Gly Pro Asn Glu
530                 535                 540

Ser Val Leu Pro Pro Pro Asp Leu Pro Lys Cys
545                 550                 555

<210> SEQ ID NO 10
<211> LENGTH: 557
<212> TYPE: PRT
<213> ORGANISM: Populus trichocarpa

<400> SEQUENCE: 10

Met Glu Tyr Ser Cys Phe Arg Phe Met Leu Leu Ala Val Cys Leu Phe
1               5                   10                  15

Pro Ala Val Val Glu Cys Arg Ile Arg His Tyr Lys Phe Asn Val Val
            20                  25                  30

Met Lys Asn Thr Thr Arg Leu Cys Ser Ser Lys Pro Ile Val Thr Val
        35                  40                  45

Asn Gly Leu Phe Pro Gly Pro Thr Leu Tyr Ala Arg Glu Asp Asp Thr
    50                  55                  60

Val Leu Val Lys Val Val Asn Arg Val Lys Tyr Asn Leu Ser Ile His
65                  70                  75                  80

Trp His Gly Ile Arg Gln Leu Arg Thr Gly Trp Ala Asp Gly Pro Ala
                85                  90                  95

Tyr Ile Thr Gln Cys Pro Ile Gln Pro Gly Gln Ser Tyr Val Tyr Asn
            100                 105                 110

Phe Thr Ile Thr Gly Gln Arg Gly Thr Leu Leu Trp His Ala His Ile
        115                 120                 125

Leu Trp Leu Arg Ala Thr Val His Gly Ala Leu Val Val Leu Pro Lys
    130                 135                 140

Leu Gly Val Pro Tyr Pro Phe Pro Ala Pro His Lys Glu Val Val Val
145                 150                 155                 160

Val Leu Ala Glu Trp Trp Lys Ser Asp Thr Glu Ala Val Ile Asn Glu
                165                 170                 175

Ala Leu Lys Ser Gly Leu Ala Pro Asn Val Ser Asp Ala His Thr Ile
            180                 185                 190

Asn Gly His Pro Gly Ala Val Ser Thr Cys Ser Ser Gln Gly Gly Phe
        195                 200                 205

Thr Leu Pro Val Gln Ser Gly Lys Thr Tyr Met Leu Arg Leu Ile Asn
    210                 215                 220

Ala Ala Leu Asn Glu Glu Leu Phe Phe Lys Ile Ala Gly His Lys Leu
225                 230                 235                 240

Thr Val Val Glu Val Asp Ala Thr Tyr Val Lys Pro Phe Lys Thr Asp
                245                 250                 255

Thr Val Leu Ile Ala Pro Gly Gln Thr Thr Asn Val Leu Val Thr Thr
            260                 265                 270

Asn Lys Asn Thr Gly Lys Tyr Leu Val Ala Ala Ser Pro Phe Met Asp
    275                 280                 285
```

Ala Pro Ile Ala Val Asp Asn Met Thr Ala Thr Ala Thr Leu His Tyr
290                 295                 300

Ser Gly Ala Leu Ser Asn Ser Pro Thr Thr Leu Thr Ile Pro Pro Pro
305                 310                 315                 320

Lys Asn Ala Thr Ala Leu Ala Asn Gln Phe Thr Asn Ser Leu Arg Ser
            325                 330                 335

Leu Asn Ser Lys Thr Phe Pro Ala Lys Val Pro Leu Thr Val Asp His
            340                 345                 350

Ser Leu Phe Phe Thr Val Gly Leu Gly Ile Asn Pro Cys Pro Thr Cys
        355                 360                 365

Lys Ala Gly Asn Gly Ser Arg Val Val Ala Ser Ile Asn Asn Val Thr
370                 375                 380

Phe Val Met Pro Thr Thr Ala Leu Leu Gln Ala His Phe Phe Asn Ile
385                 390                 395                 400

Ser Gly Val Phe Thr Thr Asp Phe Pro Ala Lys Pro Pro His Val Phe
                405                 410                 415

Asn Tyr Thr Gly Thr Pro Pro Thr Asn Leu Gln Thr Ser Gly Thr
                420                 425                 430

Lys Ala Tyr Arg Leu Pro Tyr Asn Ser Thr Val Gln Leu Val Met Gln
        435                 440                 445

Asp Thr Gly Ile Ile Ser Pro Glu Asn His Pro Ile His Leu His Gly
450                 455                 460

Phe Asn Phe Phe Ala Val Gly Arg Gly Val Gly Asn Tyr Asn Pro Lys
465                 470                 475                 480

Thr Asp Pro Lys Lys Phe Asn Leu Val Asp Pro Val Glu Arg Asn Thr
                485                 490                 495

Ile Gly Val Pro Ser Gly Gly Trp Val Ala Ile Arg Phe Arg Ala Asp
            500                 505                 510

Asn Pro Gly Val Trp Phe Met His Cys His Leu Glu Val His Thr Thr
        515                 520                 525

Trp Gly Leu Lys Met Ala Phe Leu Val Asp Asn Gly Lys Gly Pro Asn
530                 535                 540

Glu Ser Leu Leu Pro Pro Ser Asp Leu Pro Lys Cys
545                 550                 555

<210> SEQ ID NO 11
<211> LENGTH: 564
<212> TYPE: PRT
<213> ORGANISM: Populus trichocarpa

<400> SEQUENCE: 11

Met Ile Arg Lys Ser Ala Lys Met Glu Tyr Ser Trp Phe Arg Phe Met
1               5                   10                  15

Leu Leu Ala Val Ser Leu Phe Pro Ala Leu Val Glu Cys Arg Val Arg
            20                  25                  30

His Tyr Lys Phe Asn Val Met Lys Asn Thr Arg Leu Cys Ser
        35                  40                  45

Ser Lys Pro Val Val Thr Val Asn Gly Arg Phe Pro Gly Pro Thr Leu
50                  55                  60

Tyr Ala Arg Glu Asp Asp Thr Val Leu Val Lys Val Val Asn His Val
65                  70                  75                  80

Lys Tyr Asn Val Ser Ile His Trp His Gly Ile Arg Gln Leu Arg Thr
            85                  90                  95

Gly Trp Ala Asp Gly Pro Ala Tyr Ile Thr Gln Cys Pro Ile Gln Thr

```
                100                 105                 110
Gly Gln Ser Tyr Val Tyr Asn Phe Thr Ile Thr Gly Gln Arg Gly Thr
            115                 120                 125
Leu Leu Trp His Ala His Ile Leu Trp Leu Arg Ala Thr Val His Gly
        130                 135                 140
Ala Ile Val Val Leu Pro Lys Arg Gly Val Pro Tyr Pro Phe Pro Ala
145                 150                 155                 160
Pro His Lys Glu Phe Val Val Leu Ala Glu Trp Trp Lys Ser Asp
                165                 170                 175
Thr Glu Ala Val Ile Asn Glu Ala Leu Lys Ser Gly Leu Ala Pro Asn
            180                 185                 190
Val Ser Asp Ala His Thr Ile Asn Gly His Pro Gly Ala Val Ser Ala
        195                 200                 205
Cys Pro Ser Gln Gly Gly Phe Thr Leu Pro Val Glu Ser Gly Lys Thr
210                 215                 220
Tyr Met Leu Arg Leu Ile Asn Ala Ala Leu Asn Glu Glu Leu Phe Phe
225                 230                 235                 240
Lys Ile Ala Gly His Lys Leu Thr Leu Val Glu Val Asp Ala Thr Tyr
                245                 250                 255
Val Lys Pro Phe Lys Thr Asp Thr Val Leu Ile Ala Pro Gly Gln Thr
            260                 265                 270
Thr Asn Val Leu Val Thr Thr Asn Lys Asn Thr Gly Lys Tyr Leu Val
        275                 280                 285
Ala Ala Ser Pro Phe Met Asp Ala Pro Ile Ala Val Asp Asn Met Thr
290                 295                 300
Ala Thr Ala Thr Leu His Tyr Ser Gly Ala Leu Ser Gly Thr Pro Thr
305                 310                 315                 320
Thr Leu Thr Ile Pro Pro Lys Asn Ala Thr Ala Val Ala Asn Gln
                325                 330                 335
Phe Thr Asn Ser Leu Arg Ser Leu Asn Ser Lys Arg Phe Pro Ala Lys
            340                 345                 350
Val Pro Leu Thr Val Asp His Asn Leu Phe Phe Thr Val Gly Leu Gly
        355                 360                 365
Ile Asn Pro Cys Pro Thr Cys Lys Ala Gly Asn Gly Ser Arg Val Val
370                 375                 380
Ala Ser Ile Asn Asn Val Thr Phe Val Met Pro Thr Thr Ala Leu Leu
385                 390                 395                 400
Gln Ala His Phe Phe Asn Ile Ser Gly Val Phe Thr Thr Asp Phe Pro
                405                 410                 415
Ser Lys Pro Pro His Val Phe Asn Tyr Thr Gly Thr Pro Thr Asn
            420                 425                 430
Leu Gln Thr Thr Ser Gly Thr Lys Val Tyr Arg Leu Arg Tyr Asn Ser
        435                 440                 445
Thr Val Glu Leu Val Met Gln Asp Thr Gly Ile Ile Ser Pro Glu Asn
450                 455                 460
His Pro Ile His Leu His Gly Phe Asn Phe Phe Gly Val Gly Arg Gly
465                 470                 475                 480
Val Gly Asn Tyr Asn Pro Lys Thr Asp Pro Lys Lys Phe Asn Leu Val
                485                 490                 495
Asp Pro Val Glu Arg Asn Thr Ile Gly Val Pro Ser Gly Gly Trp Val
            500                 505                 510
Ala Ile Arg Phe Arg Val Asp Asn Pro Gly Val Trp Phe Met His Cys
        515                 520                 525
```

```
His Leu Glu Val His Thr Thr Trp Gly Leu Lys Met Ala Phe Leu Val
        530                 535                 540

Asp Asn Gly Lys Gly Pro Asn Glu Ser Leu Leu Pro Pro Pro Ser Asp
545                 550                 555                 560

Leu Pro Lys Cys

<210> SEQ ID NO 12
<211> LENGTH: 559
<212> TYPE: PRT
<213> ORGANISM: Populus trichocarpa

<400> SEQUENCE: 12

Met Glu Tyr Ser Asn Leu Leu Ile Arg Phe Met Leu Leu Ala Val Cys
1               5                   10                  15

Leu Leu Pro Ala Leu Val Glu Cys Arg Ile Arg His Tyr Lys Phe Asn
            20                  25                  30

Val Val Met Lys Asn Thr Thr Arg Leu Cys Ser Arg Lys Pro Ile Val
        35                  40                  45

Thr Val Asn Gly Arg Phe Pro Gly Pro Thr Leu Tyr Ala Arg Glu His
    50                  55                  60

Asp Thr Val Leu Val Lys Val Val Asn His Val Lys Tyr Asn Val Ser
65                  70                  75                  80

Ile His Trp His Gly Ile Arg Gln Leu Arg Thr Gly Trp Ala Asp Gly
                85                  90                  95

Pro Ala Tyr Ile Thr Gln Cys Pro Ile Gln Pro Gly Gln Ser Tyr Val
            100                 105                 110

Tyr Asn Phe Thr Ile Thr Gly Gln Arg Gly Thr Leu Leu Trp His Ala
        115                 120                 125

His Ile Leu Trp Leu Arg Ala Thr Val His Gly Ala Leu Val Val Leu
    130                 135                 140

Pro Lys Arg Gly Ile Pro Tyr Pro Phe Pro Ala Pro His Lys Glu Val
145                 150                 155                 160

Leu Val Val Leu Ala Glu Trp Trp Lys Ser Asp Thr Glu Ala Val Ile
                165                 170                 175

Asn Glu Ala Leu Lys Ser Gly Leu Ala Pro Asn Val Ser Asp Ala His
            180                 185                 190

Thr Ile Asn Gly His Pro Gly Ala Val Ser Ala Cys Ser Ser Gln Gly
        195                 200                 205

Gly Phe Thr Leu Pro Val Lys Ser Gly Glu Thr Tyr Met Leu Arg Leu
    210                 215                 220

Ile Asn Ala Ala Leu Asn Glu Glu Leu Phe Phe Lys Ile Ala Gly His
225                 230                 235                 240

Lys Leu Thr Val Val Glu Val Asp Ala Thr Tyr Val Lys Pro Phe Lys
                245                 250                 255

Thr Asp Thr Val Leu Ile Ala Pro Gly Gln Thr Thr Asn Val Leu Val
            260                 265                 270

Thr Ala Asn Lys Asn Thr Gly Lys Tyr Leu Val Ala Ala Ser Pro Phe
        275                 280                 285

Met Asp Ala Pro Ile Ala Val Asp Asn Met Thr Ala Thr Ala Thr Leu
    290                 295                 300

Gln Tyr Ser Gly Ala Leu Ala Asn Ser Pro Thr Thr Leu Thr Thr Pro
305                 310                 315                 320

Pro Pro Lys Asn Ala Thr Ala Val Ala Asn Gln Phe Thr Asn Ser Leu
                325                 330                 335
```

-continued

Arg Ser Leu Asn Ser Arg Arg Phe Pro Ala Lys Val Pro Leu Asn Val
                340                 345                 350

Asp His Asn Leu Phe Phe Thr Val Gly Leu Gly Val Asn Pro Cys Pro
                355                 360                 365

Ser Cys Lys Ala Gly Asn Gly Ser Arg Val Val Ala Ser Ile Asn Asn
        370                 375                 380

Val Thr Phe Val Met Pro Thr Thr Ala Leu Leu Gln Ala His Phe Leu
385                 390                 395                 400

Asn Ile Ser Gly Val Phe Thr Thr Asp Phe Pro Ala Lys Pro Pro His
                405                 410                 415

Val Phe Asn Tyr Thr Gly Thr Pro Pro Thr Asn Leu Gln Thr Lys Ser
                420                 425                 430

Gly Thr Lys Val Tyr Arg Leu Ser Tyr Asn Ser Thr Val Gln Leu Val
                435                 440                 445

Met Gln Asp Thr Gly Ile Ile Ser Pro Glu Asn His Pro Ile His Leu
        450                 455                 460

His Gly Phe Asn Phe Phe Ala Val Gly Arg Gly Val Gly Asn Tyr Asn
465                 470                 475                 480

Pro Lys Thr Asp Thr Lys Lys Phe Asn Leu Val Asp Pro Val Glu Arg
                485                 490                 495

Asn Thr Ile Gly Val Pro Ser Gly Gly Trp Val Ala Ile Arg Phe Arg
        500                 505                 510

Ala Asp Asn Pro Gly Val Trp Phe Met His Cys His Leu Glu Val His
        515                 520                 525

Thr Thr Trp Gly Leu Lys Met Ala Phe Leu Val Asp Asn Gly Lys Gly
        530                 535                 540

Pro Lys Glu Ser Leu Leu Pro Pro Ser Asp Leu Pro Lys Cys
545                 550                 555

<210> SEQ ID NO 13
<211> LENGTH: 559
<212> TYPE: PRT
<213> ORGANISM: Populus trichocarpa

<400> SEQUENCE: 13

Met Glu Tyr Ser Asn Trp Leu Ile Arg Phe Met Leu Leu Ala Val Cys
1               5                   10                  15

Leu Leu Pro Ala Leu Val Glu Cys Arg Ile Arg His Tyr Lys Phe Asn
                20                  25                  30

Val Val Met Lys Asn Thr Thr Arg Leu Cys Ser Arg Lys Pro Ile Val
            35                  40                  45

Thr Val Asn Gly Arg Phe Pro Gly Pro Thr Leu Tyr Ala Arg Glu His
    50                  55                  60

Asp Thr Val Leu Val Lys Val Val Asn His Val Lys Tyr Asn Val Ser
65              70                  75                  80

Ile His Trp His Gly Ile Arg Gln Leu Arg Thr Gly Trp Ala Asp Gly
                85                  90                  95

Pro Ala Tyr Ile Thr Gln Cys Pro Ile Gln Pro Gly Gln Ser Tyr Val
            100                 105                 110

Tyr Asn Phe Thr Ile Thr Gly Gln Arg Gly Thr Leu Trp His Ala
            115                 120                 125

His Ile Leu Trp Leu Arg Ala Thr Val His Gly Ala Met Val Val Leu
        130                 135                 140

Pro Lys Arg Gly Ile Pro Tyr Pro Phe Pro Ala Pro His Lys Glu Val

```
            145                 150                 155                 160
        Val Val Val Leu Ala Glu Trp Trp Lys Ser Asp Thr Glu Ala Val Ile
                        165                 170                 175
        Asn Glu Ala Leu Lys Ser Gly Leu Ala Pro Asn Val Ser Asp Ala His
                        180                 185                 190
        Thr Ile Asn Gly His Pro Gly Ala Val Ser Ala Cys Ser Ser Gln Gly
                        195                 200                 205
        Gly Phe Thr Leu Pro Val Lys Ser Gly Glu Thr Tyr Met Leu Arg Leu
                        210                 215                 220
        Ile Asn Ala Ala Leu Asn Glu Glu Leu Phe Phe Lys Ile Ala Gly His
        225                 230                 235                 240
        Lys Leu Thr Val Val Glu Val Asp Ala Thr Tyr Val Lys Pro Phe Lys
                        245                 250                 255
        Thr Asp Thr Val Leu Ile Ala Pro Gly Gln Thr Thr Asn Val Leu Val
                        260                 265                 270
        Thr Thr Asn Lys Asn Thr Gly Lys Tyr Leu Val Ala Ala Ser Pro Phe
                        275                 280                 285
        Met Asp Ala Pro Ile Ala Val Asp Asn Met Thr Ala Thr Ala Thr Leu
                        290                 295                 300
        Gln Tyr Ser Gly Ala Leu Ala Asn Ser Pro Thr Thr Leu Thr Thr Pro
        305                 310                 315                 320
        Pro Pro Lys Asn Ala Thr Ala Val Ala Asn Gln Phe Thr Asn Ser Leu
                        325                 330                 335
        Arg Ser Leu Asn Ser Arg Arg Phe Pro Ala Lys Val Pro Leu Asn Val
                        340                 345                 350
        Asp His Asn Leu Phe Phe Thr Val Gly Leu Gly Val Asn Pro Cys Pro
                        355                 360                 365
        Ser Cys Lys Ala Gly Asn Gly Ser Arg Val Val Ala Ser Ile Asn Asn
                        370                 375                 380
        Val Thr Phe Val Met Pro Thr Thr Ala Leu Leu Gln Ala His Phe Phe
        385                 390                 395                 400
        Asn Ile Ser Gly Val Phe Thr Thr Asp Phe Pro Ala Lys Pro Pro His
                        405                 410                 415
        Val Phe Asn Tyr Thr Gly Thr Pro Pro Thr Asn Leu Gln Thr Lys Ser
                        420                 425                 430
        Gly Thr Lys Val Tyr Arg Leu Ser Tyr Asn Ser Thr Val Gln Leu Val
                        435                 440                 445
        Met Gln Asp Thr Gly Ile Ile Ser Pro Glu Asn His Pro Ile His Leu
        450                 455                 460
        His Gly Phe Asn Phe Phe Ala Val Gly Arg Gly Val Gly Asn Tyr Asn
        465                 470                 475                 480
        Pro Lys Thr Asp Thr Lys Lys Phe Asn Leu Val Asp Pro Val Glu Arg
                        485                 490                 495
        Asn Thr Ile Gly Val Pro Ser Gly Gly Trp Val Ala Ile Arg Phe Arg
                        500                 505                 510
        Ala Asp Asn Pro Gly Val Trp Phe Met His Cys His Leu Glu Val His
                        515                 520                 525
        Thr Thr Trp Gly Leu Lys Met Ala Phe Leu Val Asp Asn Gly Lys Gly
                        530                 535                 540
        Pro Lys Glu Ser Leu Leu Pro Pro Ser Asp Leu Pro Lys Cys
        545                 550                 555

<210> SEQ ID NO 14
```

```
<211> LENGTH: 557
<212> TYPE: PRT
<213> ORGANISM: Populus trichocarpa

<400> SEQUENCE: 14

Met Val Asp Met Ala Leu Trp Leu Arg Val Leu Val Leu Val Ala Cys
1               5                   10                  15

Leu Phe Pro Ala Ser Val Glu Ser Met Val Arg His Tyr Lys Phe Asn
                20                  25                  30

Val Val Met Lys Asn Thr Thr Arg Leu Cys Ser Glu Lys Pro Ile Val
            35                  40                  45

Thr Val Asn Gly Arg Phe Pro Gly Pro Thr Leu Val Ala Arg Glu Asp
        50                  55                  60

Asp Thr Val Leu Val Lys Val Asn His Val Lys Tyr Asn Val Ser
65                  70                  75                  80

Ile His Trp His Gly Ile Arg Gln Leu Arg Thr Gly Trp Ala Asp Gly
                85                  90                  95

Pro Ala Tyr Ile Thr Gln Cys Pro Leu Gln Pro Gly Gln Asn Phe Val
                100                 105                 110

Tyr Asn Phe Thr Ile Thr Gly Gln Arg Gly Thr Leu Leu Trp His Ala
            115                 120                 125

His Ile Leu Trp Leu Arg Ala Thr Val His Gly Gly Ile Val Ile Leu
        130                 135                 140

Pro Lys Arg Gly Val Pro Tyr Pro Phe Pro Thr Pro His Arg Glu Glu
145                 150                 155                 160

Val Ile Val Leu Gly Glu Trp Trp Lys Ser Asp Val Glu Ala Val Ile
                165                 170                 175

Asn Glu Ala Met Asn Ser Gly Arg Ala Pro Asn Val Ser Asp Ala His
                180                 185                 190

Thr Ile Asn Gly His Pro Gly Pro Val Ser Gly Cys Ser Ser Gln Gly
            195                 200                 205

Gly Tyr Asn Leu Pro Val Arg Pro Gly Lys Thr Tyr Met Leu Arg Ile
        210                 215                 220

Ile Asn Ala Ala Leu Asn Glu Glu Leu Phe Phe Lys Ile Ala Gly His
225                 230                 235                 240

Gln Leu Thr Val Val Glu Val Asp Ala Thr Tyr Val Lys Pro Phe Lys
                245                 250                 255

Ile Asp Thr Ile Val Ile Ala Pro Gly Gln Thr Thr Asn Val Leu Val
            260                 265                 270

Thr Ala Asn Arg Gly Ser Gly Lys Tyr Leu Val Ala Ala Ser Pro Phe
        275                 280                 285

Met Asp Ala Pro Ile Ala Val Asp Asn Val Thr Ala Thr Ala Thr Leu
290                 295                 300

His Tyr Ser Gly Thr Leu Ala Ser Thr Thr Thr Leu Thr Val Pro
305                 310                 315                 320

Pro Ala Gln Asn Ala Thr Pro Val Ala Thr Asn Phe Thr Asp Ala Leu
                325                 330                 335

Arg Ser Leu Asn Ser Ile Lys Tyr Pro Ala Arg Val Pro Leu Lys Ile
            340                 345                 350

Asp His Ser Leu Phe Phe Thr Ile Gly Leu Gly Val Asn Pro Cys Ala
        355                 360                 365

Thr Cys Val Asn Gly Asn Arg Val Val Ala Asp Ile Asn Asn Val Thr
370                 375                 380

Phe Val Met Pro Thr Ile Ala Leu Leu Gln Ala His Phe Phe Asn Ile
```

```
            385                 390                 395                 400
Lys Gly Val Phe Thr Asp Asp Phe Pro Gly Asn Pro Pro Thr Pro Phe
                405                 410                 415

Asn Tyr Thr Gly Thr Gln Pro Lys Asn Phe Gln Thr Val Asn Gly Thr
                420                 425                 430

Lys Leu Tyr Arg Leu Ala Tyr Asn Ser Thr Val Gln Leu Val Leu Gln
                435                 440                 445

Asp Thr Gly Met Leu Thr Pro Glu Asn His Pro Val His Leu His Gly
450                 455                 460

Phe Asn Phe Phe Glu Val Gly Arg Gly Ile Gly Asn Phe Asn Pro Lys
465                 470                 475                 480

Arg Asp Pro Lys Lys Phe Asn Leu Ala Asp Pro Val Glu Arg Asn Thr
                485                 490                 495

Ile Gly Val Pro Ala Gly Gly Trp Thr Ala Ile Arg Phe Ile Ala Asp
                500                 505                 510

Asn Pro Gly Val Trp Phe Met His Cys His Leu Glu Val His Thr Thr
                515                 520                 525

Trp Gly Leu Lys Met Ala Phe Val Val Asp Asn Gly Lys Gly Pro Asn
                530                 535                 540

Glu Ser Val Leu Pro Pro Pro Asp Leu Pro Lys Cys
545                 550                 555

<210> SEQ ID NO 15
<211> LENGTH: 558
<212> TYPE: PRT
<213> ORGANISM: Populus trichocarpa

<400> SEQUENCE: 15

Met Glu Tyr Ala Cys Trp Leu Arg Phe Met Leu Leu Ala Val Cys Leu
1               5                   10                  15

Phe Pro Ala Leu Val Gln Cys Arg Val Arg His Tyr Lys Phe Asn Val
                20                  25                  30

Val Met Lys Asn Thr Thr Arg Leu Cys Ser Arg Lys Pro Ile Val Thr
                35                  40                  45

Val Asn Gly Arg Phe Pro Gly Pro Thr Leu Tyr Ala Arg Glu Asp Asp
                50                  55                  60

Thr Val Leu Val Lys Val Val Asn His Val Lys Tyr Asn Val Ser Ile
65                  70                  75                  80

His Trp His Gly Ile Arg Gln Leu Arg Thr Gly Trp Ala Asp Gly Pro
                85                  90                  95

Ala Tyr Ile Thr Gln Cys Pro Ile Gln Pro Gly Gln Ser Tyr Val Tyr
                100                 105                 110

Asn Phe Thr Ile Thr Gly Gln Arg Gly Thr Leu Leu Trp His Ala His
                115                 120                 125

Ile Leu Trp Leu Arg Ala Thr Val His Gly Ala Met Val Val Leu Pro
                130                 135                 140

Lys Arg Gly Ile Pro Tyr Pro Phe Pro Gly Pro His Lys Glu Val Val
145                 150                 155                 160

Val Val Leu Ala Glu Trp Trp Lys Ser Asp Thr Glu Ala Val Ile Asn
                165                 170                 175

Glu Ala Leu Lys Ser Gly Leu Ala Pro Asn Val Ser Asp Ala His Thr
                180                 185                 190

Ile Asn Gly His Pro Gly Ala Val Ser Thr Cys Ser Ser Gln Gly Gly
                195                 200                 205
```

Phe Thr Leu Pro Val Lys Ser Gly Glu Thr Tyr Met Leu Arg Leu Ile
210                 215                 220

Asn Ala Ala Leu Asn Glu Glu Leu Phe Phe Lys Ile Ala Gly His Lys
225                 230                 235                 240

Leu Thr Val Val Glu Val Asp Ala Thr Tyr Val Lys Pro Phe Lys Thr
            245                 250                 255

Asp Thr Val Leu Ile Ala Pro Gly Gln Thr Thr Asn Val Leu Val Thr
            260                 265                 270

Thr Asn Lys Asn Thr Gly Lys Tyr Leu Val Ala Ala Ser Pro Phe Met
        275                 280                 285

Asp Ser Pro Ile Ala Val Asp Asn Met Thr Ala Thr Ala Thr Leu Gln
290                 295                 300

Tyr Ser Gly Ala Leu Ala Asn Ser Pro Thr Thr Leu Thr Thr Pro Pro
305                 310                 315                 320

Pro Lys Asn Ala Thr Ala Val Ala Asn Gln Phe Thr Asn Ser Leu Arg
                325                 330                 335

Ser Leu Asn Ser Arg Arg Phe Pro Ala Lys Val Pro Leu Asn Val Asp
            340                 345                 350

His Asn Leu Phe Phe Thr Val Ser Leu Gly Val Asn Pro Cys Pro Ser
        355                 360                 365

Cys Lys Ala Gly Asn Gly Ser Arg Val Val Ala Ser Ile Asn Asn Val
370                 375                 380

Thr Phe Val Met Pro Thr Thr Ala Leu Leu Gln Ala His Phe Leu Asn
385                 390                 395                 400

Ile Ser Gly Val Phe Thr Thr Asp Phe Pro Ala Lys Pro Pro His Val
                405                 410                 415

Phe Asn Tyr Thr Gly Thr Pro Pro Thr Asn Leu Gln Thr Lys Ser Gly
            420                 425                 430

Thr Lys Val Tyr Arg Leu Ser Tyr Asn Ser Thr Val Gln Leu Val Met
        435                 440                 445

Gln Asp Thr Gly Ile Ile Ser Pro Glu Asn His Pro Ile His Leu His
450                 455                 460

Gly Phe Asn Phe Phe Ala Val Gly Arg Gly Val Gly Asn Tyr Asn Pro
465                 470                 475                 480

Lys Thr Asp Thr Lys Lys Phe Asn Leu Val Asp Pro Val Glu Arg Asn
                485                 490                 495

Thr Ile Gly Val Pro Ser Gly Gly Trp Val Ala Ile Arg Phe Arg Ala
            500                 505                 510

Asp Asn Pro Gly Val Trp Phe Met His Cys His Leu Glu Val His Thr
        515                 520                 525

Thr Trp Gly Leu Lys Met Ala Phe Leu Val Asp Asn Gly Lys Gly Pro
530                 535                 540

Lys Glu Ser Leu Leu Pro Pro Ser Asp Leu Pro Lys Cys
545                 550                 555

<210> SEQ ID NO 16
<211> LENGTH: 562
<212> TYPE: PRT
<213> ORGANISM: Populus trichocarpa

<400> SEQUENCE: 16

Met Val Ser Ser Arg Gly Phe Leu Ser Trp Leu Ile Phe Leu Phe Ile
1               5                   10                  15

Gly Ile Leu Gly Phe Ile Pro Phe Pro Ala Glu Ala Ala Ile Lys Lys
            20                  25                  30

```
Tyr Gln Phe Asp Ile Gln Val Lys Asn Val Ser Arg Leu Cys His Ala
         35                  40                  45

Lys Pro Ile Val Thr Val Asn Gly Arg Phe Pro Gly Pro Thr Ile Tyr
 50                  55                  60

Val Arg Glu Gly Asp Arg Val Met Val Asn Val Thr Asn Tyr Ala Gln
 65                  70                  75                  80

Tyr Asn Met Ser Ile His Trp His Gly Leu Lys Gln Tyr Arg Asn Gly
                 85                  90                  95

Trp Ala Asp Gly Pro Ala Tyr Ile Thr Gln Cys Pro Ile Gln Thr Gly
                100                 105                 110

Ser Ser Tyr Thr Tyr Asp Phe Asn Val Thr Gly Gln Arg Gly Thr Leu
            115                 120                 125

Trp Trp His Ala His Ile Leu Trp Leu Arg Ala Thr Val Tyr Gly Ala
        130                 135                 140

Ile Val Ile Met Pro Lys Gln Gly Thr Pro Tyr Pro Phe Pro Gln Pro
145                 150                 155                 160

Asn Met Glu Val Pro Ile Leu Gly Glu Trp Trp Asn Thr Asp Val
                165                 170                 175

Glu Glu Val Glu Lys Gln Gly Thr Glu Met Gly Leu Pro Pro Asn Met
            180                 185                 190

Ser Asp Ala His Thr Ile Asn Gly Lys Pro Gly Pro Leu Phe Pro Cys
        195                 200                 205

Ser Glu Lys His Thr Phe Ala Met Glu Ile Glu Ser Gly Lys Thr Tyr
    210                 215                 220

Leu Leu Arg Ile Ile Asn Ala Ala Leu Asn Asp Glu Leu Phe Phe Gly
225                 230                 235                 240

Ile Ala Gly His Asn Met Thr Val Val Glu Val Asp Ala Val Tyr Thr
                245                 250                 255

Lys Pro Phe Thr Thr Gln Thr Ile Leu Ile Ala Pro Gly Gln Thr Thr
            260                 265                 270

Asn Val Leu Val Leu Ala Asn Gln Val Pro Gly Arg Tyr Phe Met Ala
        275                 280                 285

Thr Arg Ala Phe Leu Asp Val Pro Leu Pro Val Asp Asn Lys Thr Ala
290                 295                 300

Thr Ala Ile Met Gln Tyr Lys Gly Ile Pro Asn Thr Asp Leu Pro Ser
305                 310                 315                 320

Phe Pro Gln Leu Pro Ala Ser Asn Asp Thr Glu Phe Ala Leu Gly Tyr
                325                 330                 335

Asn Arg Lys Leu Arg Ser Leu Asn Thr Ala Gln Phe Pro Ala Asn Val
            340                 345                 350

Pro Leu Lys Val Asp Arg Asn Leu Phe Tyr Thr Val Gly Phe Gly Lys
        355                 360                 365

Asp Ser Cys Pro Thr Cys Val Asn Gly Thr Arg Leu Leu Ala Ser Leu
    370                 375                 380

Asn Asn Ile Ser Phe Val Met Pro Gln Ile Gly Leu Leu Gln Ala His
385                 390                 395                 400

Tyr Phe Asn Ile Ser Gly Val Phe Lys Thr Asn Phe Pro Asp Lys Pro
                405                 410                 415

Pro Thr Pro Phe Asn Tyr Thr Gly Ala Pro Leu Thr Ala Ser Leu Gly
            420                 425                 430

Thr Val His Gly Thr Arg Leu Ser Lys Ile Ala Phe Asn Ser Thr Val
        435                 440                 445
```

```
Glu Leu Val Leu Gln Asp Thr Asn Leu Leu Thr Val Glu Ser His Pro
        450                 455                 460

Phe His Leu His Gly Tyr Asn Phe Phe Val Val Gly Thr Gly Ile Gly
465                 470                 475                 480

Asn Phe Asp Pro Ala Lys Asp Pro Ala Lys Tyr Asn Leu Val Asp Pro
                485                 490                 495

Val Glu Arg Asn Thr Val Gly Val Pro Thr Gly Gly Trp Thr Ala Ile
            500                 505                 510

Arg Phe Arg Ala Asp Asn Pro Gly Val Trp Phe Met His Cys His Leu
            515                 520                 525

Glu Leu His Thr Gly Trp Gly Leu Lys Thr Ala Phe Val Val Glu Glu
        530                 535                 540

Gly Pro Gly Ser Asp Gln Ser Ile Leu Pro Pro Pro Lys Asp Leu Pro
545                 550                 555                 560

Pro Cys

<210> SEQ ID NO 17
<211> LENGTH: 561
<212> TYPE: PRT
<213> ORGANISM: Populus trichocarpa

<400> SEQUENCE: 17

Met Ala Ala Ala Leu Ser Lys Lys Leu Cys Trp Ala Ser Tyr Ile Leu
1               5                   10                  15

Tyr Leu Tyr Phe Ile Tyr His Pro Ala Glu Ala Val Lys Arg Tyr
            20                  25                  30

Gln Phe Asp Ile Gln Val Lys Asn Val Ser Arg Leu Cys His Ala Lys
        35                  40                  45

Pro Ile Val Thr Val Asn Gly Arg Phe Pro Gly Pro Thr Val Tyr Val
    50                  55                  60

Arg Glu Gly Asp Arg Val Leu Val Asn Val Thr Asn His Ala Arg Tyr
65                  70                  75                  80

Asn Met Ser Ile His Trp His Gly Leu Lys Gln Phe Arg Asn Gly Trp
                85                  90                  95

Ala Asp Gly Pro Ala Tyr Ile Thr Gln Cys Pro Ile Lys Thr Gly His
            100                 105                 110

Ser Tyr Thr Tyr Asp Phe Asn Val Thr Gly Gln Arg Gly Thr Leu Trp
        115                 120                 125

Trp His Ala His Ile Leu Trp Leu Arg Ala Thr Val Tyr Gly Ala Ile
130                 135                 140

Val Ile Met Pro Lys Pro Gly Thr Pro Phe Pro Phe Pro Gln Pro His
145                 150                 155                 160

Arg Glu Glu Ile Ile Ile Phe Gly Glu Trp Trp Asn Asn Asp Val Glu
                165                 170                 175

Asp Ile Glu Lys Gln Gly Asn Lys Leu Gly Leu Pro Pro Asn Ala Ser
            180                 185                 190

Asp Ala His Thr Ile Asn Gly Lys Pro Gly Pro Leu Phe Pro Cys Ser
        195                 200                 205

Glu Lys His Thr Phe Thr Leu Glu Val Glu Gln Ala Lys Thr Tyr Leu
    210                 215                 220

Leu Arg Ile Ile Asn Ala Ala Leu Asn Asp Glu Leu Phe Phe Ala Ile
225                 230                 235                 240

Ala Gly His Asn Met Thr Val Val Glu Ile Asp Ala Val Tyr Thr Lys
                245                 250                 255
```

```
Pro Phe Thr Thr Gln Thr Ile Leu Ile Ala Pro Gly Gln Thr Thr Asn
                260                 265                 270

Val Leu Val Gln Ala Thr Gln Thr Pro Asn Arg Tyr Phe Met Ala Ala
            275                 280                 285

Arg Pro Phe Met Asp Ala Pro Leu Ser Ile Asp Asn Lys Thr Ala Thr
        290                 295                 300

Ala Ile Leu Gln Tyr Lys Gly Ile Pro Asn Thr Val Leu Pro Leu Leu
305                 310                 315                 320

Pro Gln Leu Pro Glu Pro Asn Asp Thr Ala Phe Ala Arg Ser Tyr Asn
                325                 330                 335

Ala Lys Leu Arg Ser Leu Asn Ser Pro Gln Phe Gln Ala Asn Val Pro
            340                 345                 350

Leu Ile Val Asp Arg His Leu Phe Tyr Thr Ile Gly Leu Gly Ile Asn
        355                 360                 365

Pro Cys Pro Thr Cys Leu Asn Gly Thr Lys Leu Thr Ala Ser Leu Asn
370                 375                 380

Asn Ile Thr Phe Val Met Pro Gln Ile Gly Leu Leu Gln Ala His Tyr
385                 390                 395                 400

Phe Asn Ile Lys Gly Val Phe Arg Leu Asp Phe Pro Asp Asn Pro Pro
                405                 410                 415

Thr Pro Phe Asn Tyr Thr Gly Ala Pro Leu Thr Ala Asn Leu Gly Thr
            420                 425                 430

Thr Leu Gly Thr Arg Val Ser Lys Ile Ala Tyr Asn Ser Thr Val Gln
        435                 440                 445

Leu Val Leu Gln Asp Thr Asn Leu Leu Thr Val Glu Ser His Pro Phe
450                 455                 460

His Leu His Gly Tyr Asn Phe Phe Val Val Gly Thr Gly Ile Gly Asn
465                 470                 475                 480

Phe Asp Pro Lys Arg Asp Pro Ala Lys Phe Asn Leu Val Asp Pro Pro
                485                 490                 495

Glu Arg Asn Thr Val Gly Val Pro Thr Gly Gly Trp Thr Ala Ile Arg
            500                 505                 510

Phe Arg Ala Asp Asn Pro Gly Val Trp Phe Met His Cys His Leu Glu
        515                 520                 525

Leu His Thr Gly Trp Gly Leu Lys Thr Ala Phe Val Val Glu Asn Gly
530                 535                 540

Lys Leu Pro Asp Gln Ser Ile Leu Pro Pro Lys Asp Leu Pro Pro
545                 550                 555                 560
Cys

<210> SEQ ID NO 18
<211> LENGTH: 564
<212> TYPE: PRT
<213> ORGANISM: Populus trichocarpa

<400> SEQUENCE: 18

Met Ala Ala Ala Leu Ser Lys Ser Phe Cys Leu Gly Tyr Tyr Phe Leu
1               5                   10                  15

Leu Leu Cys Leu Ile Gly Phe Ile Ser His Pro Ala Lys Ala Ala Val
            20                  25                  30

Lys Lys Tyr Leu Phe Asp Ile Gln Val Lys Asn Val Ser Arg Leu Cys
        35                  40                  45

His Ala Lys Pro Ile Val Thr Val Asn Gly Arg Phe Pro Gly Pro Thr
    50                  55                  60
```

Val Tyr Val Arg Glu Gly Asp Arg Val Gln Val Asn Val Thr Asn His
 65                  70                  75                  80

Ala Lys Tyr Asn Met Ser Ile His Trp His Gly Leu Lys Gln Phe Arg
             85                  90                  95

Asn Gly Trp Ala Asp Gly Pro Ala Tyr Ile Thr Gln Cys Pro Ile Lys
        100                 105                 110

Thr Gly His Ser Tyr Thr Tyr Asp Phe Asn Val Thr Gly Gln Arg Gly
    115                 120                 125

Thr Leu Trp Trp His Ala His Ile Phe Trp Leu Arg Ala Thr Val Tyr
130                 135                 140

Gly Ala Ile Val Ile Met Pro Lys Pro Gly Thr Pro Phe Pro Phe Pro
145                 150                 155                 160

Gln Pro His Arg Glu Glu Thr Ile Ile Leu Gly Glu Trp Trp Asn Asn
                165                 170                 175

Asp Val Glu Glu Ile Glu Lys Gln Gly Ser Lys Leu Gly Leu Pro Pro
            180                 185                 190

Asn Ala Ser Asp Ala His Thr Ile Asn Gly Lys Pro Gly Thr Leu Phe
        195                 200                 205

Pro Cys Ser Glu Lys His Thr Phe Ala Met Glu Val Glu Gln Gly Lys
    210                 215                 220

Thr Tyr Leu Leu Arg Ile Ile Asn Ala Ala Leu Asn Asp Glu Leu Phe
225                 230                 235                 240

Phe Ala Ile Ala Gly His Asn Met Thr Val Val Glu Val Asp Ala Val
                245                 250                 255

Tyr Thr Lys His Phe Thr Thr Gln Ala Val Leu Ile Ala Pro Gly Gln
            260                 265                 270

Thr Thr Asn Val Leu Val Gln Ala Thr Gln Ser Pro Asn Arg Tyr Phe
        275                 280                 285

Met Ala Ala Arg Pro Phe Met Asp Ala Pro Leu Thr Val Asp Asn Lys
    290                 295                 300

Thr Ala Thr Ala Ile Leu Gln Tyr Lys Gly Ile Pro Asn Thr Val Ile
305                 310                 315                 320

Pro Ile Leu Pro Lys Leu Pro Ala Pro Asn Asp Thr Ala Phe Ala Leu
                325                 330                 335

Ser Tyr Asn Ala Lys Leu Arg Ser Leu Asn Ser Pro Gln Phe Pro Ala
            340                 345                 350

Asn Val Pro Leu Lys Val Asp Arg His Leu Phe Tyr Thr Ile Gly Leu
        355                 360                 365

Gly Ile Asn Pro Cys Pro Ser Cys Leu Asn Gly Thr Arg Leu Thr Ala
    370                 375                 380

Ser Leu Asn Asn Ile Thr Phe Val Met Pro Gln Ile Gly Leu Leu Gln
385                 390                 395                 400

Ala His Tyr Phe Asn Thr Lys Gly Ile Phe Arg Leu Asp Phe Pro Asp
                405                 410                 415

Asn Pro Pro Ser Pro Phe Asn Tyr Thr Gly Val Pro Leu Thr Ala Asn
            420                 425                 430

Leu Gly Thr Thr Leu Gly Thr Arg Leu Ser Lys Ile Val Tyr Asn Ser
        435                 440                 445

Thr Val Gln Leu Val Leu Gln Asp Thr Asn Leu Leu Thr Val Glu Ser
    450                 455                 460

His Pro Phe His Leu His Gly Tyr Asn Phe Val Val Gly Thr Gly
465                 470                 475                 480

Ile Gly Asn Phe Asp Pro Lys Lys Asp Pro Ala Lys Phe Asn Leu Val

```
                        485                 490                 495
Asp Pro Pro Glu Arg Asn Thr Val Gly Val Pro Thr Gly Gly Trp Thr
                    500                 505                 510

Ala Ile Arg Phe Lys Ala Asp Asn Pro Gly Val Trp Phe Met His Cys
                515                 520                 525

His Leu Glu Leu His Thr Ser Trp Gly Leu Lys Thr Ala Phe Val Val
            530                 535                 540

Glu Asp Gly Val Gly Pro Asp Gln Ser Ile Leu Pro Pro Lys Asp
545                 550                 555                 560

Leu Pro Pro Cys

<210> SEQ ID NO 19
<211> LENGTH: 579
<212> TYPE: PRT
<213> ORGANISM: Populus trichocarpa

<400> SEQUENCE: 19

Met Gly Ser Ala Phe Leu Arg Ile Leu Val Thr Ala Leu Cys Ala Leu
1               5                   10                  15

Trp Ile Phe Ser Glu Leu Val Val Ala Lys His Ala Gly Ile Thr Arg
                20                  25                  30

His Tyr Lys Phe Asp Ile Lys Leu Gln Asn Val Thr Arg Leu Cys Arg
            35                  40                  45

Thr Lys Ser Ile Val Thr Val Asn Gly Gln Ile Pro Gly Pro Arg Ile
        50                  55                  60

Ile Ala Arg Glu Gly Asp Arg Leu Leu Ile Lys Val Val Asn His Val
65                  70                  75                  80

Gln Tyr Asn Val Thr Leu His Trp His Gly Ile Arg Gln Leu Arg Ser
                85                  90                  95

Gly Trp Ala Asp Gly Pro Ala Tyr Val Thr Gln Cys Pro Ile Gln Thr
            100                 105                 110

Gly Gln Ser Tyr Val Tyr Asn Phe Thr Val Thr Gly Gln Arg Gly Thr
        115                 120                 125

Leu Phe Trp His Ala His Ile Ser Trp Leu Arg Ala Thr Leu Tyr Gly
130                 135                 140

Pro Ile Val Ile Leu Pro Lys Lys Gly Val Ser Tyr Pro Phe Pro Leu
145                 150                 155                 160

Pro His Lys Glu Val Pro Ile Ile Phe Gly Glu Trp Trp Lys Ala Asp
                165                 170                 175

Thr Glu Lys Ile Ile Ser Gln Ala Leu Lys Thr Gly Gly Ala Pro Asn
            180                 185                 190

Ile Ser Asp Ala Tyr Thr Ile Asn Gly His Pro Gly Leu Leu Tyr Asn
        195                 200                 205

Cys Ser Ala Lys Asp Thr Phe Lys Leu Lys Val Lys Pro Gly Lys Thr
210                 215                 220

Tyr Leu Leu Arg Leu Ile Asn Ala Ala Leu Asn Asp Glu Leu Phe Phe
225                 230                 235                 240

Ser Ile Ala Asn His Ser Leu Thr Val Val Glu Ala Asp Ala Val Tyr
                245                 250                 255

Val Lys Pro Phe Lys Thr His Ile Val Leu Ile Thr Pro Gly Gln Thr
            260                 265                 270

Thr Asn Val Leu Leu Met Ala Lys Ala Lys Ala Pro Asn Ser Thr Phe
        275                 280                 285

Leu Met Ala Ala Arg Pro Tyr Ala Thr Gly Pro Gly Ser Phe Asp Asn
```

```
            290                 295                 300
Thr Thr Thr Ala Gly Ile Leu Glu Tyr Asp Gln Asn Pro Ser Ala Thr
305                 310                 315                 320

Asn Ser Lys Ser Lys Asn Lys Lys Leu Pro Leu Leu Lys Pro Ser Leu
                325                 330                 335

Pro Val Phe Asn Asp Thr Thr Phe Ala Thr Lys Phe Val Lys Lys Ile
            340                 345                 350

Arg Ser Leu Ala Asn Ala Arg Phe Pro Ala Lys Val Pro Lys Lys Val
        355                 360                 365

Asp Arg Arg Phe Phe Phe Thr Ile Gly Leu Gly Ser Leu Pro Cys Ser
    370                 375                 380

Gln Asn Lys Thr Cys Gln Gly Pro Asn Asn Thr Met Phe Ala Ala Ser
385                 390                 395                 400

Val Asn Asn Val Ser Phe Val Gln Pro Asn Ile Ala Leu Leu Gln Ser
                405                 410                 415

His Phe Leu Asn Arg Ser Lys Gly Val Tyr Thr Thr Asp Phe Pro Thr
            420                 425                 430

Asn Pro Pro Phe Lys Phe Asn Tyr Thr Gly Thr Pro Pro Ser Asn Thr
        435                 440                 445

Met Thr Ala Lys Gly Thr Lys Val Val Val Leu Pro Phe Asn Thr Ser
    450                 455                 460

Val Glu Leu Val Met Gln Asp Thr Ser Ile Ile Gly Ala Glu Ser His
465                 470                 475                 480

Pro Leu His Leu His Gly Phe Asn Phe Phe Val Val Gly Gln Gly Phe
                485                 490                 495

Gly Asn Phe Asp Pro Lys Lys Asp Pro Val Lys Phe Asn Leu Val Asp
            500                 505                 510

Pro Ala Glu Arg Asn Thr Val Gly Val Pro Ser Gly Gly Trp Val Ala
        515                 520                 525

Ile Arg Phe Leu Ala Asp Asn Pro Gly Val Trp Phe Met His Cys His
    530                 535                 540

Leu Glu Val His Thr Ser Trp Gly Leu Lys Met Ala Trp Val Val Asn
545                 550                 555                 560

Asp Gly Lys Arg Pro Ser Gln Lys Leu Pro Pro Pro Ser Asp Leu
                565                 570                 575

Pro Lys Cys

<210> SEQ ID NO 20
<211> LENGTH: 580
<212> TYPE: PRT
<213> ORGANISM: Populus trichocarpa

<400> SEQUENCE: 20

Met Gly Ala Ser Ile Leu Pro Pro Ala Phe Arg Ala Leu Leu Phe
1               5                   10                  15

Ser Phe Ser Ile Phe Cys Leu Leu Pro Glu His Ala Phe Ala Val Thr
                20                  25                  30

Arg His Tyr Lys Phe Asp Ile Lys Leu Gln Asn Val Thr Arg Leu Cys
            35                  40                  45

His Ser Lys Ser Met Val Thr Val Asn Gly Gln Phe Pro Gly Pro Arg
        50                  55                  60

Ile Val Ala Arg Glu Gly Asp Asn Leu Phe Ile Lys Val Val Asn His
65                  70                  75                  80

Val Gln Asn Asn Ile Ser Ile His Trp His Gly Ile Arg Gln Leu Gln
```

-continued

```
                      85                  90                  95
Ser Gly Trp Ala Asp Gly Pro Ala Tyr Ile Thr Gln Cys Pro Ile Gln
                100                 105                 110

Thr Gly Gln Ser Tyr Val Tyr Asn Tyr Thr Ile Val Gly Gln Arg Gly
                115                 120                 125

Thr Leu Trp Trp His Ala His Ile Ser Trp Leu Arg Ser Thr Val Tyr
            130                 135                 140

Gly Pro Leu Ile Ile Leu Pro Lys Arg Gly Val Gln Tyr Pro Phe Ala
145                 150                 155                 160

Lys Pro Tyr Lys Glu Val Pro Ile Ile Phe Gly Glu Trp Phe Asn Val
                165                 170                 175

Asp Pro Glu Ala Val Ile Ser Gln Ala Leu Gln Thr Gly Gly Gly Pro
                180                 185                 190

Asn Val Ser Asp Ala Tyr Thr Ile Asn Gly Leu Pro Gly Pro Leu Tyr
            195                 200                 205

Asn Cys Ser Ala Glu Asp Thr Phe Lys Leu Lys Val Lys Pro Gly Lys
        210                 215                 220

Thr Tyr Met Leu Arg Leu Ile Asn Ala Ala Leu Asn Asp Glu Leu Phe
225                 230                 235                 240

Phe Ser Ile Ala Asn His Ser Val Thr Ile Val Asp Val Asp Ala Val
                245                 250                 255

Tyr Val Lys Pro Phe Asp Thr Glu Thr Leu Leu Ile Thr Pro Gly Gln
                260                 265                 270

Thr Thr Asn Val Leu Leu Lys Thr Lys Pro Tyr Phe Pro Asn Ala Thr
            275                 280                 285

Phe Phe Met Thr Ala Arg Pro Tyr Ala Thr Gly Gln Gly Thr Phe Asp
        290                 295                 300

Asn Ser Thr Val Ala Ala Ile Leu Glu Tyr Glu Ser Pro Lys Thr Ile
305                 310                 315                 320

His Ser Ser Gln Leu Ser Leu Lys Asn Leu Pro Leu Phe Lys Pro Thr
                325                 330                 335

Leu Pro Pro Leu Asn Asp Thr Ala Phe Ala Ala Asn Phe Thr Ser Lys
                340                 345                 350

Leu Arg Ser Leu Ala Ser Ala Gln Phe Pro Ala Lys Val Pro Gln Lys
            355                 360                 365

Val Asp Met Arg Phe Phe Phe Thr Val Gly Leu Gly Thr Asn Pro Cys
        370                 375                 380

Pro Lys Asn Gln Thr Cys Gln Gly Pro Asn Gly Thr Lys Phe Ala Ala
385                 390                 395                 400

Ser Val Asn Asn Val Ser Phe Ser Leu Pro Thr Thr Ala Leu Leu Gln
                405                 410                 415

Ala His Phe Phe Gly Lys Ser Asn Gly Val Tyr Ile Pro Asp Phe Pro
            420                 425                 430

Ile Thr Pro Ile Phe Pro Phe Asn Tyr Thr Gly Asn Pro Pro Asn Asn
        435                 440                 445

Thr Met Val Ser Thr Gly Thr Arg Leu Val Val Leu Pro Phe Asn Thr
    450                 455                 460

Ser Val Glu Leu Ile Met Gln Asp Thr Ser Ile Leu Gly Val Glu Ser
465                 470                 475                 480

His Pro Leu His Leu His Gly Tyr Asn Phe Phe Val Val Gly Gln Gly
                485                 490                 495

Phe Gly Asn Phe Asp Pro Asn Lys Asp Pro Ala Lys Phe Asn Leu Val
            500                 505                 510
```

-continued

Asp Pro Val Glu Arg Asn Thr Val Gly Val Pro Ser Gly Gly Trp Ala
            515                 520                 525

Ala Ile Arg Phe Gln Ala Asp Asn Pro Gly Val Trp Phe Met His Cys
    530                 535                 540

His Leu Glu Val His Thr Ser Trp Gly Leu Glu Met Ala Trp Val Val
545                 550                 555                 560

Leu Asp Gly Lys Leu Pro Asn Gln Lys Leu Ile Pro Pro Ala Asp
                565                 570                 575

Leu Pro Lys Cys
            580

<210> SEQ ID NO 21
<211> LENGTH: 581
<212> TYPE: PRT
<213> ORGANISM: Populus trichocarpa

<400> SEQUENCE: 21

Met Gly Val Ser Phe Leu Pro Ser Pro Ala Phe Leu Gly Leu Leu Leu
1               5                   10                  15

Phe Ser Phe Val Thr Leu Ser Leu His Pro Lys Pro Ala Val Ala Thr
            20                  25                  30

Thr Arg His Tyr Lys Leu Asp Val Met Leu Gln Asn Val Thr Arg Leu
        35                  40                  45

Cys His Thr Lys Ser Met Val Thr Val Asn Gly Lys Phe Pro Gly Pro
    50                  55                  60

Arg Ile Val Ala Arg Glu Gly Asp Arg Leu Leu Ile Lys Val Val Asn
65                  70                  75                  80

His Val Gln Asn Asn Ile Ser Ile His Trp His Gly Ile Arg Gln Leu
                85                  90                  95

Arg Ser Gly Trp Ala Asp Gly Pro Ala Tyr Val Thr Gln Cys Pro Ile
            100                 105                 110

Gln Thr Gly Gln Ser Tyr Val Tyr Asn Tyr Thr Ile Val Gly Gln Arg
        115                 120                 125

Gly Thr Leu Trp Trp His Ala His Ile Ser Trp Leu Arg Ser Thr Leu
    130                 135                 140

Tyr Gly Pro Leu Ile Ile Leu Pro Lys Leu Gly Thr Pro Tyr Pro Phe
145                 150                 155                 160

Val Lys Pro Tyr Lys Glu Val Pro Ile Ile Phe Gly Glu Trp Phe Asn
                165                 170                 175

Ala Asp Pro Glu Ala Ile Ile Asn Gln Ala Leu Gln Thr Gly Gly Gly
            180                 185                 190

Pro Asn Val Ser Asp Ala Tyr Thr Ile Asn Gly Leu Pro Gly Pro Leu
        195                 200                 205

Tyr Asn Cys Ser Ala Lys Asp Thr Phe Lys Leu Lys Val Lys Pro Gly
    210                 215                 220

Lys Thr Tyr Leu Leu Arg Leu Ile Asn Ala Ala Leu Asn Asp Glu Leu
225                 230                 235                 240

Phe Phe Ser Ile Ala Asn His Thr Phe Thr Val Val Glu Ala Asp Ala
                245                 250                 255

Val Tyr Val Lys Pro Phe Asp Thr Lys Thr Leu Leu Ile Ala Pro Gly
            260                 265                 270

Gln Thr Thr Asn Val Leu Leu Lys Thr Lys Pro His His Pro Asn Ala
        275                 280                 285

Lys Phe Phe Met Thr Ala Arg Pro Tyr Val Thr Gly Gln Gly Thr Phe

```
                    290                 295                 300
Asp Asn Ser Thr Val Ala Gly Ile Leu Glu Tyr Glu Ser His Lys
305                 310                 315                 320

Thr Ile Gln Ser Ser His Ser Thr Lys Arg Leu Pro Leu Phe Lys Pro
                325                 330                 335

Asn Leu Pro Pro Leu Asn Asp Thr Ser Phe Ala Thr Lys Phe Thr Ser
            340                 345                 350

Lys Leu Arg Ser Leu Ala Asn Ala Gln Phe Pro Ala Asn Val Pro Gln
        355                 360                 365

Lys Val Asp Arg Gln Phe Phe Phe Thr Val Gly Leu Gly Thr His Ser
    370                 375                 380

Cys Pro Gln Asn Gln Thr Cys Gln Gly Pro Asn Gly Thr Met Phe Ala
385                 390                 395                 400

Ala Ser Val Asn Asn Val Ser Phe Ala Met Pro Thr Thr Ala Leu Leu
                405                 410                 415

Gln Ala His His Phe Gly Gln Ser Asn Gly Val Tyr Thr Pro Asp Phe
            420                 425                 430

Pro Ile Asn Pro Leu Thr Pro Phe Asn Tyr Thr Gly Asn Pro Pro Asn
        435                 440                 445

Asn Thr Met Val Ser Asn Gly Thr Lys Leu Val Leu Pro Phe Asn
    450                 455                 460

Thr Thr Val Glu Leu Ile Met Gln Asp Thr Ser Ile Leu Gly Ala Glu
465                 470                 475                 480

Ser His Pro Leu His Leu His Gly Phe Asn Phe Val Val Gly Gln
                485                 490                 495

Gly Phe Gly Asn Phe Asp Pro Asn Lys Asp Pro Ala Asn Phe Asn Leu
            500                 505                 510

Ile Asp Pro Ile Glu Arg Asn Thr Val Gly Val Pro Ser Gly Gly Trp
        515                 520                 525

Val Ala Ile Arg Phe Leu Ala Asp Asn Pro Gly Val Trp Phe Met His
    530                 535                 540

Cys His Leu Glu Val His Thr Ser Trp Gly Leu Lys Met Ala Trp Val
545                 550                 555                 560

Val Leu Asp Gly Lys Leu Pro Asn Gln Lys Leu Pro Pro Ala
                565                 570                 575

Asp Leu Pro Arg Cys
            580

<210> SEQ ID NO 22
<211> LENGTH: 581
<212> TYPE: PRT
<213> ORGANISM: Populus trichocarpa

<400> SEQUENCE: 22

Met Gly Ala Ser Phe Leu Pro Ser Pro Ala Phe Leu Ala Val Phe Leu
1               5                   10                  15

Ile Ser Phe Val Thr Leu Ser Ile His Pro Glu Pro Ala Leu Ala Ile
                20                  25                  30

Thr Arg His Tyr Lys Phe Asp Val Met Leu Gln Asn Val Thr Arg Leu
            35                  40                  45

Cys His Thr Lys Ser Ile Val Thr Val Asn Gly Lys Phe Pro Gly Pro
        50                  55                  60

Arg Ile Val Ala Arg Glu Gly Asp Arg Leu Leu Ile Lys Val Val Asn
65                  70                  75                  80
```

-continued

```
His Val Gln Asn Asn Ile Ser Ile His Trp His Gly Ile Arg Gln Leu
                85                  90                  95

Arg Ser Gly Trp Ala Asp Gly Pro Ala Tyr Ile Thr Gln Cys Pro Ile
            100                 105                 110

Gln Thr Gly Gln Ser Tyr Val Tyr Asn Tyr Thr Ile Val Gly Gln Arg
        115                 120                 125

Gly Thr Leu Trp Trp His Ala His Ile Ser Trp Leu Arg Ser Thr Leu
    130                 135                 140

Tyr Gly Pro Leu Ile Ile Leu Pro Lys Leu Gly Thr Thr Tyr Pro Phe
145                 150                 155                 160

Ala Lys Pro His Lys Glu Val Pro Ile Ile Phe Gly Glu Trp Phe Asn
                165                 170                 175

Ala Asp Pro Glu Ala Ile Ile Asn Gln Ala Met Gln Thr Gly Gly Gly
            180                 185                 190

Pro Asn Val Ser Asp Ala Tyr Thr Ile Asn Gly Phe Pro Gly Pro Leu
        195                 200                 205

Tyr Asn Cys Ser Ala Lys Asp Thr Phe Lys Leu Lys Val Lys Pro Gly
    210                 215                 220

Lys Thr Tyr Leu Leu Arg Met Ile Asn Ala Ala Leu Asn Asp Glu Leu
225                 230                 235                 240

Phe Phe Ser Ile Ala Asn His Thr Leu Thr Val Val Asp Val Asp Ala
                245                 250                 255

Ile Tyr Val Lys Pro Phe Asp Thr Glu Thr Leu Leu Ile Ala Pro Gly
            260                 265                 270

Gln Thr Thr Asn Val Leu Leu Lys Thr Lys Pro His His Pro Asn Ala
        275                 280                 285

Ser Phe Phe Met Ser Ala Arg Pro Tyr Val Thr Gly Gln Gly Thr Phe
    290                 295                 300

Asp Asn Ser Thr Val Ala Gly Ile Leu Glu Tyr Glu Glu Ser Asn Lys
305                 310                 315                 320

Thr Ile Lys Ser Ser His Ser Pro Lys Lys Leu Pro Phe Tyr Lys Pro
                325                 330                 335

Asn Leu Pro Pro Leu Asn Asp Thr Ser Phe Ala Thr Asn Phe Thr Ser
            340                 345                 350

Lys Leu Arg Ser Leu Ala Ser Ala Glu Phe Pro Ala Asn Val Pro Gln
        355                 360                 365

Lys Val Asp Arg Gln Phe Phe Phe Ser Val Ser Leu Gly Thr Asn Pro
    370                 375                 380

Cys Ser Lys Asn Lys Thr Cys Gln Gly Pro Asn Gly Thr Met Phe Ala
385                 390                 395                 400

Ala Ser Val Asn Asn Val Ser Phe Val Met Pro Thr Lys Ala Leu Leu
                405                 410                 415

Gln Ala His His Phe Gly Gln Ser Lys Gly Val Tyr Ser Pro Asn Phe
            420                 425                 430

Pro Ile Asn Pro Leu Ile Pro Phe Asn Tyr Thr Gly Thr Pro Pro Asn
        435                 440                 445

Asn Thr Met Val Ser Asn Gly Thr Lys Leu Val Val Leu Pro Phe Asn
    450                 455                 460

Thr Ser Val Glu Leu Ile Met Gln Asp Thr Ser Ile Leu Gly Ala Glu
465                 470                 475                 480

Ser His Pro Leu His Leu His Gly Phe Asn Phe Phe Val Val Gly Glu
                485                 490                 495

Gly Phe Gly Asn Phe Asp Pro Lys Lys Asp Pro Ala Asn Phe Asn Leu
```

-continued

```
                500                 505                 510
Val Asp Pro Val Glu Arg Asn Thr Val Gly Val Pro Ser Gly Gly Trp
            515                 520                 525

Val Ala Ile Arg Phe Leu Ala Asp Asn Pro Gly Val Trp Phe Met His
        530                 535                 540

Cys His Leu Glu Val His Thr Ser Trp Gly Leu Lys Met Ala Trp Val
545                 550                 555                 560

Val Leu Asp Gly Lys Leu Pro Asn Gln Lys Leu Leu Pro Pro Pro Ala
                565                 570                 575

Asp Leu Pro Lys Cys
            580

<210> SEQ ID NO 23
<211> LENGTH: 580
<212> TYPE: PRT
<213> ORGANISM: Populus trichocarpa

<400> SEQUENCE: 23

Met Gly Asn Ser Pro Arg Ser Thr Val Leu Pro Ser Met Ala Ala Leu
1               5                   10                  15

Gln Leu Leu Cys Phe Phe Phe Ser Leu Val Pro Asp Phe Ala Ala
            20                  25                  30

Ala Ile Thr Arg Gln Tyr Thr Phe Asn Ile Thr His Lys Asn Phe Thr
        35                  40                  45

Arg Leu Cys His Thr Arg Ser Leu Val Thr Val Asn Gly Gln Phe Pro
    50                  55                  60

Gly Pro Arg Leu Val Ala Arg Glu Gly Asp Gln Val Leu Val Lys Val
65                  70                  75                  80

Val Asn His Val Ala Glu Asn Ile Thr Ile His Trp His Gly Val Arg
                85                  90                  95

Gln Leu Thr Ser Gly Trp Ala Asp Gly Pro Ala Tyr Val Thr Gln Cys
            100                 105                 110

Pro Ile Gln Thr Gly Gln Ala Tyr Thr Tyr Asn Phe Thr Ile Thr Gly
        115                 120                 125

Gln Arg Gly Thr Leu Leu Trp His Ala His Ile Ser Trp Leu Arg Ser
    130                 135                 140

Ser Leu Tyr Gly Pro Ile Ile Ile Leu Pro Lys Leu Asn Glu Ser Tyr
145                 150                 155                 160

Pro Phe Lys Lys Pro Tyr Lys Glu Ile Pro Ile Leu Phe Gly Glu Trp
                165                 170                 175

Phe Asn Val Asp Pro Glu Ala Val Ile Ala Gln Ala Leu Gln Thr Gly
            180                 185                 190

Ala Gly Pro Asn Val Ser Asp Ala Tyr Thr Ile Asn Gly Leu Pro Gly
        195                 200                 205

Pro Leu Tyr Asn Cys Ser Ala Lys Asp Thr Tyr Lys Leu Lys Val Lys
    210                 215                 220

Pro Gly Lys Thr Tyr Leu Leu Arg Leu Ile Asn Ala Ala Leu Asn Asp
225                 230                 235                 240

Glu Leu Phe Phe Ser Ile Ala Asn His Thr Leu Thr Val Val Glu Ala
                245                 250                 255

Asp Ala Val Tyr Val Lys Pro Phe Glu Ala Asp Thr Leu Leu Ile Ser
            260                 265                 270

Pro Gly Gln Thr Thr Asn Val Leu Leu Lys Thr Lys Pro His Leu Pro
        275                 280                 285
```

Asn Ala Thr Phe Tyr Met Phe Ala Gly Pro Tyr Phe Ser Gly Met Gly
    290                 295                 300

Ser Phe Asp Asn Ser Thr Thr Ala Gly Val Leu Val Tyr Lys His Pro
305                 310                 315                 320

Ser Ser Asn Asn His Leu Lys Lys Leu Pro Thr Leu Lys Pro Thr Leu
                325                 330                 335

Pro Pro Ile Asn Ala Thr Gly Phe Val Ala Asn Phe Thr Lys Lys Phe
            340                 345                 350

Arg Ser Leu Ala Asn Ala Lys Phe Pro Ala Asn Val Pro Gln Thr Val
        355                 360                 365

Asp Arg Lys Phe Phe Phe Thr Val Gly Leu Gly Thr Asn Pro Cys Pro
370                 375                 380

Lys Asn Thr Thr Cys Gln Gly Pro Asn Asn Thr Lys Phe Ala Ala
385                 390                 395                 400

Ser Ile Asn Asn Val Ser Phe Val Leu Pro Ser Val Ala Leu Leu Gln
                405                 410                 415

Ser Tyr Phe Phe Gly Gln Ser Asn Gly Val Phe Thr Ser Asp Phe Pro
            420                 425                 430

Gln Asn Pro Thr Ile Pro Phe Asn Tyr Thr Gly Thr Pro Asn Asn
        435                 440                 445

Thr Met Val Ser Asn Gly Thr Lys Ala Val Val Leu Thr Phe Asn Thr
450                 455                 460

Ser Val Glu Leu Val Met Gln Gly Thr Ser Ile Val Ala Ala Glu Ser
465                 470                 475                 480

His Pro Leu His Leu His Gly Phe Asn Phe Phe Val Val Gly Gln Gly
                485                 490                 495

Phe Gly Asn Tyr Asp Pro Asn Lys Asp Pro Ser Asn Phe Asn Leu Val
            500                 505                 510

Asp Pro Met Glu Arg Asn Thr Ala Gly Val Pro Ala Gly Gly Trp Ile
        515                 520                 525

Ala Ile Arg Phe Leu Ala Asp Asn Pro Gly Val Trp Phe Met His Cys
530                 535                 540

His Leu Asp Val His Thr Ser Trp Gly Leu Arg Met Ala Trp Ile Val
545                 550                 555                 560

Leu Asp Gly Pro Gln Pro Asn Gln Lys Ile Pro Pro Pro Ser Asp
                565                 570                 575

Leu Pro Lys Cys
            580

<210> SEQ ID NO 24
<211> LENGTH: 576
<212> TYPE: PRT
<213> ORGANISM: Populus trichocarpa

<400> SEQUENCE: 24

Met Gly Ala Ser Val Pro Ala Ser Pro Glu Ile Leu Leu Thr Ile Leu
1               5                   10                  15

Leu Phe Ala Met Ser Cys Leu Trp Ala Phe Pro Glu Val Ala Gly Ala
            20                  25                  30

Lys His Ala Gly Ile Thr Arg His Tyr Lys Phe Asn Ile Lys Leu Thr
        35                  40                  45

Asn Val Thr Arg Leu Cys His Thr Lys Ser Met Val Thr Val Asn Gly
    50                  55                  60

Lys Phe Pro Gly Pro Arg Val Val Ala Arg Glu Gly Asp Arg Leu Val
65                  70                  75                  80

Val Lys Val Val Asn His Val Pro Asn Asn Ile Ser Ile His Trp His
                85                  90                  95

Gly Ile Arg Gln Leu Gln Ser Gly Trp Ala Asp Gly Pro Ala Tyr Ile
                100                 105                 110

Thr Gln Cys Pro Ile Gln Thr Asn Gln Thr Tyr Val Tyr Asn Phe Thr
                115                 120                 125

Ile Thr Gly Gln Arg Gly Thr Leu Phe Trp His Ala His Leu Ser Trp
            130                 135                 140

Leu Arg Ala Ser Val Tyr Gly Pro Leu Ile Ile Leu Pro Lys Arg Asn
145                 150                 155                 160

Val Ser Tyr Pro Phe Ala Lys Pro His Lys Glu Val Thr Ile Met Leu
                165                 170                 175

Gly Glu Trp Phe Asn Ala Asp Thr Glu Ala Val Ile Ser Gln Ala Leu
                180                 185                 190

Gln Thr Gly Gly Gly Pro Asn Val Ser Glu Ala Tyr Thr Phe Asn Gly
                195                 200                 205

Leu Pro Gly Pro Leu Tyr Asn Cys Ser Glu Asn Asn Thr Tyr Lys Leu
            210                 215                 220

Lys Val Lys Pro Gly Lys Thr Tyr Leu Leu Arg Leu Ile Asn Ala Ala
225                 230                 235                 240

Leu Asn Asp Asp Leu Phe Phe Ser Ile Ala Asn His Thr Phe Thr Val
                245                 250                 255

Val Glu Val Asp Ala Thr Tyr Ala Lys Pro Phe Glu Thr Asn Leu Leu
                260                 265                 270

Val Ile Thr Ala Gly Gln Thr Asn Val Leu Leu Lys Ala Lys Pro
                275                 280                 285

Ile Ala Pro Asn Ala Ser Phe Tyr Met Leu Ala Arg Pro Tyr Phe Thr
            290                 295                 300

Gly Gln Gly Thr Phe Asp Asn Thr Thr Val Ala Gly Ile Leu Glu Tyr
305                 310                 315                 320

Glu Thr Ser Ser Asn Ser Thr Ala Phe Lys Pro Thr Leu Pro Pro Ile
                325                 330                 335

Asn Ala Thr Asn Val Val Ala Asn Phe Thr Arg Arg Leu Arg Ser Leu
                340                 345                 350

Ala Asn Ser Arg Phe Pro Val Asn Val Pro Gln Thr Val Asp Lys Lys
            355                 360                 365

Phe Phe Phe Thr Val Gly Leu Gly Asn Ser Pro Cys Pro Lys Asn Gln
370                 375                 380

Thr Cys Gln Gly Pro Asn Gly Thr Lys Phe Ser Ala Ser Val Asn Asn
385                 390                 395                 400

Ile Ser Met Ala Leu Pro Ser Ser Ala Leu Leu Gln Ser Tyr Phe Phe
                405                 410                 415

Lys Lys Ser Asn Gly Val Tyr Thr Ser Asp Phe Pro Ser Phe Pro Leu
            420                 425                 430

His Pro Phe Asn Tyr Thr Gly Thr Pro Pro Asn Asn Thr Leu Val Ala
    435                 440                 445

Asn Gly Thr Lys Leu Val Val Val Pro Phe Asn Thr Ser Val Glu Val
450                 455                 460

Val Met Gln Gly Thr Arg Ile Phe Gly Ala Glu Ser His Pro Leu His
465                 470                 475                 480

Leu His Gly Phe Asn Phe Tyr Val Val Gly Glu Gly Phe Gly Asn Phe
                485                 490                 495

```
Asp Pro Asn Asn Asp Pro Lys Asn Phe Asn Leu Val Asp Pro Val Glu
            500                 505                 510

Arg Asn Thr Val Gly Val Pro Thr Ala Gly Trp Val Ala Ile Arg Phe
            515                 520                 525

His Ala Asp Asn Pro Gly Val Trp Phe Met His Cys His Phe Asp Val
            530                 535                 540

His Leu Ser Trp Gly Leu Arg Met Ala Trp Ile Val Leu Asp Gly Thr
545                 550                 555                 560

Leu Pro Ser Gln Lys Leu Pro Pro Pro Ser Asp Leu Pro Lys Cys
            565                 570                 575

<210> SEQ ID NO 25
<211> LENGTH: 581
<212> TYPE: PRT
<213> ORGANISM: Populus trichocarpa

<400> SEQUENCE: 25

Met Gly Val Tyr Leu Leu Pro Ser Pro Ala Ser Leu Ala Val Phe Leu
1               5                   10                  15

Ser Ser Phe Val Thr Leu Phe Val His Pro Arg Pro Ala Ile Ala Ile
                20                  25                  30

Thr Arg His Tyr Lys Phe Asp Val Leu Leu Gln Asn Val Thr Arg Leu
            35                  40                  45

Cys His Thr Lys Ser Met Val Thr Val Asn Ala Lys Phe Pro Gly Pro
50                  55                  60

Cys Ile Val Ala Arg Glu Gly Asp Arg Leu Leu Ile Lys Val Val Asn
65                  70                  75                  80

His Val Gln Asn Asn Ile Ser Ile His Trp His Gly Ile Arg Gln Leu
                85                  90                  95

Arg Ser Gly Trp Ala Asp Gly Pro Ala Tyr Val Thr Gln Cys Pro Ile
            100                 105                 110

Gln Thr Gly Gln Ser Tyr Val Tyr Asn Tyr Thr Ile Val Gly Gln Arg
            115                 120                 125

Gly Thr Leu Trp Trp His Ala His Ile Ser Trp Leu Arg Ser Thr Leu
130                 135                 140

Tyr Gly Pro Leu Ile Ile Leu Pro Lys Leu Gly Thr Pro Tyr Pro Phe
145                 150                 155                 160

Ala Lys Pro Asp Lys Glu Val Pro Ile Ile Phe Gly Glu Trp Phe Asn
                165                 170                 175

Ala Asp Pro Glu Ala Ile Ile Asn Gln Ala Met Gln Thr Gly Gly Gly
            180                 185                 190

Pro Asn Val Ser Asp Ala Tyr Thr Ile Asn Gly Leu Pro Gly Pro Leu
            195                 200                 205

Tyr Asn Cys Ser Ala Lys Asn Thr Phe Lys Leu Lys Val Lys Pro Gly
210                 215                 220

Lys Thr Tyr Leu Leu Arg Leu Ile Asn Ala Ala Leu Asn Glu Glu Leu
225                 230                 235                 240

Phe Phe Ser Ile Ala Asn His Thr Leu Thr Val Val Gly Val Asp Ala
                245                 250                 255

Ile Tyr Val Lys Pro Phe Asp Thr Glu Thr Leu Leu Ile Ala Ser Gly
            260                 265                 270

Gln Thr Thr Asp Val Leu Leu Lys Thr Lys Pro His His Pro Asp Ala
            275                 280                 285

Lys Phe Phe Met Ser Ala Arg Pro Tyr Val Thr Gly Gln Gly Thr Phe
            290                 295                 300
```

```
Asp Asn Ser Thr Val Ala Gly Ile Leu Glu Tyr Glu Val Ala Arg Lys
305                 310                 315                 320

Thr Ile Gln Ser Ser His Thr Ser Lys Arg Leu Pro Leu Tyr Lys Pro
            325                 330                 335

Asn Leu Pro Pro Leu Asn Asp Thr Ser Phe Ala Thr Asn Phe Thr Ser
        340                 345                 350

Lys Leu Arg Ser Leu Ala Ser Ala Glu Phe Pro Ala Asn Val Pro Gln
    355                 360                 365

Lys Val Asp Arg His Phe Phe Phe Thr Val Gly Leu Gly Thr Asn Pro
370                 375                 380

Cys Ser Lys Asn Gln Thr Cys Gln Gly Pro Asn Gly Thr Arg Phe Ala
385                 390                 395                 400

Ala Ser Val Asn Val Ser Phe Val Met Pro Thr Lys Ala Leu Leu
                405                 410                 415

Glu Ala His His Phe Gly Gln Ser Lys Gly Val Tyr Ser Pro Asn Phe
                420                 425                 430

Pro Ile Ser Pro Leu Ile Pro Phe Asp Tyr Thr Gly Thr Pro Gln Asn
            435                 440                 445

Asn Thr Met Val Ser His Gly Thr Lys Leu Val Met Leu Pro Phe Asn
        450                 455                 460

Thr Ser Val Glu Leu Ile Met Gln Asp Thr Ser Ile Leu Gly Ala Glu
465                 470                 475                 480

Ser His Pro Leu His Leu His Gly Phe Asn Phe Val Val Gly Gln
                485                 490                 495

Gly Phe Gly Asn Phe Asp Pro Lys Lys Asp Pro Ala Asn Phe Asn Leu
            500                 505                 510

Val Asp Pro Val Glu Arg Asn Thr Val Gly Val Pro Ser Gly Gly Trp
        515                 520                 525

Val Ala Ile Arg Phe Leu Ala Asp Asn Pro Gly Val Trp Phe Leu His
    530                 535                 540

Cys His Val Glu Leu His Met Ser Trp Gly Leu Met Met Ala Trp Val
545                 550                 555                 560

Val Leu Asp Gly Lys Leu Pro Asn His Arg Leu Leu Pro Pro Val
                565                 570                 575

Asp Leu Pro Lys Cys
            580

<210> SEQ ID NO 26
<211> LENGTH: 576
<212> TYPE: PRT
<213> ORGANISM: Populus trichocarpa

<400> SEQUENCE: 26

Met Gly Ala Pro Val Pro Ala Ser Pro Gly Ile Leu Leu Thr Ile Leu
1               5                   10                  15

Leu Phe Ala Met Ser Cys Leu Trp Ala Phe Pro Glu Val Ala Gly Ala
            20                  25                  30

Lys His Ala Gly Ile Thr Arg His Tyr Lys Phe Asn Ile Lys Leu Thr
        35                  40                  45

Asn Val Thr Arg Leu Cys His Thr Lys Ser Met Val Thr Val Asn Gly
    50                  55                  60

Lys Phe Pro Gly Pro Arg Val Val Ala Arg Glu Gly Asp Arg Leu Val
65                  70                  75                  80

Val Lys Val Val Asn His Val Pro Asn Asn Ile Ser Ile His Trp His
```

```
                    85              90              95
Gly Ile Arg Gln Leu Gln Ser Gly Trp Ala Asp Gly Pro Ala Tyr Ile
            100             105             110

Thr Gln Cys Pro Ile Gln Thr Asn Gln Thr Tyr Val Tyr Asn Phe Thr
            115             120             125

Val Thr Gly Gln Arg Gly Thr Leu Phe Trp His Ala His Leu Ser Trp
    130             135             140

Leu Arg Ala Ser Val Tyr Gly Pro Leu Ile Ile Phe Pro Lys Arg Asn
145             150             155             160

Val Ser Tyr Pro Phe Ala Lys Pro His Lys Glu Val Thr Ile Met Leu
                165             170             175

Gly Glu Trp Phe Asn Ala Asp Pro Glu Ala Val Ile Arg Gln Ala Leu
            180             185             190

Gln Thr Gly Gly Gly Pro Asn Val Ser Glu Ala Tyr Thr Phe Asn Gly
        195             200             205

Leu Thr Gly Pro Leu Tyr Asn Cys Ser Ala Asn Asn Thr Tyr Lys Leu
    210             215             220

Lys Val Lys Pro Gly Lys Thr Tyr Leu Leu Arg Leu Ile Asn Ala Ala
225             230             235             240

Leu Asn Asp Glu Leu Phe Phe Ser Ile Ala Asn His Thr Phe Thr Val
                245             250             255

Val Glu Val Asp Ala Thr Tyr Val Lys Pro Phe Glu Thr Asn Leu Leu
        260             265             270

Val Ile Thr Pro Gly Gln Thr Thr Asn Val Leu Leu Lys Thr Lys Pro
    275             280             285

Ile Ala Pro Asn Ala Ser Phe Tyr Met Leu Ala Arg Pro Tyr Phe Thr
290             295             300

Gly Gln Gly Thr Phe Asp Asn Thr Thr Val Ala Gly Ile Leu Glu Tyr
305             310             315             320

Glu Thr Ser Ser Asn Ser Thr Thr Phe Lys Pro Thr Leu Pro Pro Ile
            325             330             335

Asn Ala Thr Asn Ala Val Ala Asn Phe Thr Arg Lys Leu Arg Ser Leu
            340             345             350

Ala Asn Phe Gln Phe Pro Val Asn Val Pro Gln Thr Val Asp Lys Lys
        355             360             365

Phe Phe Phe Thr Val Gly Leu Gly Asn Asn Pro Cys Pro Lys Asn Gln
    370             375             380

Thr Cys Gln Gly Pro Asn Gly Thr Lys Phe Ser Ala Ser Val Asn Asn
385             390             395             400

Ile Ser Met Ala Leu Pro Ser Thr Ala Leu Leu Gln Ser Tyr Phe Phe
                405             410             415

Lys Lys Ser Asn Gly Val Tyr Thr Ser Asp Phe Pro Ser Ser Pro Leu
        420             425             430

His Pro Phe Asn Tyr Thr Gly Thr Pro Pro Asn Asn Thr Phe Val Thr
    435             440             445

Asn Gly Thr Lys Leu Ile Val Leu Pro Phe Asn Thr Asn Val Glu Val
    450             455             460

Val Met Gln Gly Thr Ser Ile Leu Gly Ala Glu Ser His Pro Leu His
465             470             475             480

Leu His Gly Phe Asn Phe Tyr Val Val Gly Glu Gly Phe Gly Asn Phe
                485             490             495

Asp Pro Asn Asn Asp Pro Lys Asn Phe Asn Leu Val Asp Pro Val Glu
        500             505             510
```

```
Arg Asn Thr Val Gly Val Pro Ser Gly Gly Trp Val Ala Ile Arg Phe
            515                 520                 525

His Ala Asp Asn Pro Gly Val Trp Phe Met His Cys His Phe Asp Val
        530                 535                 540

His Leu Ser Trp Gly Leu Arg Met Ala Trp Ile Val Leu Asp Gly Thr
545                 550                 555                 560

Leu Pro Ser Gln Lys Leu Pro Pro Pro Ser Asp Leu Pro Lys Cys
            565                 570                 575

<210> SEQ ID NO 27
<211> LENGTH: 576
<212> TYPE: PRT
<213> ORGANISM: Populus trichocarpa

<400> SEQUENCE: 27

Met Gly Ala Ser Val Pro Ala Ser Pro Glu Ile Leu Thr Ile Leu
1               5                   10                  15

Leu Phe Ala Met Ser Cys Leu Trp Ala Phe Pro Glu Val Ala Gly Ala
            20                  25                  30

Lys His Ala Gly Ile Thr Arg His Tyr Lys Phe Asn Ile Lys Leu Lys
        35                  40                  45

Asn Val Thr Arg Leu Cys His Thr Lys Ser Met Val Thr Val Asn Gly
    50                  55                  60

Lys Phe Pro Gly Pro Arg Val Val Ala Arg Glu Gly Asp Arg Leu Val
65                  70                  75                  80

Val Lys Val Val Asn His Val Pro Asn Asn Ile Ser Ile His Trp His
                85                  90                  95

Gly Ile Arg Gln Leu Gln Ser Gly Trp Ala Asp Gly Pro Ala Tyr Ile
            100                 105                 110

Thr Gln Cys Pro Ile Gln Thr Asn Gln Thr Tyr Val Tyr Asn Phe Thr
        115                 120                 125

Val Thr Gly Gln Arg Gly Thr Leu Phe Trp His Ala His Leu Ser Trp
    130                 135                 140

Leu Arg Ala Ser Val Tyr Gly Pro Leu Ile Ile Leu Pro Lys Arg Asn
145                 150                 155                 160

Val Ser Tyr Pro Phe Ala Lys Pro His Lys Glu Val Thr Ile Met Leu
                165                 170                 175

Gly Glu Trp Phe Asn Ala Asp Thr Glu Ala Val Ile Ser Gln Ala Leu
            180                 185                 190

Gln Thr Gly Gly Gly Pro Asn Val Ser Glu Ala Tyr Thr Phe Asn Gly
        195                 200                 205

Leu Pro Gly Pro Leu Tyr Asn Cys Ser Glu Asn Asn Thr Tyr Lys Leu
    210                 215                 220

Lys Val Lys Pro Gly Lys Thr Tyr Leu Leu Arg Leu Ile Asn Ala Ala
225                 230                 235                 240

Leu Asn Asp Asp Leu Phe Phe Ser Ile Ala Asn His Thr Phe Thr Val
                245                 250                 255

Val Glu Val Asp Ala Thr Tyr Ala Lys Pro Phe Glu Thr Asn Leu Leu
            260                 265                 270

Val Ile Thr Ala Gly Gln Thr Thr Asn Val Leu Leu Lys Thr Lys Ser
        275                 280                 285

Ile Ala Pro Asn Ala Ser Phe Tyr Met Leu Ala Arg Pro Tyr Phe Thr
    290                 295                 300

Gly Gln Gly Thr Phe Asp Asn Thr Thr Val Ala Gly Ile Leu Glu Tyr
```

```
                305                 310                 315                 320
Glu Thr Ser Ser Asn Ser Thr Ala Phe Lys Ser Thr Leu Pro Pro Ile
                325                 330                 335
Asn Ala Thr Asn Val Val Ala Asn Phe Thr Arg Lys Leu Arg Ser Leu
                340                 345                 350
Ala Asn Ser Arg Phe Pro Val Asn Val Pro Gln Thr Val Asp Lys Lys
                355                 360                 365
Phe Phe Phe Thr Val Gly Leu Gly Asn Ser Pro Cys Pro Lys Asn Gln
                370                 375                 380
Thr Cys Gln Gly Pro Asn Gly Thr Lys Phe Ala Ala Ser Val Asn Asn
385                 390                 395                 400
Ile Ser Met Ala Leu Pro Ser Ser Ala Leu Leu Gln Ser Tyr Phe Phe
                405                 410                 415
Lys Lys Ser Asn Gly Val Tyr Thr Ser Asp Phe Pro Ser Phe Pro Leu
                420                 425                 430
His Pro Phe Asn Tyr Thr Gly Thr Pro Pro Asn Asn Thr Leu Val Thr
                435                 440                 445
Asn Gly Asn Lys Leu Val Val Pro Phe Asn Thr Ser Val Glu Val
450                 455                 460
Val Met Gln Gly Thr Arg Ile Phe Gly Ala Glu Ser His Pro Leu His
465                 470                 475                 480
Leu His Gly Phe Asn Phe Tyr Val Val Gly Glu Gly Phe Gly Asn Phe
                485                 490                 495
Asp Pro Asn Asn Asp Pro Lys Asn Phe Asn Leu Val Asp Pro Val Glu
                500                 505                 510
Arg Asn Thr Val Gly Val Pro Thr Ala Gly Trp Val Ala Ile Arg Phe
                515                 520                 525
Tyr Ala Asp Asn Pro Gly Val Trp Phe Met His Cys His Phe Asp Val
                530                 535                 540
His Leu Ser Trp Gly Leu Arg Met Ala Trp Ile Val Leu Asp Gly Thr
545                 550                 555                 560
Leu Pro Ser Gln Lys Leu Pro Pro Pro Ser Asp Leu Pro Lys Cys
                565                 570                 575

<210> SEQ ID NO 28
<211> LENGTH: 576
<212> TYPE: PRT
<213> ORGANISM: Populus trichocarpa

<400> SEQUENCE: 28

Met Gly Ala Ser Val Pro Ala Ser Pro Glu Ile Leu Leu Thr Ile Leu
1               5                   10                  15
Leu Phe Ala Met Ser Cys Leu Trp Ala Phe Pro Glu Val Ala Gly Ala
                20                  25                  30
Lys His Ala Gly Ile Thr Arg His Tyr Lys Phe Asn Ile Glu Leu Thr
                35                  40                  45
Asn Val Thr Arg Leu Cys His Thr Lys Ser Met Val Thr Val Asn Gly
                50                  55                  60
Lys Phe Pro Gly Pro Arg Val Val Ala Arg Glu Gly Asp Arg Leu Val
65                  70                  75                  80
Val Lys Val Val Asn His Val Pro Asn Asn Ile Ser Ile His Trp His
                85                  90                  95
Gly Ile Arg Gln Leu Gln Ser Gly Trp Ala Asp Gly Pro Ala Tyr Ile
                100                 105                 110
```

-continued

Thr Gln Cys Pro Ile Gln Thr Asn Gln Thr Tyr Val Tyr Asn Phe Thr
            115                 120                 125
Ile Thr Gly Gln Arg Gly Thr Leu Phe Trp His Ala His Leu Ser Trp
    130                 135                 140
Leu Arg Ala Ser Val Tyr Gly Pro Leu Ile Ile Leu Pro Lys Arg Asn
145                 150                 155                 160
Val Ser Tyr Pro Phe Ala Lys Pro His Lys Glu Val Thr Ile Met Leu
                165                 170                 175
Gly Glu Trp Phe Asn Ala Asp Thr Glu Ala Val Ile Ser Gln Ala Leu
            180                 185                 190
Gln Thr Gly Gly Gly Pro Asn Val Ser Glu Ala Tyr Thr Phe Asn Gly
        195                 200                 205
Leu Pro Gly Pro Leu Tyr Asn Cys Ser Glu Asn Asn Thr Tyr Lys Leu
    210                 215                 220
Lys Val Lys Pro Gly Lys Thr Tyr Leu Leu Arg Leu Ile Asn Val Ala
225                 230                 235                 240
Leu Asn Asp Asp Leu Phe Phe Ser Ile Ala Asn His Thr Phe Thr Val
                245                 250                 255
Val Glu Val Asp Ala Thr Tyr Ala Lys Pro Phe Glu Thr Asn Leu Leu
            260                 265                 270
Val Ile Thr Ala Gly Gln Thr Thr Asn Val Leu Leu Lys Thr Lys Pro
        275                 280                 285
Ile Ala Pro Asn Ala Ser Phe Tyr Met Leu Ala Arg Pro Tyr Phe Thr
    290                 295                 300
Gly Gln Gly Thr Phe Asp Asn Thr Thr Val Ala Gly Ile Leu Glu Tyr
305                 310                 315                 320
Glu Thr Ser Ser Asn Ser Thr Ala Phe Lys Pro Thr Leu Pro Pro Ile
                325                 330                 335
Asn Ala Thr Asn Val Val Ala Asn Phe Thr Arg Arg Leu Arg Ser Leu
            340                 345                 350
Ala Asn Ser Arg Phe Pro Val Asn Val Pro Gln Thr Ala Asp Lys Lys
        355                 360                 365
Phe Phe Phe Thr Val Gly Leu Gly Asn Ser Pro Cys Pro Lys Asn Gln
370                 375                 380
Thr Cys Gln Gly Pro Asn Gly Thr Lys Phe Ser Ala Ser Val Asn Asn
385                 390                 395                 400
Ile Ser Met Ala Leu Pro Ser Ser Ala Leu Leu Gln Ser Tyr Phe Phe
                405                 410                 415
Lys Lys Ser Asn Gly Val Tyr Thr Ser Asp Phe Pro Ser Phe Pro Leu
            420                 425                 430
His Pro Phe Asn Tyr Thr Gly Thr Pro Pro Asn Asn Thr Leu Val Ala
        435                 440                 445
Asn Gly Thr Lys Leu Val Val Pro Phe Asn Thr Ser Val Glu Val
450                 455                 460
Val Met Gln Gly Thr Arg Ile Phe Gly Ala Glu Ser His Pro Leu His
465                 470                 475                 480
Leu His Gly Phe Asn Phe Tyr Val Val Gly Glu Gly Phe Gly Asn Phe
                485                 490                 495
Asp Pro Asn Asn Asp Pro Lys Asn Phe Asn Leu Val Asp Pro Val Glu
            500                 505                 510
Arg Asn Thr Val Gly Val Pro Thr Ala Gly Trp Val Ala Ile Arg Phe
        515                 520                 525
His Ala Asp Asn Pro Gly Val Trp Phe Met His Cys His Phe Asp Val

```
                530                 535                 540
His Leu Ser Trp Gly Leu Arg Met Ala Trp Ile Val Leu Asp Gly Thr
545                 550                 555                 560

Leu Pro Ser Gln Lys Leu Pro Pro Pro Ser Asp Leu Pro Lys Cys
                565                 570                 575

<210> SEQ ID NO 29
<211> LENGTH: 581
<212> TYPE: PRT
<213> ORGANISM: Populus trichocarpa

<400> SEQUENCE: 29

Met Gly Ala Ser Leu Leu Pro Pro Ala Phe Leu Ala Val Phe Leu
1               5                   10                  15

Phe Ser Phe Val Thr Leu Ser Val Asn Pro Glu Pro Ala Leu Ala Ile
                20                  25                  30

Thr Arg His Tyr Lys Phe Asp Val Met Leu Gln Asn Val Thr Arg Leu
                35                  40                  45

Cys His Thr Arg Ser Met Val Thr Val Asn Gly Lys Phe Pro Gly Pro
        50                  55                  60

Arg Ile Val Ala Arg Glu Gly Asp Arg Leu Val Ile Arg Met Val Asn
65                  70                  75                  80

His Val Gln Asn Asn Ile Ser Ile His Trp His Gly Ile Arg Gln Leu
                    85                  90                  95

Arg Ser Gly Trp Ala Asp Gly Pro Ala Tyr Val Thr Gln Cys Pro Ile
                100                 105                 110

Gln Thr Gly Gln Ser Tyr Val Tyr Asn Tyr Thr Ile Val Gly Gln Arg
                115                 120                 125

Gly Thr Leu Trp Trp His Ala His Ile Ser Trp Leu Arg Ser Thr Leu
130                 135                 140

His Gly Pro Ile Ile Leu Pro Lys Leu Gly Thr Pro Tyr Pro Phe
145                 150                 155                 160

Ala Lys Pro Tyr Lys Glu Val Pro Ile Ile Phe Gly Glu Trp Phe Asn
                165                 170                 175

Ala Asp Pro Glu Ala Ile Ile Ser Gln Ala Met Gln Thr Gly Gly Gly
                180                 185                 190

Pro Asn Val Ser Asp Ala Tyr Thr Ile Asn Gly Leu Pro Gly Pro Leu
                195                 200                 205

Tyr Asn Cys Ser Ala Lys Asp Thr Phe Lys Leu Lys Val Lys Pro Gly
                210                 215                 220

Lys Thr Tyr Leu Leu Arg Met Ile Asn Ala Ala Leu Asn Asp Glu Leu
225                 230                 235                 240

Phe Phe Ser Ile Ala Asn His Thr Val Thr Val Val Asp Val Asp Ala
                245                 250                 255

Val Tyr Val Lys Pro Phe Asp Ala Glu Thr Leu Leu Ile Thr Pro Gly
                260                 265                 270

Gln Thr Thr Asn Val Leu Leu Lys Thr Lys Pro Asp Tyr Pro Asn Ala
                275                 280                 285

Gln Phe Phe Met Ser Ala Arg Pro Tyr Ala Thr Gly Gln Gly Thr Phe
                290                 295                 300

Asp Asn Ser Thr Val Ala Gly Ile Leu Glu Tyr Glu Val Pro Asn Lys
305                 310                 315                 320

Thr Ser Gln Ser Asn His Ser Thr Lys Lys Leu Pro Leu Tyr Lys Pro
                325                 330                 335
```

```
Asn Leu Pro Pro Leu Asn Asp Thr Ser Phe Ala Thr Asn Phe Ser Ser
            340                 345                 350

Lys Leu Arg Ser Leu Ala Ser Ala Asp Phe Pro Ala Asn Val Pro Gln
            355                 360                 365

Lys Val Asp Arg Gln Phe Phe Phe Thr Val Gly Leu Gly Thr Asn Pro
        370                 375                 380

Cys Ser Lys Asn Gln Thr Cys Gln Gly Pro Asn Gly Thr Arg Phe Ala
385                 390                 395                 400

Ala Ser Val Asn Asn Val Ser Phe Val Met Pro Thr Thr Ala Leu Leu
                405                 410                 415

Gln Ala His His Phe Gly Gln Ser Arg Gly Val Tyr Ser Pro Tyr Phe
            420                 425                 430

Pro Ile Ser Pro Leu Ile Pro Phe Asn Tyr Thr Gly Thr Pro Pro Asn
            435                 440                 445

Asn Thr Met Val Ser Asn Gly Thr Lys Leu Val Val Leu Pro Phe Asn
            450                 455                 460

Thr Ser Val Glu Leu Ile Met Gln Gly Thr Ser Ile Leu Gly Ala Glu
465                 470                 475                 480

Ser His Pro Leu His Leu His Gly Phe Asn Phe Phe Val Val Gly Gln
                485                 490                 495

Gly Phe Gly Asn Phe Asp Pro Ser Lys Asp Pro Ala Asn Phe Asn Leu
            500                 505                 510

Val Asp Pro Val Glu Arg Asn Thr Val Gly Val Pro Ser Gly Gly Trp
            515                 520                 525

Val Ala Ile Arg Phe Leu Ala Asp Asn Pro Gly Val Trp Phe Met His
        530                 535                 540

Cys His Leu Glu Val His Thr Ser Trp Gly Leu Lys Met Ala Trp Val
545                 550                 555                 560

Val Leu Asp Gly Lys Leu Pro Asn Gln Lys Leu Pro Pro Pro Pro Ala
                565                 570                 575

Asp Leu Pro Lys Cys
            580

<210> SEQ ID NO 30
<211> LENGTH: 581
<212> TYPE: PRT
<213> ORGANISM: Populus trichocarpa

<400> SEQUENCE: 30

Met Gly Ala Ser Leu Leu Pro Pro Pro Ala Phe Leu Ala Val Phe Leu
1               5                   10                  15

Phe Ser Phe Val Thr Leu Ser Val Asn Pro Glu Pro Ala Leu Ala Ile
            20                  25                  30

Thr Arg His Tyr Lys Phe Asp Val Met Leu Gln Asn Val Thr Arg Leu
            35                  40                  45

Cys His Thr Lys Ser Met Val Thr Val Asn Gly Lys Phe Pro Gly Pro
        50                  55                  60

Arg Ile Val Ala Arg Glu Gly Asp Arg Leu Val Ile Thr Val Val Asn
65              70                  75                  80

His Val Gln Asn Asn Ile Ser Ile His Trp His Gly Ile Arg Gln Leu
                85                  90                  95

Arg Ser Gly Trp Ala Asp Gly Pro Ala Tyr Val Thr Gln Cys Pro Ile
            100                 105                 110

Gln Thr Gly Gln Ser Tyr Val Tyr Asn Tyr Thr Ile Val Gly Gln Arg
        115                 120                 125
```

```
Gly Thr Leu Trp Trp His Ala His Ile Ser Trp Leu Arg Ser Thr Leu
    130                 135                 140

Tyr Gly Pro Ile Ile Leu Leu Pro Lys Leu Gly Thr Pro Tyr Pro Phe
145                 150                 155                 160

Ala Lys Pro Tyr Lys Glu Val Pro Ile Ile Phe Gly Glu Trp Phe Asn
                165                 170                 175

Ala Asp Pro Glu Ala Ile Ile Asn Gln Ala Met Gln Thr Gly Gly Gly
            180                 185                 190

Pro Asn Val Ser Asp Ala Tyr Thr Ile Asn Gly Leu Pro Gly Pro Leu
        195                 200                 205

Tyr Asn Cys Ser Ala Lys Asp Thr Phe Lys Leu Lys Val Lys Pro Gly
    210                 215                 220

Lys Thr Tyr Leu Leu Arg Met Ile Asn Ala Ala Leu Asn Asp Glu Leu
225                 230                 235                 240

Phe Phe Ser Ile Ala Asn His Thr Val Thr Val Val Asp Val Asp Ala
                245                 250                 255

Val Tyr Val Lys Pro Phe Asp Ala Glu Thr Leu Leu Ile Thr Pro Gly
                260                 265                 270

Gln Thr Thr Asn Val Leu Leu Lys Thr Lys Pro Asp Tyr Pro Asn Ala
        275                 280                 285

Gln Phe Phe Met Ser Ala Arg Pro Tyr Ala Thr Gly Gln Gly Thr Phe
    290                 295                 300

Asp Asn Ser Thr Val Ala Gly Ile Leu Glu Tyr Glu Val Pro Asn Lys
305                 310                 315                 320

Thr Ser Gln Ser Asn His Ser Thr Lys Lys Leu Pro Leu Tyr Lys Pro
                325                 330                 335

Asn Leu Pro Pro Leu Asn Asp Thr Ser Phe Ala Thr Asn Phe Ser Ser
            340                 345                 350

Lys Leu Arg Ser Leu Ala Ser Ala Asp Phe Pro Ala Asn Val Pro Gln
        355                 360                 365

Lys Val Asp Arg Gln Phe Val Phe Thr Val Gly Leu Gly Thr Asn Pro
        370                 375                 380

Cys Ser Lys Asn Gln Thr Cys Gln Gly Pro Asn Gly Thr Arg Phe Ala
385                 390                 395                 400

Ala Ser Val Asn Asn Val Ser Phe Val Met Pro Ser Thr Ala Leu Leu
                405                 410                 415

Gln Ala His His Phe Gly Gln Ser Arg Gly Val Tyr Ser Pro Tyr Phe
            420                 425                 430

Ala Ile Ser Pro Leu Ile Pro Phe Asn Tyr Thr Gly Thr Pro Pro Asn
        435                 440                 445

Asn Thr Met Val Ser Asn Gly Thr Lys Leu Val Val Leu Pro Phe Asn
450                 455                 460

Thr Ser Val Glu Leu Ile Met Gln Asp Thr Ser Ile Leu Gly Ala Glu
465                 470                 475                 480

Ser His Pro Leu His Leu His Gly Phe Asn Phe Val Val Gly Gln
                485                 490                 495

Gly Phe Gly Asn Phe Asp Pro Ser Lys Asp Pro Ala Asn Phe Asn Leu
        500                 505                 510

Val Asp Pro Val Glu Arg Asn Thr Val Gly Val Pro Ser Gly Gly Trp
        515                 520                 525

Val Ala Ile Arg Phe Leu Ala Asp Asn Pro Gly Val Trp Phe Met His
530                 535                 540
```

```
Cys His Leu Glu Val His Thr Ser Trp Gly Leu Lys Met Ala Trp Val
545                 550                 555                 560

Val Leu Asp Gly Lys Leu Pro Asn Gln Lys Leu Leu Pro Pro Ala
            565                 570                 575

Asp Leu Pro Lys Cys
            580

<210> SEQ ID NO 31
<211> LENGTH: 575
<212> TYPE: PRT
<213> ORGANISM: Populus trichocarpa

<400> SEQUENCE: 31

Met Glu Val Ile Lys Ser Ile Phe Ala Asp Arg His Cys Ser Phe Phe
1               5                   10                  15

Leu Val Val Leu Leu Ala Ser Thr Met Ser Leu Ala Ile Ala Glu
            20                  25                  30

Ile His His His Asp Phe Val Val Gln Ala Thr Lys Val Lys Arg Leu
            35                  40                  45

Cys Lys Thr His Asn Ser Ile Thr Val Asn Gly Met Phe Pro Gly Pro
50                  55                  60

Thr Leu Glu Val Lys Asn Gly Asp Thr Leu Val Val Lys Val Val Asn
65                  70                  75                  80

Lys Ala Arg Tyr Asn Val Thr Ile His Trp His Gly Ile Arg Gln Met
                85                  90                  95

Arg Thr Gly Trp Ala Asp Gly Pro Glu Phe Val Thr Gln Cys Pro Ile
            100                 105                 110

Arg Pro Gly Gly Ser Tyr Thr Tyr Arg Phe Asn Ile Glu Gly Gln Glu
            115                 120                 125

Gly Thr Leu Trp Trp His Ala His Ser Ser Trp Leu Arg Ala Thr Val
            130                 135                 140

Tyr Gly Ala Leu Ile Ile His Pro Arg Glu Gly Ser Ser Tyr Pro Phe
145                 150                 155                 160

Ala Lys Pro Lys Arg Glu Thr Pro Ile Leu Leu Gly Glu Trp Trp Asp
                165                 170                 175

Ala Asn Pro Val Asp Val Val Arg Glu Ala Thr Arg Thr Gly Ala Ala
            180                 185                 190

Pro Asn Ile Ser Asp Ala Tyr Thr Ile Asn Gly Gln Pro Gly Asp Leu
            195                 200                 205

Tyr Asn Cys Ser Ser Glu Asp Thr Thr Ile Val Pro Ile Ala Ser Gly
210                 215                 220

Glu Thr Asn Leu Leu Arg Val Ile Asn Ala Ala Leu Asn Gln Pro Leu
225                 230                 235                 240

Phe Phe Thr Ile Ala Asn His Lys Phe Thr Val Ile Gly Ala Asp Ala
                245                 250                 255

Ser Tyr Leu Lys Pro Phe Thr Thr Ser Val Ile Met Leu Gly Pro Gly
            260                 265                 270

Gln Thr Thr Asp Val Leu Ile Ser Gly Asp Gln Leu Pro Gly Arg Tyr
            275                 280                 285

Tyr Met Ala Ala Arg Ala Tyr Gln Ser Ala Gln Asn Ala Pro Phe Asp
290                 295                 300

Asn Thr Thr Thr Ala Ile Leu Glu Tyr Lys Ser Ala Leu Cys Pro
305                 310                 315                 320

Ala Lys Cys Thr Thr Lys Pro Val Met Pro Arg Leu Pro Ala Tyr Asn
                325                 330                 335
```

```
Asp Thr Ala Thr Val Thr Ala Phe Ser Gly Ser Leu Arg Ser Pro Arg
                340                 345                 350

Lys Val Glu Val Pro Thr Asp Ile Asp Glu Asn Leu Phe Phe Thr Ile
            355                 360                 365

Gly Leu Gly Leu Asn Asn Cys Pro Lys Asn Ser Arg Ala Arg Arg Cys
        370                 375                 380

Gln Gly Pro Asn Gly Thr Arg Phe Thr Ala Ser Met Asn Asn Val Ser
385                 390                 395                 400

Phe Val Phe Pro Ser Asn Ile Ala Leu Leu Gln Ala Tyr Gln Gln Lys
                405                 410                 415

Val Pro Gly Ile Tyr Thr Thr Asp Phe Pro Ala Lys Pro Val Lys
            420                 425                 430

Phe Asp Tyr Thr Gly Asn Val Ser Arg Ser Leu Phe Gln Pro Val Arg
            435                 440                 445

Gly Thr Lys Leu Tyr Lys Leu Lys Tyr Gly Ser Arg Val Gln Ile Val
        450                 455                 460

Leu Gln Asp Thr Ser Ile Val Thr Pro Glu Asn His Pro Ile His Leu
465                 470                 475                 480

His Gly Tyr Asp Phe Tyr Ile Ile Ala Glu Gly Phe Gly Asn Phe Asn
                485                 490                 495

Pro Lys Thr His Lys Ser Lys Phe Asn Leu Val Asp Pro Pro Met Arg
            500                 505                 510

Asn Thr Val Ala Val Pro Ser Asn Gly Trp Ala Val Ile Arg Phe Val
        515                 520                 525

Ala Asp Asn Pro Gly Val Trp Leu Met His Cys His Leu Asp Val His
530                 535                 540

Ile Thr Trp Gly Leu Ala Met Ala Phe Leu Val Glu Asp Gly Ile Gly
545                 550                 555                 560

Glu Leu Gln Ser Val Glu Pro Pro Ala Asp Leu Pro Ile Cys
                565                 570                 575

<210> SEQ ID NO 32
<211> LENGTH: 574
<212> TYPE: PRT
<213> ORGANISM: Populus trichocarpa

<400> SEQUENCE: 32

Met Glu Val Ile Asn Arg Ile Phe Ala Asn Arg His Cys Ser Phe Phe
1               5                   10                  15

Leu Leu Leu Leu Leu Ala Ser Ala Met Ser Leu Ala Ile Ala Lys Thr
            20                  25                  30

His His His Asp Phe Thr Val Gln Ala Thr Lys Val Lys Arg Leu Cys
        35                  40                  45

Lys Thr His Asn Ser Ile Thr Val Asn Gly Met Phe Pro Gly Pro Thr
    50                  55                  60

Leu Glu Val Lys Asn Gly Asp Thr Leu Val Val Lys Val Asn Arg
65                  70                  75                  80

Ala Arg Tyr Asn Val Thr Ile His Trp His Gly Ile Arg Gln Met Arg
                85                  90                  95

Thr Gly Trp Ala Asp Gly Pro Glu Phe Val Thr Gln Cys Pro Ile Arg
            100                 105                 110

Pro Gly Gly Ser Tyr Thr Tyr Arg Phe Thr Ile Glu Gly Gln Glu Gly
        115                 120                 125

Thr Leu Trp Trp His Ala His Ser Ser Trp Leu Arg Ala Thr Val Tyr
```

```
            130                 135                 140
Gly Ala Leu Ile Ile His Pro Arg Glu Gly Ser Ser Tyr Pro Phe Ser
145                 150                 155                 160

Lys Pro Lys Arg Glu Thr Pro Ile Leu Leu Gly Glu Trp Trp Asp Thr
                    165                 170                 175

Asn Pro Ile Asp Val Val Arg Glu Ala Thr Arg Thr Gly Ala Ala Pro
                180                 185                 190

Asn Ile Ser Asp Ala Tyr Thr Ile Asn Gly Gln Pro Gly Asp Leu Phe
                195                 200                 205

Asn Cys Ser Ser Lys Asp Thr Thr Ile Val Pro Ile Asp Ser Gly Glu
        210                 215                 220

Thr Asn Leu Leu Arg Val Ile Asn Ala Ala Leu Asn Gln Pro Leu Phe
225                 230                 235                 240

Phe Thr Ile Ala Asn His Lys Phe Thr Val Val Gly Ala Asp Ala Ser
                    245                 250                 255

Tyr Leu Lys Pro Phe Thr Thr Ser Val Ile Met Leu Gly Pro Gly Gln
                260                 265                 270

Thr Thr Asp Val Leu Ile Ser Gly Asp Gln Leu Pro Gly Arg Tyr Tyr
            275                 280                 285

Met Ala Ala Arg Ala Tyr Gln Ser Ala Gln Asn Ala Pro Phe Asp Asn
        290                 295                 300

Thr Thr Thr Thr Ala Ile Leu Glu Tyr Lys Ser Val Leu Cys Pro Ala
305                 310                 315                 320

Lys Cys Thr Lys Lys Pro Phe Met Pro Pro Leu Pro Ala Tyr Asn Asp
                    325                 330                 335

Thr Ala Thr Val Thr Ala Phe Ser Arg Ser Phe Arg Ser Pro Arg Lys
                340                 345                 350

Val Glu Val Pro Thr Asp Ile Asp Glu Asn Leu Phe Phe Thr Ile Gly
            355                 360                 365

Leu Gly Leu Asn Asn Cys Pro Lys Asn Phe Arg Ala Arg Arg Cys Gln
        370                 375                 380

Gly Pro Asn Gly Thr Arg Phe Thr Ala Ser Met Asn Asn Val Ser Phe
385                 390                 395                 400

Val Phe Pro Ser Lys Ala Ser Leu Leu Gln Ala Tyr Lys Gln Lys Ile
                    405                 410                 415

Pro Gly Val Phe Thr Thr Asp Phe Pro Ala Lys Pro Gln Val Lys Phe
                420                 425                 430

Asp Tyr Thr Gly Asn Val Ser Arg Ser Leu Phe Gln Pro Ala Arg Gly
            435                 440                 445

Thr Lys Leu Tyr Lys Leu Lys Tyr Gly Ser Arg Val Gln Ile Val Leu
        450                 455                 460

Gln Asp Thr Ser Ile Val Thr Pro Glu Asn His Pro Ile His Leu His
465                 470                 475                 480

Gly Tyr Asp Phe Tyr Ile Ile Ala Glu Gly Phe Gly Asn Phe Asn Pro
                    485                 490                 495

Lys Thr Asp Lys Ser Lys Phe Asn Leu Val Asp Pro Met Arg Asn
                500                 505                 510

Thr Val Ala Val Pro Val Asn Gly Trp Ala Val Ile Arg Phe Val Ala
            515                 520                 525

Asp Asn Pro Gly Val Trp Leu Met His Cys His Leu Asp Val His Ile
        530                 535                 540

Thr Trp Gly Leu Ala Met Ala Phe Leu Val Glu Glu Gly Ile Gly Ile
545                 550                 555                 560
```

```
Leu Gln Ser Val Glu Pro Pro Ala Asp Leu Pro Ile Cys
            565             570
```

<210> SEQ ID NO 33
<211> LENGTH: 582
<212> TYPE: PRT
<213> ORGANISM: Populus trichocarpa

<400> SEQUENCE: 33

```
Met Glu Gly Phe Asp Asn Ile Phe Ala Ile Asn His Arg Leu Ser Leu
1               5                   10                  15

Phe Phe Leu Gly Leu Leu Leu Leu Ala Ser Ala Leu Ser Leu Ala
            20                  25                  30

Asn Ala Glu Thr His Asn His Asp Phe Val Ile Gln Ala Thr Pro Val
            35                  40                  45

Lys Arg Leu Cys Lys Thr Gln Asn Ser Ile Thr Val Asn Gly Met Phe
50                  55                  60

Pro Gly Pro Thr Leu Glu Val Asn Asn Gly Asp Thr Leu Val Val Asn
65                  70                  75                  80

Val Val Asn Lys Ala Gln Tyr Asn Val Thr Ile His Trp His Gly Val
                85                  90                  95

Arg Gln Met Arg Thr Gly Trp Ala Asp Gly Pro Glu Phe Val Thr Gln
            100                 105                 110

Cys Pro Ile Arg Pro Gly Gly Ser Tyr Thr Tyr Lys Phe Thr Ile Gln
        115                 120                 125

Gly Gln Glu Gly Thr Leu Trp Trp His Ala His Ser Ser Trp Leu Arg
130                 135                 140

Ala Thr Val Tyr Gly Ala Leu Ile Val His Pro Lys Glu Gly Ser Pro
145                 150                 155                 160

Tyr Pro Phe Ser Lys Gln Pro Lys Arg Glu Thr Ala Ile Leu Leu Gly
                165                 170                 175

Glu Trp Trp Asn Ala Asn Pro Ile Asp Val Val Arg Glu Ala Thr Arg
            180                 185                 190

Thr Gly Gly Ala Pro Asn Val Ser Asp Ala Tyr Thr Val Asn Gly Gln
        195                 200                 205

Pro Gly Asp Leu Tyr Asn Cys Ser Ser Gln Asp Thr Val Ile Val Pro
210                 215                 220

Ile Asp Ser Gly Glu Thr Asn Leu Leu Arg Val Val Asn Ser Ala Leu
225                 230                 235                 240

Asn Gln Pro Leu Phe Phe Thr Val Ala Asn His Lys Phe Thr Val Val
                245                 250                 255

Gly Ala Asp Ala Ser Tyr Val Lys Pro Phe Thr Thr Ser Val Leu Met
            260                 265                 270

Leu Gly Pro Gly Gln Thr Thr Asp Val Leu Ile Ser Gly Asp Gln Thr
        275                 280                 285

Pro Ser Arg Tyr Tyr Met Ala Ala Arg Ala Tyr Gln Ser Ala Gln Asn
290                 295                 300

Ala Pro Phe Asp Asn Thr Thr Thr Ala Ile Leu Glu Tyr Lys Ser
305                 310                 315                 320

Ser Ala Cys Ala Ala Lys Asn Cys Ser Ser Asn Lys Pro Ile Met Pro
                325                 330                 335

Pro Leu Pro Ala Tyr Asn Asp Thr Ala Thr Val Thr Thr Phe Thr Thr
            340                 345                 350

Ser Phe Lys Ser Ala Asp Lys Thr Leu Val Pro Thr Asp Ile Asp Glu
```

```
                355                 360                 365
Ser Leu Phe Phe Thr Ile Gly Leu Gly Leu Asn Pro Cys Pro Ser Asn
    370                 375                 380

Phe Asn Lys Ser Ser Gln Cys Gln Gly Pro Asn Gly Thr Arg Phe Thr
385                 390                 395                 400

Ala Ser Met Asn Asn Val Ser Phe Val Leu Pro Ser Asn Phe Ser Leu
                405                 410                 415

Leu Gln Ala His His Gln Arg Ile Gln Gly Val Phe Thr Thr Asp Phe
            420                 425                 430

Pro Ala Asn Pro Pro Arg Lys Phe Asp Tyr Thr Gly Asn Val Ser Arg
        435                 440                 445

Ser Leu Phe Gln Pro Val Ala Gly Thr Lys Leu Tyr Asn Leu Lys Tyr
    450                 455                 460

Gly Ser Arg Val Gln Ile Val Leu Gln Asp Thr Ser Ile Val Thr Pro
465                 470                 475                 480

Glu Asn His Pro Ile His Leu His Gly Tyr Asp Phe Tyr Ile Ile Ala
                485                 490                 495

Gln Gly Phe Gly Asn Tyr Asn Pro Arg Ala Asp Pro Ser Lys Phe Asn
            500                 505                 510

Leu Val Asp Pro Pro Leu Arg Asn Thr Val Ala Val Pro Val Asn Gly
        515                 520                 525

Trp Ala Val Ile Arg Phe Val Ala Asp Asn Pro Gly Val Trp Leu Met
    530                 535                 540

His Cys His Leu Asp Val His Ile Thr Trp Gly Leu Ala Thr Ala Phe
545                 550                 555                 560

Leu Val Glu Asn Gly Val Gly Gln Leu Gln Ser Ile Glu Ser Pro Pro
                565                 570                 575

Glu Asp Leu Pro Leu Cys
            580

<210> SEQ ID NO 34
<211> LENGTH: 582
<212> TYPE: PRT
<213> ORGANISM: Populus trichocarpa

<400> SEQUENCE: 34

Met Glu Val Phe Asn Asn Ile Phe Ala Ile Asn His Arg Cys Ser Ser
1               5                   10                  15

Phe Phe Leu Gly Leu Leu Leu Leu Ala Ser Ala Leu Ser Leu Ala
                20                  25                  30

Asn Ala Lys Ser His Tyr His Asp Phe Val Ile Gln Ala Thr Pro Val
            35                  40                  45

Lys Arg Leu Cys Lys Thr Gln Asn Ser Ile Thr Val Asn Gly Met Phe
50                  55                  60

Pro Gly Pro Thr Leu Glu Val Asn Asn Gly Asp Thr Leu Val Val Asn
65                  70                  75                  80

Val Val Asn Lys Ala Arg Tyr Asn Val Thr Ile His Trp His Gly Ile
                85                  90                  95

Arg Gln Met Arg Thr Gly Trp Ala Asp Gly Pro Glu Phe Val Thr Gln
            100                 105                 110

Cys Pro Ile Arg Pro Gly Gly Ser Tyr Thr Tyr Arg Phe Thr Ile Gln
        115                 120                 125

Gly Gln Glu Gly Thr Leu Trp Trp His Ala His Ser Ser Trp Leu Arg
    130                 135                 140
```

```
Ala Thr Val Tyr Gly Ala Leu Ile Ile His Pro Lys Glu Gly Ser Ser
145                 150                 155                 160

Tyr Pro Phe Ser Lys Gln Pro Lys Arg Glu Thr Ala Ile Leu Leu Gly
            165                 170                 175

Glu Trp Trp Asn Ala Asn Pro Ile Asp Val Val Arg Glu Ser Thr Arg
        180                 185                 190

Thr Gly Gly Thr Pro Asn Ser Ser Asp Ala Tyr Thr Ile Asn Gly Gln
    195                 200                 205

Pro Gly Asp Leu Tyr Asn Cys Ser Ser Gln Asp Thr Val Ile Val Pro
210                 215                 220

Ile Asp Ser Gly Glu Thr Asn Leu Leu Arg Val Val Asn Ser Ala Leu
225                 230                 235                 240

Asn Gln Pro Leu Phe Phe Thr Val Ala Asn His Lys Leu Thr Val Val
                245                 250                 255

Gly Ala Asp Ala Ser Tyr Val Lys Pro Phe Thr Thr Ser Val Leu Met
                260                 265                 270

Leu Gly Pro Gly Gln Thr Thr Asp Val Leu Ile Ser Gly Asp Gln Asn
            275                 280                 285

Pro Ser Arg Tyr Tyr Met Ala Ala Arg Ala Tyr Gln Ser Ala Gln Asn
        290                 295                 300

Ala Pro Phe Asp Asn Thr Thr Thr Ala Ile Leu Glu Tyr Lys Ser
305                 310                 315                 320

Ser Pro Cys Ala Ala Lys Asn Cys Ser Ser Asn Lys Pro Ile Met Pro
            325                 330                 335

Pro Leu Pro Thr Phe Asn Asp Thr Ala Thr Val Thr Ala Phe Thr Ser
        340                 345                 350

Ser Phe Lys Ser Thr Asp Lys Thr Phe Val Pro Thr Asp Ile Asp Glu
            355                 360                 365

Ser Leu Phe Phe Thr Val Gly Leu Gly Leu Asn Pro Cys Pro Pro Asn
        370                 375                 380

Phe Asn Lys Ser Ser Gln Cys Gln Gly Pro Asn Gly Thr Arg Phe Thr
385                 390                 395                 400

Ala Ser Met Asn Asn Val Ser Phe Val Leu Pro Ser Asn Phe Ser Leu
                405                 410                 415

Leu Gln Ala His His Gln Arg Ile Gln Gly Val Phe Thr Thr Asp Phe
            420                 425                 430

Pro Ala Asn Pro Pro Arg Lys Phe Asp Tyr Thr Gly Asn Val Ser Arg
            435                 440                 445

Ser Leu Phe Thr Pro Val Pro Gly Thr Lys Leu Tyr Arg Leu Lys Tyr
        450                 455                 460

Gly Ser Arg Val Gln Ile Val Leu Gln Asp Thr Ser Ile Val Thr Ser
465                 470                 475                 480

Glu Asn His Pro Ile His Leu His Gly Tyr Asp Phe Tyr Ile Ile Ala
            485                 490                 495

Gln Gly Phe Gly Asn Tyr Asn Pro Arg Thr Asp Pro Ser Lys Phe Asn
            500                 505                 510

Leu Val Asp Pro Pro Leu Arg Asn Thr Val Ala Val Pro Val Asn Gly
            515                 520                 525

Trp Ala Val Ile Arg Phe Val Ala Asp Asn Pro Gly Val Trp Leu Met
            530                 535                 540

His Cys His Leu Asp Val His Ile Thr Trp Gly Leu Ala Thr Ala Phe
545                 550                 555                 560

Leu Val Glu Asn Gly Val Gly Glu Leu Gln Ser Ile Glu Ser Pro Pro
```

Glu Asp Leu Pro Leu Cys
            580

<210> SEQ ID NO 35
<211> LENGTH: 579
<212> TYPE: PRT
<213> ORGANISM: Populus trichocarpa

<400> SEQUENCE: 35

Met Glu Gly Val Arg Lys His Tyr Gly Ile Leu Leu Ala Ser Leu Ala
1               5                   10                  15

Ile Ile Ala Ala Ala Leu Pro Cys Cys Ser Ser Gln Thr Thr Arg Arg
            20                  25                  30

Phe Gln Phe Asn Val Glu Trp Lys Gln Val Thr Arg Leu Cys Thr Thr
        35                  40                  45

Lys Gln Leu Leu Met Val Asn Gly Gln Tyr Pro Gly Pro Thr Ile Ala
    50                  55                  60

Val His Glu Gly Asp Asn Val Glu Ile Asn Val Lys Asn Gln Ile Ala
65                  70                  75                  80

Gln Asn Thr Thr Leu His Trp His Gly Val Arg Gln Leu Arg Thr Gly
                85                  90                  95

Trp Ala Asp Gly Pro Ala Tyr Val Thr Gln Cys Pro Ile Arg Gly Gly
            100                 105                 110

Gln Ser Tyr Thr Tyr Lys Phe Thr Val Thr Gly Gln Arg Gly Thr Leu
        115                 120                 125

Leu Trp His Ala His Tyr Ala Trp Gln Arg Ala Ser Val Tyr Gly Ala
    130                 135                 140

Phe Ile Ile Tyr Pro Arg Ile Pro Tyr Pro Phe Ser His Pro Ile Gln
145                 150                 155                 160

Ala Glu Ile Pro Ile Ile Phe Gly Glu Trp Trp Asn Gly Asp Pro Asp
                165                 170                 175

Glu Val Glu Asn Arg Thr Met Leu Thr Gly Ala Gly Pro Asp Ser Ser
            180                 185                 190

Asn Ala Tyr Thr Ile Asn Gly Leu Pro Gly Pro Leu Tyr Pro Cys Ser
        195                 200                 205

Asn Gln Asp Thr Tyr Ile Gln Thr Val Glu Tyr Gly Lys Thr Tyr Met
    210                 215                 220

Leu Arg Ile Ile Asn Ala Ala Leu Ala Asp Glu Leu Phe Phe Ala Ile
225                 230                 235                 240

Ala Lys His Thr Leu Thr Val Val Glu Val Asp Ala Val Tyr Thr Lys
                245                 250                 255

Pro Phe Ala Thr Thr Ser Ile Met Ile Ala Pro Gly Gln Thr Thr Thr
            260                 265                 270

Val Leu Met Thr Ala Asn Gln Val Pro Asp Phe Thr Gly Met Phe Val
        275                 280                 285

Met Ala Ala Arg Pro Tyr Leu Thr Ser Val Phe Pro Phe Asn Asn Ser
    290                 295                 300

Thr Thr Ile Gly Phe Leu Arg Tyr Lys Asn Ala Arg Thr Trp Lys Gly
305                 310                 315                 320

Lys Ser Pro Val Asp Pro Ser Ser Leu Lys Leu His Asn Leu Pro Ala
                325                 330                 335

Met Glu Asp Thr Ala Phe Ala Thr Lys Phe Ser Asp Lys Ile Lys Ser
            340                 345                 350

Leu Ala Ser Pro Gln Tyr Pro Cys Asn Val Pro Lys Thr Ile Asp Lys
            355                 360                 365

Arg Val Ile Thr Thr Ile Ser Leu Asn Ile Gln Asp Cys Pro Glu Asn
    370                 375                 380

Lys Thr Cys Ser Gly Tyr Lys Gly Lys Ser Phe Phe Ala Ser Met Asn
385                 390                 395                 400

Asn Gln Ser Phe Val Arg Pro Ser Ile Ser Ile Leu Glu Ser Tyr Tyr
                405                 410                 415

Lys Asn Leu Thr Thr Gly Ser Phe Ser Asp Phe Pro Glu Lys Pro
            420                 425                 430

Pro Asn Asn Phe Asp Tyr Thr Gly Gly Asp Pro Leu Thr Gln Asn Met
            435                 440                 445

Asn Thr Lys Phe Gly Thr Lys Leu Ile Val Pro Tyr Gly Thr Asn
450                 455                 460

Val Glu Ile Val Leu Gln Asp Thr Ser Phe Val Asn Leu Glu Asn His
465                 470                 475                 480

Pro Ile His Val His Gly His Asn Phe Phe Ile Val Gly Ser Gly Phe
                485                 490                 495

Gly Asn Phe Asn Glu Ala Arg Asp Pro Lys Arg Tyr Asn Leu Val Asp
                500                 505                 510

Pro Pro Glu Arg Asn Thr Val Ala Val Pro Ser Gly Gly Trp Ala Ala
            515                 520                 525

Ile Arg Ile Lys Ala Asp Asn Pro Gly Val Trp Phe Ile His Cys His
            530                 535                 540

Leu Glu Gln His Thr Ser Trp Gly Leu Ala Thr Gly Phe Ile Val Gln
545                 550                 555                 560

Asn Gly Gln Gly Pro Ser Gln Ser Met Leu Pro Pro Gln Asp Leu
            565                 570                 575

Pro Ser Cys

<210> SEQ ID NO 36
<211> LENGTH: 562
<212> TYPE: PRT
<213> ORGANISM: Populus trichocarpa

<400> SEQUENCE: 36

Met Leu Arg Leu Leu Phe Trp Leu Thr Cys Ala Leu Val Leu Leu Ala
1               5                   10                  15

Ser Ser Val Ala Ser Ala Ala Ile Val Glu His Ser Phe Tyr Val Lys
            20                  25                  30

Asn Leu Thr Val Arg Arg Leu Cys Thr Glu Gln Val Val Thr Ala Val
            35                  40                  45

Asn Gly Ser Leu Pro Gly Pro Thr Leu Arg Val Gln Glu Gly Asp Thr
    50                  55                  60

Leu Lys Val His Val Phe Asn Lys Ser Pro Tyr Asn Met Thr Leu His
65                  70                  75                  80

Trp His Gly Val Phe Gln Leu Leu Ser Ala Trp Ala Asp Gly Pro Asn
                85                  90                  95

Met Val Thr Gln Cys Pro Ile Pro Pro Gly Gly Lys Tyr Thr Tyr Gln
                100                 105                 110

Phe Lys Leu Leu Lys Gln Glu Gly Thr Leu Trp Trp His Ala His Val
            115                 120                 125

Ser Trp Leu Arg Ala Thr Val Tyr Gly Ala Leu Ile Ile Arg Pro Arg
    130                 135                 140

```
Ser Gly His Pro Tyr Pro Phe Pro Lys Pro Asp Lys Glu Val Pro Ile
145                 150                 155                 160

Leu Phe Gly Glu Trp Trp Asn Ala Asn Val Val Asp Val Glu Asn Gln
                165                 170                 175

Ala Leu Ala Ser Gly Ala Ala Pro Asn Thr Ser Asp Ala Phe Thr Ile
            180                 185                 190

Asn Gly Leu Pro Gly Asp Leu Tyr Pro Cys Ser Gln Asn Arg Ile Phe
        195                 200                 205

Lys Leu Lys Val Gln Lys Gly Lys Thr Tyr Leu Leu Arg Ile Ile Asn
    210                 215                 220

Ala Ala Leu Asn Asn Glu Leu Phe Phe Lys Ile Ala Asn His Asn Met
225                 230                 235                 240

Lys Val Val Ala Val Asp Ala Gly Tyr Thr Val Pro Tyr Val Thr Gly
                245                 250                 255

Val Val Val Ile Gly Pro Gly Gln Thr Val Asp Val Leu Leu Ala Ala
                260                 265                 270

Asp Gln Glu Val Gly Ser Tyr Tyr Met Ala Ala Asn Ala Tyr Ser Ser
    275                 280                 285

Ala Ala Gly Ala Pro Phe Asp Asn Thr Thr Thr Arg Gly Ile Val Val
290                 295                 300

Tyr Glu Gly Ala Pro Thr Ser Ala Thr Pro Ile Met Pro Leu Met Pro
305                 310                 315                 320

Ala Phe Asn Asp Thr Pro Thr Ala His Lys Phe Phe Thr Asn Ile Thr
                325                 330                 335

Gly Leu Ala Gly Gly Pro His Trp Val Pro Val Pro Arg Gln Ile Asp
            340                 345                 350

Glu His Met Phe Val Thr Met Gly Leu Gly Leu Ser Ile Cys Pro Thr
                355                 360                 365

Cys Ser Asn Gly Thr Arg Leu Ser Ala Ser Met Asn Asn Phe Ser Phe
        370                 375                 380

Val Ser Pro Thr Thr Leu Ser Met Leu Gln Ala Phe Phe Phe Asn Val
385                 390                 395                 400

Ser Gly Ile Tyr Thr Pro Asp Phe Pro Asp Thr Pro Pro Ile Lys Phe
                405                 410                 415

Asp Tyr Thr Asn Ala Ser Ile Asn Ala Leu Asn Pro Ser Leu Leu Ile
            420                 425                 430

Thr Pro Lys Ser Thr Ser Val Lys Val Leu Lys Tyr Asn Ser Thr Val
        435                 440                 445

Glu Met Val Leu Gln Asn Thr Ala Ile Leu Ala Val Glu Asn His Pro
    450                 455                 460

Met His Leu His Gly Phe Asn Phe His Val Leu Ala Gln Gly Phe Gly
465                 470                 475                 480

Asn Tyr Asp Pro Val Lys Asp Pro Lys Lys Phe Asn Leu Val Asn Pro
                485                 490                 495

Gln Ser Arg Asn Thr Ile Gly Val Pro Val Gly Gly Trp Ala Val Ile
            500                 505                 510

Arg Phe Thr Ala Asn Asn Pro Gly Val Trp Phe Met His Cys His Leu
        515                 520                 525

Asp Val His Leu Pro Trp Gly Leu Ala Thr Ala Phe Val Val Lys Asn
    530                 535                 540

Gly Pro Thr Glu Asp Ser Thr Leu Pro Pro Pro Ala Asp Leu Pro
545                 550                 555                 560

Gln Cys
```

<210> SEQ ID NO 37
<211> LENGTH: 579
<212> TYPE: PRT
<213> ORGANISM: Populus trichocarpa

<400> SEQUENCE: 37

```
Met Glu Ala Val Arg Lys His Tyr Gly Ile Leu Leu Ala Ser Leu Ala
1               5                   10                  15

Ile Ile Ala Ala Ala Leu Pro Cys Cys Ser Ser Glu Thr Thr Arg Arg
            20                  25                  30

Phe Gln Phe Asn Val Glu Trp Lys Lys Val Thr Arg Leu Cys Thr Thr
        35                  40                  45

Lys Gln Leu Leu Met Val Asn Gly Gln Tyr Pro Gly Pro Thr Ile Ala
    50                  55                  60

Val His Glu Gly Asp Asn Val Glu Ile Lys Val Lys Asn Arg Ile Ala
65                  70                  75                  80

Gln Asn Thr Thr Leu His Trp His Gly Val Arg Gln Leu Arg Thr Gly
                85                  90                  95

Trp Ala Asp Gly Pro Ala Tyr Ile Thr Gln Cys Pro Ile Arg Gly Gly
            100                 105                 110

Gln Ser Tyr Thr Tyr Lys Phe Thr Val Thr Gly Gln Arg Gly Thr Leu
        115                 120                 125

Leu Trp His Ala His Tyr Ala Trp Gln Arg Ala Ser Val Tyr Gly Ala
    130                 135                 140

Leu Ile Ile Tyr Pro Arg Ile Pro Tyr Pro Phe Ser His Pro Ile Gln
145                 150                 155                 160

Ala Glu Ile Pro Ile Ile Phe Gly Glu Trp Trp Asn Gly Asp Pro Asp
                165                 170                 175

Glu Ile Glu Lys Thr Met Leu Leu Thr Gly Gly Pro Asp Ser Ser
            180                 185                 190

Asn Ala Tyr Thr Ile Asn Gly Leu Pro Gly Pro Leu Tyr Pro Cys Ser
        195                 200                 205

Asn Gln Asp Thr Phe Ile Gln Thr Val Glu Tyr Gly Lys Thr Tyr Leu
    210                 215                 220

Leu Arg Ile Ile Asn Ala Ala Leu Thr Asn Glu Leu Phe Phe Ala Ile
225                 230                 235                 240

Ala Lys His Thr Leu Thr Val Val Glu Val Asp Ala Val Tyr Thr Lys
                245                 250                 255

Pro Phe Ala Thr Thr Ser Ile Met Ile Ala Pro Gly Gln Thr Thr Thr
            260                 265                 270

Val Leu Met Thr Ala Asn Gln Val Pro Asp Phe Thr Gly Met Phe Val
        275                 280                 285

Met Ala Ala Arg Pro Tyr Leu Thr Ser Val Phe Pro Phe Asn Asn Ser
    290                 295                 300

Thr Thr Ile Gly Phe Leu Arg Tyr Lys Asn Ala Arg Thr Trp Lys Gly
305                 310                 315                 320

Lys Ser Pro Val Asp Pro Ser Ser Leu Arg Leu His Asn Leu Pro Ala
                325                 330                 335

Met Glu Asp Thr Ala Phe Ala Thr Lys Phe Ser Asp Lys Ile Lys Ser
            340                 345                 350

Leu Ala Ser Pro Gln Tyr Pro Cys Asn Val Pro Lys Thr Ile Asp Lys
        355                 360                 365

Arg Val Ile Thr Thr Ile Ser Leu Asn Leu Gln Asp Cys Pro Glu Asn
```

```
            370                 375                 380
Lys Thr Cys Leu Gly Leu Lys Gly Lys Ser Phe Phe Ala Ser Met Asn
385                 390                 395                 400

Asn Gln Ser Phe Val Arg Pro Ser Ile Ser Ile Leu Glu Ser Tyr Tyr
                405                 410                 415

Lys Asn Leu Thr Thr Ser Ser Phe Ser Ser Asp Phe Pro Gln Lys Pro
                420                 425                 430

Pro Asn Asn Phe Asp Tyr Thr Gly Val His Pro Leu Thr Gln Asn Met
                435                 440                 445

Asn Thr Lys Phe Gly Thr Lys Leu Leu Val Leu Pro Tyr Gly Thr Asn
                450                 455                 460

Ile Glu Ile Val Leu Gln Asp Thr Ser Phe Leu Asn Leu Glu Asn His
465                 470                 475                 480

Pro Ile His Val His Gly His Asn Phe Ile Val Gly Ser Gly Phe
                485                 490                 495

Gly Asn Phe Asn Glu Ala Arg Asp Pro Lys Arg Tyr Asn Leu Val Asp
                500                 505                 510

Pro Pro Glu Arg Asn Thr Val Ala Val Pro Ser Gly Gly Trp Ala Ala
                515                 520                 525

Ile Arg Ile Lys Ala Asp Asn Pro Gly Val Trp Phe Val His Cys His
                530                 535                 540

Leu Glu Gln His Thr Ser Trp Gly Leu Ala Thr Gly Phe Ile Val Gln
545                 550                 555                 560

Asn Gly Gln Gly Pro Ser Gln Ser Leu Leu Pro Pro His Asp Leu
                565                 570                 575

Pro Ser Cys

<210> SEQ ID NO 38
<211> LENGTH: 576
<212> TYPE: PRT
<213> ORGANISM: Populus trichocarpa

<400> SEQUENCE: 38

Met Glu Thr Arg Asn Leu Thr Val Lys Gln Val Ser Tyr Cys Leu Phe
1               5                   10                  15

Leu Ser Ile Phe Val Ile Phe Ser Phe Gln Ala His Phe Ser Glu Ala
                20                  25                  30

Glu Thr His Tyr Arg Glu Phe Val Ile Gln Ala Lys Pro Val Lys Arg
                35                  40                  45

Leu Cys Arg Thr His Asn Thr Ile Thr Val Asn Gly Leu Phe Pro Gly
50                  55                  60

Pro Thr Leu Glu Val Arg Asp Gly Asp Thr Leu Val Ile Lys Ala Val
65                  70                  75                  80

Asn Asn Ala Arg Tyr Asn Val Thr Leu His Trp His Gly Ile Arg Gln
                85                  90                  95

Leu Arg Asn Pro Trp Ala Asp Gly Pro Asp Arg Val Thr Gln Cys Pro
                100                 105                 110

Ile Arg Pro Gly Arg Ser Tyr Thr Tyr Arg Phe Thr Ile Glu Asn Gln
                115                 120                 125

Glu Gly Thr Leu Trp Trp His Ala His Ser Arg Trp Leu Arg Ala Thr
                130                 135                 140

Val Tyr Gly Ala Leu Ile Ile His Pro Lys Leu Gly Ser Pro Tyr Pro
145                 150                 155                 160

Phe Pro Met Pro Arg Thr Glu Ile Pro Ile Leu Leu Gly Glu Trp Trp
```

```
                165                 170                 175
Asp Arg Asn Pro Met Asp Val Leu Arg Ile Ala Asp Phe Thr Gly Ala
            180                 185                 190

Ala Pro Asn Ile Ser Asp Ala Tyr Thr Ile Asn Gly Gln Pro Gly Asp
            195                 200                 205

Leu Tyr Arg Cys Ser Lys Gln Glu Thr Val Arg Phe Pro Val Gly Ser
    210                 215                 220

Gly Glu Thr Ile Leu Leu Arg Val Ile Asn Ser Ala Leu Asn Gln Glu
225                 230                 235                 240

Leu Phe Phe Gly Val Ala Asn His Ile Leu Thr Val Val Ala Val Asp
                245                 250                 255

Ala Ala Tyr Thr Lys Pro Phe Thr Thr Ser Val Ile Met Ile Ala Pro
            260                 265                 270

Gly Gln Thr Thr Asp Val Leu Leu Thr Ala Asp Gln Thr Pro Gly His
            275                 280                 285

Tyr Tyr Met Ala Ala Arg Ala Tyr Asn Ser Ala Asn Ala Pro Phe Asp
    290                 295                 300

Asn Thr Thr Thr Thr Ala Ile Leu Glu Tyr Lys Thr Ala Pro Arg Asn
305                 310                 315                 320

Ala Lys Lys Gly Lys Gln Ser Thr Pro Ile Phe Pro Arg Leu Pro Gly
                325                 330                 335

Phe Asn Asp Thr Asn Ser Ala Ile Ala Phe Thr Ser Arg Leu Arg Ser
            340                 345                 350

Pro Ser Lys Val Lys Val Pro Leu Gln Ile Asp Glu Asn Leu Phe Phe
    355                 360                 365

Thr Val Gly Leu Gly Leu Ile Asn Cys Thr Asn Pro Asn Ser Pro Arg
370                 375                 380

Cys Gln Gly Pro Asn Gly Thr Arg Phe Ala Ala Ser Ile Asn Asn Met
385                 390                 395                 400

Ser Phe Val Leu Pro Lys Arg Asn Ser Leu Met Gln Ala Tyr Tyr Gln
                405                 410                 415

Gly Gln Pro Gly Ile Phe Thr Thr Asp Phe Pro Pro Val Pro Pro Val
            420                 425                 430

Lys Phe Asp Tyr Thr Gly Asn Val Ser Arg Gly Leu Trp Gln Pro Val
            435                 440                 445

Lys Ser Thr Lys Leu Tyr Lys Leu Lys Phe Gly Ala Lys Val Gln Ile
    450                 455                 460

Val Leu Gln Asp Thr Ser Ile Val Thr Val Glu Asp His Pro Met His
465                 470                 475                 480

Leu His Gly Tyr His Phe Ala Val Ile Gly Ser Gly Phe Gly Asn Phe
                485                 490                 495

Asn Pro Gln Thr Asp Pro Ala Arg Phe Asn Leu Ile Asp Pro Pro Tyr
            500                 505                 510

Arg Asn Thr Ile Gly Thr Pro Pro Gly Gly Trp Val Ala Ile Arg Phe
            515                 520                 525

Glu Ala Asp Asn Pro Gly Ile Trp Phe Met His Cys His Leu Asp Ser
    530                 535                 540

His Leu Asn Trp Gly Leu Gly Met Ala Phe Leu Val Glu Asn Gly Val
545                 550                 555                 560

Gly Lys Leu Gln Ser Val Gln Pro Pro Leu Asp Leu Pro Arg Cys
                565                 570                 575

<210> SEQ ID NO 39
```

```
<211> LENGTH: 579
<212> TYPE: PRT
<213> ORGANISM: Populus trichocarpa

<400> SEQUENCE: 39
```

| | | | | | | | | | | | | | | |
|---|---|---|---|---|---|---|---|---|---|---|---|---|---|---|
|Met|Glu|Gly|Gly|His|Lys|Asn|Ser|Gly|Ile|Leu|Leu|Val|Ser|Leu|Val|
|1| | | |5| | | | |10| | | | |15|
|Ile|Ile|Ala|Gly|Ala|Leu|Pro|Phe|Cys|Ser|Ser|Gln|Ala|Thr|Arg|Arg|
| | | | |20| | | | |25| | | | |30|
|Phe|Gln|Phe|Asn|Val|Glu|Trp|Lys|Lys|Val|Thr|Arg|Leu|Cys|Thr|Thr|
| | | | |35| | | | |40| | | | |45|
|Lys|Gln|Leu|Leu|Thr|Val|Asn|Gly|Gln|Tyr|Pro|Gly|Pro|Thr|Ile|Ala|
|50| | | | |55| | | | |60| | | | |
|Val|His|Glu|Gly|Asp|Arg|Val|Glu|Ile|Lys|Val|Lys|Asn|Arg|Ile|Ala|
|65| | | | |70| | | | |75| | | | |80|
|His|Asn|Thr|Thr|Leu|His|Trp|His|Gly|Leu|Arg|Gln|Leu|Arg|Thr|Gly|
| | | | |85| | | | |90| | | | |95|
|Trp|Ala|Asp|Gly|Pro|Ala|Tyr|Ile|Thr|Gln|Cys|Pro|Ile|Arg|Gly|Gly|
| | | | |100| | | | |105| | | | |110|
|Gln|Ser|Tyr|Thr|Tyr|Lys|Phe|Thr|Val|Ile|Lys|Gln|Arg|Gly|Thr|Leu|
| | | | |115| | | | |120| | | | |125|
|Leu|Trp|His|Ala|His|Tyr|Ala|Trp|Gln|Arg|Ala|Ser|Val|Tyr|Gly|Ala|
| | | | |130| | | | |135| | | | |140|
|Leu|Ile|Ile|Tyr|Pro|Arg|Met|Pro|Tyr|Pro|Phe|Ser|Ala|Gln|Ile|Gln|
|145| | | | |150| | | | |155| | | | |160|
|Ala|Glu|Ile|Pro|Ile|Ile|Leu|Gly|Glu|Trp|Trp|Asn|Gly|Asp|Pro|Asp|
| | | | |165| | | | |170| | | | |175|
|Glu|Val|Glu|Lys|Ile|Met|Met|Leu|Thr|Gly|Ala|Gly|Pro|Asp|Ser|Ser|
| | | | |180| | | | |185| | | | |190|
|Asn|Ala|Tyr|Thr|Ile|Asn|Gly|Met|Pro|Gly|Pro|Leu|Tyr|Pro|Cys|Ser|
| | | | |195| | | | |200| | | | |205|
|Asn|Arg|Asp|Thr|Phe|Ile|Gln|Thr|Val|Glu|Tyr|Gly|Arg|Thr|Tyr|Met|
| | | | |210| | | | |215| | | | |220|
|Leu|Arg|Ile|Ile|Asn|Ala|Ala|Leu|Ala|Asn|Glu|Leu|Phe|Phe|Ala|Ile|
|225| | | | |230| | | | |235| | | | |240|
|Ala|Lys|His|Lys|Leu|Thr|Val|Val|Glu|Val|Asp|Ala|Val|Tyr|Thr|Lys|
| | | | |245| | | | |250| | | | |255|
|Pro|Phe|Thr|Thr|Thr|Ser|Ile|Met|Ile|Ala|Pro|Gly|Gln|Thr|Thr|Thr|
| | | | |260| | | | |265| | | | |270|
|Val|Leu|Met|Thr|Ala|Asn|Gln|Val|Pro|Asp|Ser|Thr|Gly|Met|Phe|Ala|
| | | | |275| | | | |280| | | | |285|
|Met|Ala|Ala|Arg|Pro|Tyr|Leu|Thr|Ser|Val|Phe|Pro|Ser|Asn|Asn|Ser|
| | | | |290| | | | |295| | | | |300|
|Thr|Thr|Ile|Ser|Phe|Leu|Arg|Tyr|Lys|Asn|Ala|Arg|Asn|Arg|Arg|Gly|
|305| | | | |310| | | | |315| | | | |320|
|Lys|Pro|Pro|Ser|Asn|Leu|Ser|Ser|Leu|Lys|Leu|Tyr|Asn|Leu|Pro|Ala|
| | | | |325| | | | |330| | | | |335|
|Met|Glu|Asp|Thr|Ala|Phe|Ala|Thr|Lys|Phe|Ser|Gly|Asn|Ile|Lys|Ser|
| | | | |340| | | | |345| | | | |350|
|Leu|Ala|Ser|Pro|Lys|Tyr|Pro|Cys|Asp|Val|Pro|Lys|Thr|Ile|Asp|Lys|
| | | | |355| | | | |360| | | | |365|
|Arg|Val|Ile|Thr|Thr|Ile|Ser|Leu|Asn|Leu|Gln|Asp|Cys|Pro|Ala|Lys|
|370| | | | |375| | | | |380| | | | |
|Lys|Thr|Cys|Leu|Gly|Phe|Arg|Gly|Lys|Lys|Phe|Phe|Ala|Ser|Met|Asn|

```
            385                 390                 395                 400
Asn Gln Ser Phe Val Arg Pro Ser Ile Ser Ile Leu Glu Ser Tyr Tyr
                    405                 410                 415
Lys Asn Leu Thr Thr Thr Ser Phe Ser Ser Asp Phe Pro Glu Lys Pro
                420                 425                 430
Pro Asn Ala Phe Asp Tyr Thr Gly Gly Asp Pro Leu Ser Gln Asn Met
            435                 440                 445
Asn Thr Glu Phe Gly Thr Lys Leu Ile Val Pro Tyr Gly Thr Asn
        450                 455                 460
Leu Glu Ile Val Leu Gln Asp Thr Ser Phe Leu Asn Leu Glu Asn His
465                 470                 475                 480
Pro Ile His Val His Gly His Asn Phe Phe Ile Val Gly Ser Gly Phe
                485                 490                 495
Gly Asn Phe Asn Lys Ala Lys Asp Pro Lys Arg Tyr Asn Leu Val Asp
                500                 505                 510
Pro Pro Glu Arg Asn Thr Val Ala Val Pro Ser Gly Gly Trp Ala Ala
                515                 520                 525
Ile Arg Ile Lys Ala Asp Asn Pro Gly Val Trp Phe Ile His Cys His
            530                 535                 540
Leu Glu Gln His Thr Ser Trp Gly Leu Ala Ala Gly Phe Ile Val Gln
545                 550                 555                 560
Asn Gly Gln Glu Pro Ser Gln Arg Leu Leu Pro Pro Gln Asp Leu
                565                 570                 575
Pro Ser Cys

<210> SEQ ID NO 40
<211> LENGTH: 567
<212> TYPE: PRT
<213> ORGANISM: Populus trichocarpa

<400> SEQUENCE: 40

Met Gly Ile Ser Arg Leu Gly Phe Ile Ala Gly Leu Ile Trp Phe Met
1               5                   10                  15
Ala Met Asp Trp Gln Gly Leu Cys Met Ala Gln Ser Asn Val His Arg
                20                  25                  30
Tyr Asn Phe Val Leu Gln Asn Ala Gln Phe Thr Arg Leu Cys Glu Thr
            35                  40                  45
Lys Thr Met Leu Thr Val Asn Gly Ser Phe Pro Gly Pro Thr Ile His
        50                  55                  60
Ala Arg Arg Gly Asp Thr Ile Tyr Val Asn Val His Asn Glu Gly Asp
65                  70                  75                  80
Tyr Gly Val Thr Ile His Trp His Gly Val Lys Gln Pro Arg Asn Pro
                85                  90                  95
Trp Ser Asp Gly Pro Glu Asn Ile Thr Gln Cys Pro Ile Gln Pro Gly
                100                 105                 110
Lys Asn Phe Thr Tyr Glu Ile Ile Leu Ser Asp Glu Glu Gly Thr Leu
            115                 120                 125
Trp Trp His Ala His Ser Asp Trp Thr Arg Ala Thr Val His Gly Ala
        130                 135                 140
Ile Val Ile Ser Pro Ala Arg Gly Thr Thr Tyr Pro Phe Pro Ala Pro
145                 150                 155                 160
Tyr Ala Glu Gln Thr Ile Ile Ile Gly Ser Trp Phe Lys Gly Asp Val
                165                 170                 175
Lys Ala Val Ile Asp Glu Ala Leu Ala Thr Gly Ala Gly Pro Ala Ile
```

```
              180             185                 190
Ser Asn Ser Leu Thr Ile Asn Gly Gln Pro Gly Asp Leu Tyr Pro Cys
        195                 200             205

Ser Glu Glu Asn Thr Tyr Arg Leu Lys Val Asn Ser Gly Arg Thr Tyr
        210                 215             220

Leu Leu Arg Val Ile Asn Ala Val Met Asn Glu Gln Phe Phe Gly
225                 230                 235                 240

Ile Ala Gly His Ser Leu Thr Val Val Gly Gln Asp Ala Ala Tyr Ile
            245                 250                 255

Lys Pro Ile Thr Thr Asn Tyr Ile Met Ile Thr Pro Gly Gln Thr Met
                260                 265             270

Asp Ile Leu Val Thr Ala Asn Gln Pro Arg Ser Tyr Tyr Ile Ala
            275                 280             285

Ser Tyr Ser Phe Ser Asp Gly Ala Met Val Ala Phe Asp Glu Thr Thr
        290                 295             300

Thr Thr Ala Ile Phe Gln Tyr Asn Gly Asn Tyr Ser Arg Pro Ser Ala
305                 310                 315                 320

Ile Pro Leu Pro Val Leu Pro Val Phe Asn Asp Ser Ala Ala Glu
                325                 330                 335

Asn Tyr Thr Ser Arg Val Arg Gly Leu Ala Ser Arg Asp His Pro Val
            340                 345                 350

Asn Val Pro Gln Thr Ile Asn Arg Arg Leu Tyr Ile Thr Ile Ala Leu
                355                 360             365

Asn Tyr Leu Pro Cys Thr Glu Ala Thr Cys Ile Asn Ser Thr Arg Leu
            370                 375                 380

Ala Ala Ser Met Asn Asn Val Ser Phe Ala Ala Lys Pro Ile Asp Ile
385                 390                 395                 400

Leu Gln Ala Tyr Tyr Arg Ser Ile Asn Gly Val Phe Asp Ala Asp Phe
                405                 410                 415

Pro Arg Glu Pro Gln Lys Tyr Phe Asn Phe Thr Gly Asn Met Thr Ser
                420                 425             430

Ile Asn Val Ala Thr Ala Arg Gly Thr Lys Val Thr Met Leu Asn Tyr
                435                 440                 445

Gly Glu Ala Val Glu Ile Val Phe Gln Gly Thr Asn Leu Leu Ala Glu
        450                 455             460

Met Asn His Pro Ile His Leu His Gly Phe Ser Phe Tyr Leu Val Gly
465                 470                 475                 480

His Gly Lys Gly Asn Phe Asn Asn Glu Thr Asp Pro Lys Ser Tyr Asn
                485                 490                 495

Leu Ile Asp Pro Pro Glu Ile Asn Thr Val Ala Leu Pro Arg Ser Gly
                500                 505             510

Trp Ala Ala Ile Arg Phe Val Ala Asn Asn Pro Gly Val Trp Phe Ile
            515                 520             525

His Cys His Leu Glu Lys His Ser Ser Trp Gly Met Asp Thr Val Leu
            530                 535             540

Ile Val Arg Asn Gly Arg Thr Arg Ala Gln Ser Met Arg Pro Pro Pro
545                 550                 555                 560

Ala Thr Leu Pro Ser Cys Ser
                565

<210> SEQ ID NO 41
<211> LENGTH: 567
<212> TYPE: PRT
<213> ORGANISM: Populus trichocarpa
```

<400> SEQUENCE: 41

```
Met Gly Ile Ser Arg Leu Gly Phe Ile Ala Gly Leu Ile Trp Phe Met
1               5                   10                  15

Ala Met Asp Trp Gln Gly Leu Cys Met Ala Gln Ser Asn Val His Arg
            20                  25                  30

Tyr Asn Phe Val Leu Gln Asn Ala Gln Phe Thr Arg Leu Cys Glu Thr
        35                  40                  45

Lys Thr Met Leu Thr Val Asn Gly Ser Phe Pro Gly Pro Thr Ile His
    50                  55                  60

Ala Arg Arg Gly Asp Thr Ile Tyr Val Asn Val His Asn Glu Gly Asp
65                  70                  75                  80

Tyr Gly Val Thr Ile His Trp His Gly Val Lys Gln Pro Arg Asn Pro
                85                  90                  95

Trp Ser Asp Gly Pro Glu Asn Ile Thr Gln Cys Pro Ile Gln Pro Gly
            100                 105                 110

Lys Asn Phe Thr Tyr Glu Ile Ile Leu Ser Asp Glu Glu Gly Thr Leu
        115                 120                 125

Trp Trp His Ala His Ser Asp Trp Thr Arg Ala Thr Val His Gly Ala
    130                 135                 140

Ile Val Ile Ser Pro Ala Arg Gly Thr Thr Tyr Pro Phe Pro Ala Pro
145                 150                 155                 160

Tyr Ala Glu Gln Thr Ile Ile Ile Gly Ser Trp Phe Lys Gly Asp Val
                165                 170                 175

Lys Ala Val Ile Asp Glu Ala Leu Ala Thr Gly Gly Pro Asn Ile
            180                 185                 190

Ser Asn Ser Leu Thr Ile Asn Gly Gln Pro Gly Asp Leu Tyr Pro Cys
        195                 200                 205

Ser Glu Glu Asn Thr Tyr Arg Leu Lys Val Asn Ser Gly Arg Thr Tyr
    210                 215                 220

Leu Leu Arg Val Ile Asn Ala Val Met Asn Glu Gln Phe Phe Gly
225                 230                 235                 240

Ile Ala Gly His Ser Leu Thr Val Val Gly Gln Asp Ala Ala Tyr Ile
                245                 250                 255

Lys Pro Ile Thr Thr Asn Tyr Ile Met Ile Thr Pro Gly Gln Thr Met
            260                 265                 270

Asp Ile Leu Val Thr Ala Asn Arg Pro Arg Ser Tyr Tyr Ile Ala
        275                 280                 285

Ser His Ser Phe Ala Asp Gly Ala Gly Ile Ala Phe Asp Asn Thr Thr
    290                 295                 300

Thr Thr Ala Ile Phe Gln Tyr Asn Gly Asn Tyr Gly Arg Pro Ser Ser
305                 310                 315                 320

Ile Pro Leu Pro Val Leu Pro Ile Phe Asn Asp Thr Ala Ala Glu
                325                 330                 335

Asn Tyr Thr Ser Arg Val Arg Gly Leu Ala Ser Arg Asp His Pro Val
            340                 345                 350

Asn Val Pro Gln Thr Ile Asn Arg Arg Leu Tyr Ile Ala Ile Ala Leu
        355                 360                 365

Asn Phe Leu Pro Cys Thr Glu Ala Thr Cys Thr Gly Pro Asn Arg Leu
    370                 375                 380

Ala Ala Ser Met Asn Asn Val Ser Phe Ala Ala Lys Pro Ile Asp Ile
385                 390                 395                 400

Leu Gln Ala Tyr Tyr Arg Ser Ile Asn Gly Val Phe Asp Ala Asp Phe
```

```
            405                 410                 415
Pro Arg Glu Pro Gln Lys Tyr Phe Asn Phe Thr Gly Asn Met Thr Ser
            420                 425                 430

Ile Asn Val Ala Thr Ala Arg Gly Thr Lys Val Thr Met Leu Asn Tyr
            435                 440                 445

Gly Glu Ala Val Glu Ile Val Phe Gln Gly Thr Asn Leu Leu Ala Glu
            450                 455                 460

Met Asn His Pro Ile His Leu His Gly Phe Ser Phe Tyr Leu Val Gly
465                 470                 475                 480

His Gly Lys Gly Asn Phe Asn Asn Glu Thr Asp Pro Lys Ser Tyr Asn
                485                 490                 495

Leu Ile Asp Pro Pro Glu Ile Asn Thr Val Ala Leu Pro Arg Ser Gly
                500                 505                 510

Trp Ala Ala Ile Arg Phe Val Ala Asn Asn Pro Gly Val Trp Phe Ile
                515                 520                 525

His Cys His Leu Glu Lys His Ser Ser Trp Gly Met Asp Thr Val Leu
                530                 535                 540

Ile Val Arg Asn Gly Arg Thr Arg Ala Gln Ser Met Arg Pro Pro Pro
545                 550                 555                 560

Ala Thr Leu Pro Ser Cys Ser
                565

<210> SEQ ID NO 42
<211> LENGTH: 572
<212> TYPE: PRT
<213> ORGANISM: Populus trichocarpa

<400> SEQUENCE: 42

Met Ala Asn Leu Val Thr Ser Phe Met Leu Trp Leu Cys Leu Ile Ser
1               5                   10                  15

Tyr Ala Tyr Thr Thr Ile His Ala Ala Pro Glu Trp Pro Arg Gly Arg
                20                  25                  30

Ser Thr Arg Phe Tyr Asp Phe Lys Ile Gln Thr Met Thr Val Asn Lys
            35                  40                  45

Leu Cys Asn Ser Lys Gln Ile Val Thr Val Asn Asn Met Phe Pro Gly
        50                  55                  60

Pro Val Val Tyr Ala Gln Gln Gly Asp Arg Leu Ile Val Lys Val Ser
65                  70                  75                  80

Asn Glu Ser Pro Tyr Asn Ala Thr Ile His Trp His Gly Val Arg Gln
                85                  90                  95

Ile Leu Ser Cys Trp Phe Asp Gly Pro Ser Tyr Ile Thr Gln Cys Pro
            100                 105                 110

Ile Gln Pro Gly Gln Thr Phe Thr Tyr Glu Phe Thr Leu Val Gly Gln
        115                 120                 125

Lys Gly Thr Phe Phe Trp His Ala His Val Ser Trp Leu Arg Ala Thr
130                 135                 140

Val Tyr Gly Ala Leu Val Val Tyr Pro Lys Pro Gly Val Pro Tyr Pro
145                 150                 155                 160

Phe Lys Tyr Pro Tyr Glu Glu His Ile Val Ile Leu Gly Glu Tyr Trp
                165                 170                 175

Leu Gln Asp Ile Val His Leu Glu Arg Gln Val Val Ala Ser Gly Gly
            180                 185                 190

Gly Pro Pro Pro Ala Asn Ala Tyr Thr Ile Asn Gly His Pro Gly Pro
        195                 200                 205
```

Asn Tyr Asn Cys Ser Ala Thr Asp Val Tyr Lys Ile Asp Val Leu Pro
210                 215                 220

Gly Lys Thr Tyr Leu Leu Arg Leu Ile Asn Ala Gly Leu Asn Met Glu
225                 230                 235                 240

Asn Phe Phe Ala Ile Ala Asn His Lys Leu Thr Ile Val Glu Ala Asp
            245                 250                 255

Ala Glu Tyr Thr Lys Pro Phe Thr Thr Asp Arg Val Met Leu Gly Pro
                260                 265                 270

Gly Gln Thr Met Ile Val Leu Val Thr Ala Asp Gln Thr Ile Gly Lys
                275                 280                 285

Tyr Ser Met Ala Met Gly Pro Tyr Ala Ser Gly Gln Asn Val Ala Phe
290                 295                 300

Gln Asn Ile Ser Ala Ile Ala Tyr Phe Gln Tyr Val Gly Ala Met Pro
305                 310                 315                 320

Asn Ser Leu Ser Leu Pro Ala Arg Leu Pro Ser Phe Asn Asp Asn Leu
                325                 330                 335

Ala Val Lys Thr Val Met Asp Gly Leu Arg Gly Leu Asn Thr Ser Asp
                340                 345                 350

Val Pro Lys Glu Ile Asp Thr Asn Leu Phe Leu Thr Ile Gly Met Asn
                355                 360                 365

Val Asn Lys Cys Arg Ser Lys Thr Pro Gln Gln Asn Cys Gln Gly Leu
370                 375                 380

Asn Asn Gly Thr Met Ala Ala Ser Met Asn Asn Ile Ser Phe Ile Lys
385                 390                 395                 400

Pro Thr Val Ser Val Leu Glu Ala Tyr Tyr Lys Gly Ile Asp Gly Phe
                405                 410                 415

Phe Thr Asp Asn Phe Pro Gly Ala Pro Phe Arg Phe Tyr Asp Phe Val
                420                 425                 430

Asn Gly Ala Pro Asn Asn Ala Pro Asn Asp Thr Ser Ser Met Asn Gly
                435                 440                 445

Thr Arg Val Lys Val Leu Glu Tyr Gly Thr Arg Val Gln Met Ile Leu
450                 455                 460

Gln Asp Thr Gly Thr Val Thr Thr Glu Asn His Pro Ile His Leu His
465                 470                 475                 480

Gly Tyr Ser Phe Tyr Val Val Gly Tyr Gly Ala Gly Asn Tyr Asn Pro
                485                 490                 495

Gln Thr Ala Asn Leu Asn Leu Val Asp Pro Pro Tyr Met Asn Thr Ile
                500                 505                 510

Gly Val Pro Val Gly Gly Trp Ala Ala Ile Arg Phe Val Ala Asp Asn
                515                 520                 525

Pro Gly Val Trp Phe Met His Cys His Leu Asp Ile His Gln Ser Trp
530                 535                 540

Gly Leu Gly Thr Val Phe Ile Val Lys Asn Gly Asn Gly His Leu Glu
545                 550                 555                 560

Thr Leu Pro His Pro Pro Ala Asp Leu Pro Arg Cys
                565                 570

<210> SEQ ID NO 43
<211> LENGTH: 568
<212> TYPE: PRT
<213> ORGANISM: Populus trichocarpa

<400> SEQUENCE: 43

Met Ser Arg Leu Leu Phe Leu Leu Thr Cys Ala Leu Ala Leu Leu Ala
1               5                   10                  15

```
Ser Ser Val Ala Ser Ala Ala Ile Val Glu His Ser Phe Tyr Val Gln
         20                  25                  30

Asn Leu Thr Val Arg Arg Leu Cys Ser Glu Gln Val Thr Ala Val
         35                  40                  45

Asn Gly Ser Leu Pro Gly Pro Thr Leu Arg Val Arg Glu Gly Asp Thr
 50                  55                  60

Leu Ile Val His Val Phe Asn Lys Ser Pro Tyr Asn Leu Thr Ile His
 65                  70                  75                  80

Trp His Gly Val Phe Gln Leu Ser Ala Trp Ala Asp Gly Pro Ser
             85                  90                  95

Met Val Thr Gln Cys Pro Ile Pro Pro Gly Lys Tyr Thr Tyr Lys
             100                 105                 110

Phe Glu Leu Leu Gln Gln Glu Gly Thr Leu Trp Trp His Ala His Val
             115                 120                 125

Ser Phe Leu Arg Ala Thr Val Tyr Gly Ala Leu Val Ile Arg Pro Arg
 130                 135                 140

Ser Gly His Pro Tyr Pro Phe Pro Lys Pro His Arg Glu Val Pro Ile
 145                 150                 155                 160

Leu Leu Gly Glu Trp Trp Asn Ala Asn Val Asp Val Glu Asn Gln
             165                 170                 175

Ala Glu Ala Ile Gly Ala Pro Pro Asn Ile Ser Asp Ala Tyr Thr Ile
             180                 185                 190

Asn Gly Leu Pro Gly Asp Leu Tyr Asn Cys Ser Gln Asn Arg Met Tyr
             195                 200                 205

Lys Leu Lys Val Gln Lys Gly Lys Thr Tyr Leu Leu Arg Ile Ile Asn
             210                 215                 220

Ala Ala Leu Asn Asn Gln Leu Phe Phe Lys Ile Ala Asn His Asn Met
 225                 230                 235                 240

Thr Val Val Ala Val Asp Ala Gly Tyr Thr Val Pro Tyr Val Thr Asp
             245                 250                 255

Val Val Val Thr Gly Pro Gly Gln Thr Val Asp Val Leu Leu Ala Ala
             260                 265                 270

Asp Gln Glu Val Gly Ser Tyr Phe Met Ala Ala Asn Ala Tyr Ala Ser
             275                 280                 285

Ala Gly Pro Ala Pro Pro Ala Phe Pro Ala Pro Pro Phe Asp Asn Thr
             290                 295                 300

Thr Thr Arg Gly Thr Val Val Tyr Glu Gly Ala Pro Thr Ser Ala Thr
 305                 310                 315                 320

Pro Ile Met Pro Leu Met Pro Ala Phe Thr Asp Thr Pro Ala His
             325                 330                 335

Lys Phe Phe Thr Ser Ile Thr Gly Leu Ala Gly Gly Pro His Trp Val
             340                 345                 350

Pro Val Pro Arg Gln Val Asp Glu His Met Phe Val Thr Val Gly Leu
             355                 360                 365

Gly Leu Ser Ile Cys Pro Thr Cys Leu Asn Gly Thr Arg Leu Ser Ala
 370                 375                 380

Ser Met Asn Asn Phe Ser Phe Ala Arg Pro Ser Ser Leu Ser Met Leu
 385                 390                 395                 400

Gln Ala Phe Phe Phe Asn Val Ser Gly Ile Tyr Thr Pro Asp Phe Pro
             405                 410                 415

Asp Thr Pro Pro Val Lys Phe Asp Tyr Thr Asn Val Ile Asn Ala Val
             420                 425                 430
```

-continued

```
Asn Pro Ser Leu Leu Ile Thr Pro Lys Ser Thr Ser Val Lys Val Leu
            435                 440                 445

Lys Tyr Asn Ala Thr Val Glu Met Val Leu Gln Asn Thr Ala Leu Leu
450                 455                 460

Gly Val Glu Asn His Pro Ile His Leu His Gly Phe Asn Phe His Val
465                 470                 475                 480

Leu Ala Gln Gly Phe Gly Asn Tyr Asp Pro Val Asn Asp Pro Lys Lys
                485                 490                 495

Phe Asn Leu Ile Asn Pro Leu Ser Arg Asn Thr Ile Asn Val Pro Val
            500                 505                 510

Gly Gly Trp Gly Val Ile Arg Phe Thr Ala Asn Asn Pro Gly Val Trp
515                 520                 525

Phe Phe His Cys His Leu Asp Val His Leu Pro Phe Gly Leu Ala Thr
530                 535                 540

Ala Phe Val Val Glu Asn Gly Pro Thr Pro Glu Ser Thr Leu Pro Pro
545                 550                 555                 560

Pro Pro Val Asp Leu Pro Gln Cys
                565

<210> SEQ ID NO 44
<211> LENGTH: 567
<212> TYPE: PRT
<213> ORGANISM: Populus trichocarpa

<400> SEQUENCE: 44

Met Gly Ile Ser Arg Leu Gly Phe Ile Ala Gly Leu Ile Trp Phe Met
1               5                   10                  15

Ala Met Asp Trp Gln Gly Leu Cys Met Ala Gln Ser Ser Val His Arg
            20                  25                  30

Tyr Asn Phe Val Leu Gln Asn Ala Gln Phe Thr Arg Leu Cys Glu Thr
        35                  40                  45

Lys Thr Met Leu Thr Val Asn Gly Ser Phe Pro Gly Pro Thr Ile His
    50                  55                  60

Ala Arg Arg Gly Asp Thr Ile Tyr Val Asn Val His Asn Glu Gly Asp
65                  70                  75                  80

Tyr Gly Val Thr Ile His Trp His Gly Val Lys Gln Pro Arg Asn Pro
                85                  90                  95

Trp Ser Asp Gly Pro Glu Asn Ile Thr Gln Cys Pro Ile Gln Pro Gly
            100                 105                 110

Lys Asn Phe Thr Tyr Glu Ile Ile Leu Ser Asp Glu Glu Gly Thr Leu
        115                 120                 125

Trp Trp His Ala His Ser Asp Trp Thr Arg Ala Thr Val His Gly Ala
    130                 135                 140

Ile Val Ile Ser Pro Ala Arg Gly Thr Thr Tyr Pro Phe Pro Ala Pro
145                 150                 155                 160

Tyr Ala Glu Gln Thr Ile Ile Ile Gly Ser Trp Phe Lys Gly Asp Val
                165                 170                 175

Lys Ala Val Ile Asp Glu Ala Leu Ala Thr Gly Val Gly Pro Asn Ile
            180                 185                 190

Ser Asn Ser Leu Thr Ile Asn Gly Gln Pro Gly Asp Leu Tyr Pro Cys
        195                 200                 205

Ser Asp Lys Asn Thr Tyr Arg Leu Lys Val Asn Ser Gly Arg Thr Tyr
    210                 215                 220

Leu Leu Arg Val Ile Asn Ala Val Met Asn Glu Glu Gln Phe Phe Gly
225                 230                 235                 240
```

Ile Ala Gly His Ser Leu Thr Val Val Gly Gln Asp Ala Ala Tyr Ile
          245                 250                 255

Lys Pro Ile Thr Thr Asn Tyr Ile Met Ile Thr Pro Gly Gln Thr Met
          260                 265                 270

Glu Ile Leu Val Thr Ala Asn Gln Pro Pro Ser Tyr Tyr Ile Ala
          275                 280                 285

Ser His Ser Phe Val Asp Gly Ala Gly Ile Ala Phe Asp Asn Thr Thr
          290                 295                 300

Thr Thr Ala Ile Phe Gln Tyr Asn Gly Asn Tyr Ser Arg Pro Lys Ser
305                 310                 315                 320

Ile Pro Arg Pro Val Leu Pro Val Phe Asn Asp Thr Ala Ala Glu
          325                 330                 335

Asn Tyr Thr Ser Arg Val Arg Gly Leu Ala Ser Arg Asp His Pro Val
          340                 345                 350

Asn Val Pro Gln Ile Ile Asn Arg Arg Leu Tyr Ile Thr Ile Ala Leu
          355                 360                 365

Asn Phe Leu Pro Cys Thr Glu Ala Thr Cys Asn Ser Ser Thr Arg Leu
          370                 375                 380

Ala Ala Ser Met Asn Asn Val Ser Phe Ala Ala Lys Pro Ile Asp Ile
385                 390                 395                 400

Leu Gln Ala Tyr Tyr Arg Ser Ile Asn Gly Val Phe Asp Ala Asp Phe
          405                 410                 415

Pro Ser Glu Pro Gln Lys Tyr Phe Asn Phe Thr Gly Asp Val Thr Ser
          420                 425                 430

Ile Asn Val Ala Thr Ala Arg Gly Thr Lys Val Thr Met Leu Asn Tyr
          435                 440                 445

Gly Glu Ala Val Glu Ile Val Phe Gln Gly Thr Asn Leu Leu Ala Glu
          450                 455                 460

Met Asn His Pro Ile His Leu His Gly Phe Ser Phe Tyr Leu Val Gly
465                 470                 475                 480

His Gly Lys Gly Asn Phe Asn Asn Glu Thr Asp Pro Lys Ser Tyr Asn
          485                 490                 495

Leu Ile Asp Pro Pro Glu Ile Asn Thr Val Ala Leu Arg Arg Ser Gly
          500                 505                 510

Trp Ala Ala Ile Arg Phe Val Ala Asn Asn Pro Gly Val Trp Phe Ile
          515                 520                 525

His Cys His Leu Glu Lys His Ser Ser Trp Gly Met Asp Thr Val Leu
          530                 535                 540

Ile Val Arg Asn Gly Asn Thr Thr Ala Gln Ser Met Arg Pro Pro Pro
545                 550                 555                 560

Ala Thr Leu Pro Ser Cys Ser
          565

<210> SEQ ID NO 45
<211> LENGTH: 568
<212> TYPE: PRT
<213> ORGANISM: Populus trichocarpa

<400> SEQUENCE: 45

Met Ser Arg Leu Leu Phe Leu Leu Thr Cys Ala Leu Ala Leu Leu Ala
1               5                   10                  15

Ser Ser Val Ala Ser Ala Ala Ile Val Glu His Ser Phe Tyr Val Gln
          20                  25                  30

Asn Leu Thr Val Arg Arg Leu Cys Ser Glu Gln Val Val Thr Ala Val

```
            35                  40                  45
Asn Gly Ser Leu Pro Gly Pro Thr Leu Arg Val Arg Glu Gly Asp Thr
 50                  55                  60

Leu Ile Val His Val Phe Asn Lys Ser Pro Tyr Asn Leu Thr Ile His
 65                  70                  75                  80

Trp His Gly Val Phe Gln Leu Leu Ser Ala Trp Ala Asp Gly Pro Ser
                 85                  90                  95

Met Val Thr Gln Cys Pro Ile Pro Pro Gly Lys Tyr Thr Tyr Lys
                100                 105                 110

Phe Glu Leu Leu Gln Gln Glu Gly Thr Leu Trp Trp His Ala His Val
            115                 120                 125

Ser Phe Leu Arg Ala Thr Val Tyr Gly Ala Leu Val Ile Arg Pro Arg
        130                 135                 140

Ser Gly His Pro Tyr Pro Phe Pro Lys Pro His Arg Glu Val Pro Ile
145                 150                 155                 160

Leu Leu Gly Glu Trp Trp Asn Ala Asn Val Val Asp Val Glu Asn Gln
                165                 170                 175

Ala Glu Ala Ile Gly Ala Pro Pro Asn Ile Ser Asp Ala Tyr Thr Ile
            180                 185                 190

Asn Gly Leu Pro Gly Asp Leu Tyr Asn Cys Ser Gln Asn Arg Met Tyr
        195                 200                 205

Lys Leu Lys Val Gln Lys Gly Lys Thr Tyr Leu Leu Arg Ile Ile Asn
210                 215                 220

Ala Ala Leu Asn Asn Gln Leu Phe Phe Lys Ile Ala Asn His Asn Met
225                 230                 235                 240

Thr Val Val Ala Val Asp Ala Gly Tyr Thr Val Pro Tyr Val Thr Asp
                245                 250                 255

Val Val Val Thr Gly Pro Gly Gln Thr Val Asp Val Leu Leu Ala Ala
            260                 265                 270

Asp Gln Glu Val Gly Ser Tyr Phe Met Ala Ala Asn Ala Tyr Ala Ser
        275                 280                 285

Ala Gly Pro Ala Pro Ala Phe Pro Ala Pro Pro Phe Asp Asn Thr
290                 295                 300

Thr Thr Arg Gly Thr Val Val Tyr Glu Gly Ala Pro Thr Ser Ala Thr
305                 310                 315                 320

Pro Ile Met Pro Leu Met Pro Ala Phe Thr Asp Thr Pro Thr Ala His
                325                 330                 335

Lys Phe Phe Thr Ser Ile Thr Gly Leu Ala Gly Gly Pro His Trp Val
            340                 345                 350

Pro Val Pro Arg Gln Val Asp Glu His Met Phe Val Thr Val Gly Leu
        355                 360                 365

Gly Leu Ser Ile Cys Pro Thr Cys Leu Asn Gly Thr Arg Leu Ser Ala
    370                 375                 380

Ser Met Asn Asn Phe Ser Phe Ala Arg Pro Ser Ser Leu Ser Met Leu
385                 390                 395                 400

Gln Ala Phe Phe Phe Asn Val Ser Gly Ile Tyr Thr Pro Asp Phe Pro
                405                 410                 415

Asp Thr Pro Pro Val Lys Phe Asp Tyr Thr Asn Val Ile Asn Ala Val
            420                 425                 430

Asn Pro Ser Leu Leu Ile Thr Pro Lys Ser Thr Ser Val Lys Val Leu
        435                 440                 445

Lys Tyr Asn Ala Thr Val Glu Met Val Leu Gln Asn Thr Ala Leu Leu
    450                 455                 460
```

```
Gly Val Glu Asn His Pro Ile His Leu His Gly Phe Asn Phe His Val
465                 470                 475                 480

Leu Ala Gln Gly Phe Gly Asn Tyr Asp Pro Val Asn Asp Pro Lys Lys
                485                 490                 495

Phe Asn Leu Ile Asn Pro Leu Ser Arg Asn Thr Ile Asn Val Pro Val
            500                 505                 510

Gly Gly Trp Gly Val Ile Arg Ile Thr Ala Asn Asn Pro Gly Val Trp
        515                 520                 525

Phe Phe His Cys His Leu Asp Val His Leu Pro Phe Gly Leu Ala Thr
    530                 535                 540

Ala Phe Val Val Glu Asn Gly Pro Thr Pro Glu Ser Thr Leu Pro Pro
545                 550                 555                 560

Pro Pro Val Asp Leu Pro Gln Cys
                565
```

<210> SEQ ID NO 46
<211> LENGTH: 567
<212> TYPE: PRT
<213> ORGANISM: Populus trichocarpa

<400> SEQUENCE: 46

```
Met Gly Ile Ser Arg Leu Gly Phe Ile Ala Gly Leu Ile Trp Phe Met
1               5                   10                  15

Ala Met Asp Trp Gln Gly Leu Cys Met Ala Gln Ser Asn Val His Arg
                20                  25                  30

Tyr Asn Phe Val Leu Gln Asn Ala Gln Phe Thr Arg Leu Cys Glu Thr
            35                  40                  45

Lys Thr Met Leu Thr Val Asn Gly Ser Phe Pro Gly Pro Thr Ile His
        50                  55                  60

Ala Arg Arg Gly Asp Thr Ile Tyr Val Asn Val His Asn Glu Gly Asp
65                  70                  75                  80

Tyr Gly Val Thr Ile His Trp His Gly Val Lys Gln Pro Arg Asn Pro
                85                  90                  95

Trp Ser Asp Gly Pro Glu Asn Ile Thr Gln Cys Pro Ile Gln Pro Gly
                100                 105                 110

Lys Asn Phe Thr Tyr Glu Ile Ile Leu Ser Asp Glu Glu Gly Thr Leu
            115                 120                 125

Trp Trp His Ala His Ser Asp Trp Thr Arg Ala Thr Val His Gly Ala
130                 135                 140

Ile Val Ile Ser Pro Ala Arg Gly Thr Thr Tyr Pro Phe Pro Ala Pro
145                 150                 155                 160

Tyr Ala Glu Gln Thr Ile Ile Ile Gly Ser Trp Phe Lys Gly Asp Val
                165                 170                 175

Lys Ala Val Ile Asp Asp Ala Leu Ala Thr Gly Gly Gly Pro Ala Ile
            180                 185                 190

Ser Asn Ser Leu Thr Ile Asn Gly Gln Pro Gly Asp Lys Tyr Pro Cys
        195                 200                 205

Ser Glu Glu Asn Thr Tyr Arg Leu Met Val Asn Ser Gly Arg Thr Tyr
210                 215                 220

Leu Leu Arg Val Ile Asn Ala Val Met Asn Glu Gln Phe Phe Gly
225                 230                 235                 240

Ile Ala Gly His Ser Leu Thr Val Val Gly Gln Asp Ala Ala Tyr Ile
                245                 250                 255

Lys Pro Ile Thr Thr Asn Tyr Ile Met Ile Thr Pro Gly Gln Thr Met
```

```
                    260                 265                 270
Asp Ile Leu Val Thr Ala Asn Arg Pro Arg Ser Tyr Tyr Ile Ala
            275                 280                 285

Ser His Ser Phe Ala Asp Gly Ala Gly Ile Ala Phe Asp Lys Thr Thr
        290                 295                 300

Thr Thr Ala Ile Phe Gln Tyr Asn Gly Asn Tyr Gly Arg Pro Ser Ser
305                 310                 315                 320

Ile Pro Leu Pro Val Leu Pro Ile Phe Asn Asp Thr Ala Ala Glu
            325                 330                 335

Asn Tyr Thr Ser Arg Val Arg Gly Leu Ala Ser Arg Asp His Pro Val
            340                 345                 350

Asn Val Pro Gln Thr Val Asn Arg Arg Leu Tyr Ile Thr Ile Ala Leu
            355                 360                 365

Asn Arg Leu Pro Cys Thr Glu Ala Thr Cys Thr Gly Pro Asn Arg Leu
        370                 375                 380

Phe Ala Ser Met Asn Asn Val Ser Phe Ala Ala Lys Pro Ile Asp Ile
385                 390                 395                 400

Leu Gln Ala Tyr Tyr Arg Ser Ile Asn Gly Val Phe Glu Ala Asp Phe
            405                 410                 415

Pro Ser Glu Pro Gln Lys Tyr Phe Asn Phe Thr Gly Asn Val Thr Ser
            420                 425                 430

Ile Asn Val Ala Thr Ala Arg Gly Thr Lys Val Thr Met Leu Asn Tyr
        435                 440                 445

Gly Glu Ala Val Glu Ile Val Phe Gln Gly Thr Asn Leu Leu Ala Glu
        450                 455                 460

Met Asn His Pro Ile His Leu His Gly Phe Ser Phe Tyr Leu Val Gly
465                 470                 475                 480

His Gly Lys Gly Asn Phe Asn Asn Glu Thr Asp Pro Lys Ser Tyr Asn
            485                 490                 495

Leu Ile Asp Pro Pro Glu Ile Asn Thr Val Ala Leu Pro Arg Ser Gly
        500                 505                 510

Trp Ala Ala Ile Arg Phe Val Ala Asn Asn Pro Gly Val Trp Phe Ile
            515                 520                 525

His Cys His Leu Glu Lys His Ser Ser Trp Gly Met Asp Thr Val Leu
        530                 535                 540

Ile Val Arg Asn Gly Arg Thr Arg Ala Gln Ser Met Arg Pro Pro
545                 550                 555                 560

Ala Thr Leu Pro Ser Cys Ser
            565

<210> SEQ ID NO 47
<211> LENGTH: 567
<212> TYPE: PRT
<213> ORGANISM: Populus trichocarpa

<400> SEQUENCE: 47

Met Gly Ile Ser Arg Leu Gly Phe Ile Ala Gly Leu Ile Trp Phe Met
1               5                   10                  15

Ala Met Asp Trp Gln Gly Leu Cys Met Ala Gln Ser Ser Val His Arg
            20                  25                  30

Tyr Asn Phe Val Leu Gln Asn Ala Gln Phe Thr Arg Leu Cys Glu Thr
        35                  40                  45

Lys Thr Met Leu Thr Val Asn Gly Ser Phe Pro Gly Pro Thr Ile His
    50                  55                  60
```

```
Ala Arg Arg Gly Asp Thr Ile Tyr Val Asn Val His Asn Glu Gly Asp
 65                  70                  75                  80

Tyr Gly Val Thr Ile His Trp His Gly Val Lys Gln Pro Arg Asn Pro
                 85                  90                  95

Trp Ser Asp Gly Pro Glu Asn Ile Thr Gln Cys Pro Ile Gln Pro Gly
            100                 105                 110

Lys Asn Phe Thr Tyr Glu Ile Ile Leu Ser Asp Glu Gly Thr Leu
        115                 120                 125

Trp Trp His Ala His Ser Asp Trp Thr Arg Ala Thr Val His Gly Ala
130                 135                 140

Ile Val Ile Ser Pro Ala Arg Gly Thr Thr Tyr Pro Phe Pro Ala Pro
145                 150                 155                 160

Tyr Ala Glu Gln Thr Ile Ile Ile Gly Ser Trp Phe Lys Arg Asp Val
                165                 170                 175

Lys Ala Val Ile Asp Glu Val Leu Ala Thr Gly Val Gly Pro Ala Pro
            180                 185                 190

Ser Asn Ser Leu Thr Ile Asn Gly Gln Pro Gly Asp Leu Tyr Pro Cys
        195                 200                 205

Ser Glu Glu Asn Thr Tyr Arg Leu Lys Val Asn Ser Gly Arg Thr Tyr
210                 215                 220

Leu Leu Arg Val Ile Asn Ala Val Met Asn Glu Glu Gln Phe Phe Gly
225                 230                 235                 240

Ile Ala Gly His Ser Leu Thr Val Val Gly Gln Asp Ala Ala Tyr Ile
                245                 250                 255

Lys Pro Ile Thr Thr Asn Tyr Ile Met Ile Thr Pro Gly Gln Thr Met
            260                 265                 270

Asp Ile Leu Val Thr Ala Asn Gln Pro Pro Ser Tyr Tyr Tyr Ile Ala
        275                 280                 285

Ser Tyr Ser Phe Ser Asp Gly Ala Gly Val Ala Phe Asp Glu Thr Thr
290                 295                 300

Thr Thr Ala Ile Phe Gln Tyr Asn Gly Asn Tyr Ser Arg Pro Ser Ala
305                 310                 315                 320

Ile Pro Leu Pro Val Leu Pro Val Phe Asn Asp Thr Ala Ala Ala Glu
                325                 330                 335

Asn Tyr Thr Ser Arg Val Arg Gly Leu Ala Ser Arg Asp His Pro Val
            340                 345                 350

Asn Val Pro Gln Thr Ile Asn Arg Arg Leu Tyr Ile Ala Ile Ala Leu
        355                 360                 365

Asn Asn Leu Ser Cys Thr Glu Ala Thr Cys Ile Asn Ser Thr Arg Leu
370                 375                 380

Ala Ala Ser Met Asn Asn Val Ser Phe Ala Ala Lys Pro Ile Asp Ile
385                 390                 395                 400

Leu Gln Ala Tyr Tyr Arg Ser Ile Asn Gly Val Phe Asp Ala Asp Phe
                405                 410                 415

Pro Ser Glu Pro Gln Lys Tyr Phe Asn Phe Thr Gly Asn Val Thr Ser
            420                 425                 430

Ile Asn Val Ile Thr Ala Arg Gly Thr Lys Val Thr Met Leu Asn Tyr
        435                 440                 445

Gly Glu Ala Val Glu Ile Val Phe Gln Gly Thr Asn Leu Leu Ala Glu
450                 455                 460

Met Asn His Pro Ile His Leu His Gly Phe Ser Phe Tyr Leu Val Gly
465                 470                 475                 480

His Gly Lys Gly Asn Phe Asn Asn Glu Thr Asp Pro Lys Ser Tyr Asn
```

```
            485                 490                 495
Leu Ile Asp Pro Pro Glu Ile Asn Thr Val Ala Leu Pro Arg Ser Gly
            500                 505                 510

Trp Ala Ala Ile Arg Phe Val Ala Asn Asn Pro Gly Val Trp Phe Ile
            515                 520                 525

His Cys His Leu Glu Lys His Ser Ser Trp Gly Met Asp Thr Val Leu
            530                 535                 540

Ile Val Arg Asn Gly Arg Thr Arg Glu Gln Ser Met Arg Pro Pro Pro
545                 550                 555                 560

Ala Thr Leu Pro Ser Cys Ser
            565

<210> SEQ ID NO 48
<211> LENGTH: 576
<212> TYPE: PRT
<213> ORGANISM: Populus trichocarpa

<400> SEQUENCE: 48

Met Glu Thr His Asn Leu Thr Val Lys Gln Leu Tyr Cys Cys Leu Leu
1               5                   10                  15

Leu Ser Ile Phe Val Ile Ser Phe Gln Ala Ser Ser Ser Glu Pro
            20                  25                  30

Glu Thr His Tyr His Glu Phe Val Ile Gln Ala Lys Pro Val Arg Arg
            35                  40                  45

Leu Cys Arg Thr His Asn Thr Ile Thr Val Asn Gly Leu Phe Pro Gly
            50                  55                  60

Pro Thr Leu Glu Val Arg Asp Gly Asp Thr Leu Val Ile Lys Ala Ile
65                  70                  75                  80

Asn Asn Ala Arg Tyr Asn Val Thr Leu His Trp His Gly Val Arg Gln
            85                  90                  95

Leu Arg Asn Pro Trp Ala Asp Gly Pro Asp Arg Val Thr Gln Cys Pro
            100                 105                 110

Ile Gln Pro Gly Arg Ser Tyr Thr Tyr Arg Phe Thr Ile Glu Asn Gln
            115                 120                 125

Glu Gly Thr Leu Trp Trp His Ala His Ser Arg Trp Leu Arg Ala Thr
            130                 135                 140

Val Tyr Gly Ala Leu Ile Ile His Pro Lys Leu Gly Ser Pro Tyr Ser
145                 150                 155                 160

Phe Pro Met Pro Ile Arg Glu Ile Pro Ile Leu Leu Gly Glu Trp Trp
            165                 170                 175

Val Arg Asn Pro Met Asp Val Leu Arg Leu Ala Asp Phe Thr Gly Ala
            180                 185                 190

Ala Pro Asn Val Ser Asp Ala Tyr Thr Ile Asn Gly Gln Pro Gly Asp
            195                 200                 205

Leu Tyr Arg Cys Ser Lys Gln Glu Thr Val Arg Phe Pro Val Asp Pro
            210                 215                 220

Gly Glu Thr Ile Leu Leu Arg Val Ile Asn Ser Ala Met Asn Gln Glu
225                 230                 235                 240

Leu Phe Phe Ala Val Ala Asn His Ile Leu Thr Val Val Ala Val Asp
            245                 250                 255

Ala Ala Cys Thr Met Pro Phe Ala Thr Ser Phe Ile Met Ile Ala Pro
            260                 265                 270

Gly Gln Thr Thr Asn Val Leu Leu Thr Ala Asp Gln Thr Pro Gly His
            275                 280                 285
```

```
Tyr Tyr Met Ala Ala His Ala Tyr Asn Ser Ala Asn Ala Pro Phe Asp
    290                 295                 300

Asn Thr Thr Thr Thr Ala Ile Leu Glu Tyr Lys Ser Ala Pro Cys Asn
305                 310                 315                 320

Ala Asn Lys Gly Lys Ser Ser Thr Pro Ile Phe Pro Gln Leu Pro Gly
            325                 330                 335

Phe Asn Asp Thr Asn Ser Ala Ile Ala Phe Thr Ser Ser Leu Arg Ser
            340                 345                 350

Pro Ser Lys Val Asn Val Pro Leu Gln Ile Asp Glu Asn Leu Phe Phe
            355                 360                 365

Thr Val Gly Phe Gly Leu Ile Asn Cys Thr Asn Pro Asn Ser Pro Arg
370                 375                 380

Cys Gln Gly Pro Asn Gly Thr Arg Phe Ala Ala Ser Ile Asn Asn Val
385                 390                 395                 400

Ser Phe Val Leu Pro Thr Arg Asn Ser Leu Met Gln Ala Tyr Tyr Gln
                405                 410                 415

Gly Gln Pro Gly Val Phe Thr Thr Asp Phe Pro Val Pro Pro Val
            420                 425                 430

Lys Phe Asp Tyr Thr Gly Asn Val Ser Arg Gly Leu Trp Gln Pro Val
            435                 440                 445

Lys Ala Thr Lys Leu Tyr Lys Leu Lys Phe Gly Ala Lys Val Gln Ile
450                 455                 460

Val Phe Gln Asp Thr Ser Ile Val Thr Val Glu Asp His Pro Met His
465                 470                 475                 480

Leu His Gly His Asn Phe Ala Val Val Gly Ser Gly Phe Gly Asn Phe
                485                 490                 495

Asn Pro Gln Thr Asp Pro Ala Lys Phe Asn Leu Ile Asn Pro Pro Tyr
            500                 505                 510

Arg Asn Thr Ile Gly Asn Pro Pro Gly Gly Trp Val Ala Ile Arg Phe
            515                 520                 525

Val Ala Asp Asn Pro Gly Ile Trp Leu Leu His Cys His Leu Asp Ser
530                 535                 540

His Leu Asn Trp Gly Leu Ala Met Ala Phe Leu Val Glu Asn Gly Val
545                 550                 555                 560

Gly Asn Leu Gln Ser Val Gln Pro Pro Leu Asp Leu Pro Gln Cys
            565                 570                 575

<210> SEQ ID NO 49
<211> LENGTH: 562
<212> TYPE: PRT
<213> ORGANISM: Populus trichocarpa

<400> SEQUENCE: 49

Met Leu Arg Leu Leu Phe Leu Leu Thr Cys Ala Leu Ala Leu Leu Ala
1               5                   10                  15

Ser Ser Val Ala Ser Ala Ala Ile Val Glu His Ser Phe Tyr Val Lys
                20                  25                  30

Asn Leu Thr Val Arg Arg Leu Cys Ser Glu Gln Val Val Thr Ala Val
            35                  40                  45

Asn Gly Ser Leu Pro Gly Pro Thr Leu Arg Val Arg Glu Gly Asp Thr
        50                  55                  60

Leu Ile Val His Val Phe Asn Lys Ser Pro Tyr Asn Leu Thr Ile His
65                  70                  75                  80

Trp His Gly Val Phe Gln Leu Leu Ser Ala Trp Ala Asp Gly Pro Ser
                85                  90                  95
```

```
Met Val Thr Gln Cys Pro Ile Thr Pro Gly Lys Tyr Thr Tyr Lys
            100                 105                 110

Phe Lys Leu Leu Gln Gln Glu Gly Thr Leu Trp Trp His Ala His Phe
            115                 120                 125

Ser Leu Leu Arg Ala Thr Val Tyr Gly Ala Leu Ile Ile Arg Pro Arg
            130                 135                 140

Ser Gly His Pro Tyr Pro Phe Pro Lys Pro Asn Lys Glu Val Pro Ile
145                 150                 155                 160

Leu Leu Gly Glu Trp Trp Asn Gly Asp Val Val Gly Ile Glu Arg Lys
                165                 170                 175

Ala Ala Ala Thr Gly Ala Ser Pro Lys Ile Ser Asp Ala Tyr Thr Ile
            180                 185                 190

Asn Gly Leu Pro Gly Asp Leu Tyr Asn Cys Ser Gln Asp Arg Met Tyr
            195                 200                 205

Lys Leu Lys Val Gln Lys Gly Lys Thr Tyr Leu Leu Arg Ile Ile Asn
            210                 215                 220

Ala Ala Leu Asp Asn Gln Leu Phe Phe Met Ile Ala Asn His Asn Met
225                 230                 235                 240

Thr Val Val Ala Val Asp Ala Gly Tyr Thr Val Pro Tyr Val Thr Asp
                245                 250                 255

Val Val Val Thr Gly Pro Gly Gln Thr Val Asp Val Leu Leu Ala Ala
            260                 265                 270

Asp Gln Glu Val Gly Ser Tyr Phe Met Ala Ala Asn Ser Tyr Ala Ser
            275                 280                 285

Ala Arg Pro Ala Ala Pro Phe Asp Asn Thr Thr Thr Arg Gly Ile Val
            290                 295                 300

Val Tyr Glu Gly Ala Pro Thr Ser Ala Thr Pro Ile Met Pro Arg Met
305                 310                 315                 320

Pro Ala Phe Asn Asp Thr Pro Thr Ala His Lys Phe Phe Thr Ser Ile
                325                 330                 335

Thr Gly Leu Ala Gly Gly Pro His Trp Val Pro Val Pro Arg Gln Ile
            340                 345                 350

Asp Glu His Met Phe Val Thr Val Gly Leu Gly Leu Ser Ile Cys Pro
            355                 360                 365

Thr Cys Ser Asn Gly Thr Arg Leu Ser Ala Ser Met Asn Asn Phe Ser
370                 375                 380

Phe Ala Arg Pro Ser Ser Leu Ser Met Leu Gln Ala Phe Phe Asn
385                 390                 395                 400

Val Ser Gly Ile Tyr Thr Pro Asp Phe Pro Asp Thr Pro Ile Lys
                405                 410                 415

Phe Asp Tyr Thr Asn Ala Ile Asn Ala Gln Asn Leu Ser Leu Leu Phe
            420                 425                 430

Thr Pro Lys Ser Thr Ser Val Lys Val Leu Lys Tyr Asn Ala Thr Val
            435                 440                 445

Glu Met Val Leu Gln Asn Thr Ala Phe Leu Gly Val Glu Asn His Pro
450                 455                 460

Ile His Leu His Gly Phe Thr Phe His Val Leu Ala Gln Gly Phe Gly
465                 470                 475                 480

Asn Tyr Asp Pro Val Asn Asp His Lys Asn Phe Asn Leu Ile Asn Pro
                485                 490                 495

Leu Ser Arg Asn Thr Ile Asn Val Pro Val Gly Gly Trp Ala Val Ile
            500                 505                 510
```

```
Arg Phe Thr Ala Asn Asn Pro Gly Val Trp Phe Phe His Cys His Leu
            515                 520                 525
Glu Ala His Leu Ser Met Gly Leu Ala Thr Ala Phe Val Val Glu Asn
    530                 535                 540
Gly Pro Thr Pro Glu Ser Thr Leu Pro Pro Pro Val Asp Leu Pro
545                 550                 555                 560
Gln Cys

<210> SEQ ID NO 50
<211> LENGTH: 569
<212> TYPE: PRT
<213> ORGANISM: Populus trichocarpa

<400> SEQUENCE: 50

Met Leu Arg Leu Leu Phe Leu Leu Thr Cys Ala Leu Ala Leu Leu Ala
1               5                   10                  15
Ser Ser Val Ala Ser Ala Ala Ile Val Glu Arg Ser Phe Tyr Val Lys
            20                  25                  30
Asn Leu Thr Val Arg Arg Leu Cys Ser Glu Gln Val Val Thr Ala Val
        35                  40                  45
Asn Gly Ser Leu Pro Gly Pro Thr Leu Arg Val Arg Glu Gly Asp Thr
50                  55                  60
Leu Ile Val His Val Phe Asn Lys Ser Pro Tyr Asp Leu Ser Ile His
65                  70                  75                  80
Trp His Gly Val Phe Gln Leu Ser Ala Trp Ala Asp Gly Pro Ser
                85                  90                  95
Met Val Thr Gln Cys Pro Ile Thr Pro Gly Gly Lys Tyr Thr Tyr Lys
            100                 105                 110
Phe Lys Leu Leu Gln Gln Glu Gly Thr Leu Trp Trp His Ala His Phe
        115                 120                 125
Ser Leu Leu Arg Ala Thr Val Tyr Gly Ala Leu Ile Ile Arg Pro Arg
130                 135                 140
Ser Gly His Pro Tyr Pro Phe Pro Lys Pro Asn Lys Glu Ile Pro Ile
145                 150                 155                 160
Leu Leu Gly Glu Trp Trp Asn Ala Asp Val Val Gly Ile Glu Arg Glu
                165                 170                 175
Ala Ala Ala Thr Gly Ala Pro Pro Lys Ile Ser Asp Ala Tyr Thr Ile
            180                 185                 190
Asn Gly Leu Pro Gly Asp Leu Tyr Asn Cys Ser Gln Asn Arg Met Tyr
        195                 200                 205
Lys Leu Lys Val Gln Lys Gly Lys Thr Tyr Leu Leu Arg Ile Ile Asn
210                 215                 220
Ala Ala Leu Asp Asn Gln Leu Phe Phe Lys Ile Ala Asn His Asn Met
225                 230                 235                 240
Thr Val Val Ala Val Asp Ala Gly Tyr Thr Val Pro Tyr Val Thr Asp
                245                 250                 255
Val Val Val Thr Gly Pro Gly Gln Thr Val Asp Val Leu Leu Ala Ala
            260                 265                 270
Asp Gln Glu Val Gly Ser Tyr Phe Met Ala Ala Asn Ala Tyr Ala Ser
        275                 280                 285
Ala Gly Pro Ala Pro Pro Ala Phe Pro Ala Pro Pro Phe Asp Asn
290                 295                 300
Thr Thr Thr Arg Gly Ile Val Val Tyr Glu Gly Ala Pro Thr Ser Ala
305                 310                 315                 320
```

```
Thr Pro Ile Met Pro Leu Met Pro Ala Phe Thr Asp Thr Pro Thr Ala
            325                 330                 335

His Lys Phe Phe Thr Ser Ile Thr Gly Leu Ala Gly Gly Pro His Trp
        340                 345                 350

Val Pro Val Pro Arg His Ile Asp Glu His Met Phe Val Thr Val Gly
            355                 360                 365

Leu Gly Leu Ser Ile Cys Pro Thr Cys Leu Asn Gly Thr Arg Leu Ser
        370                 375                 380

Ala Ser Met Asn Asn Phe Ser Phe Ala Arg Pro Ser Ser Leu Ser Met
385                 390                 395                 400

Leu Gln Ala Phe Phe Asn Val Ser Gly Ile Tyr Thr Pro Asp Phe
            405                 410                 415

Pro Asp Thr Pro Pro Val Lys Phe Asp Tyr Thr Asn Val Ile Asn Ala
            420                 425                 430

Val Asn Pro Ser Leu Leu Ile Thr Pro Lys Ser Thr Ser Val Lys Val
        435                 440                 445

Leu Lys Tyr Asn Ala Thr Val Glu Met Val Leu Gln Asn Thr Ala Leu
    450                 455                 460

Leu Gly Val Glu Asn His Pro Ile His Leu His Gly Phe Asn Phe His
465                 470                 475                 480

Met Leu Ala Gln Gly Phe Gly Asn Tyr Asp Pro Val Asn Asp Pro Lys
            485                 490                 495

Lys Phe Asn Leu Ile Asn Pro Leu Ser Arg Asn Thr Ile Asn Val Pro
        500                 505                 510

Val Gly Gly Trp Gly Val Ile Arg Phe Thr Ala Asn Asn Pro Gly Val
    515                 520                 525

Trp Phe Ile His Cys His Leu Glu Ala His Leu Pro Met Gly Leu Ala
530                 535                 540

Thr Ala Phe Val Val Glu Asn Gly Pro Thr Pro Glu Ser Thr Leu Pro
545                 550                 555                 560

Pro Pro Pro Val Asp Leu Pro Gln Cys
            565

<210> SEQ ID NO 51
<211> LENGTH: 576
<212> TYPE: PRT
<213> ORGANISM: Populus trichocarpa

<400> SEQUENCE: 51

Met Glu Thr His Asn Leu Thr Val Lys Gln Leu Tyr Cys Cys Leu Leu
1               5                   10                  15

Leu Ser Ile Phe Val Ile Ile Ser Phe Gln Ala Ser Ser Ser Glu Pro
            20                  25                  30

Glu Thr His Tyr His Glu Phe Val Ile Gln Ala Lys Pro Val Arg Arg
        35                  40                  45

Leu Cys Arg Thr His Asn Thr Ile Thr Val Asn Gly Leu Phe Pro Gly
    50                  55                  60

Pro Thr Leu Glu Val Arg Asp Gly Asp Thr Leu Val Ile Lys Ala Ile
65                  70                  75                  80

Asn Asn Ala Arg Tyr Asn Val Thr Leu His Trp His Gly Val Arg Gln
            85                  90                  95

Leu Arg Asn Pro Trp Ala Asp Gly Pro Asp Arg Val Thr Gln Cys Pro
        100                 105                 110

Ile Gln Pro Gly Arg Ser Tyr Thr Tyr Arg Phe Thr Ile Glu Asn Gln
    115                 120                 125
```

Glu Gly Thr Leu Trp Trp His Ala His Ser Arg Trp Leu Arg Ala Thr
    130             135                 140

Val Tyr Gly Ala Leu Ile Ile His Pro Lys Leu Gly Ser Pro Tyr Ser
145             150                 155                 160

Phe Pro Met Pro Ile Arg Glu Ile Pro Ile Leu Leu Gly Glu Trp Trp
            165                 170                 175

Val Arg Asn Pro Met Asp Val Leu Arg Leu Ala Asp Phe Thr Gly Ala
            180                 185                 190

Ala Pro Asn Val Ser Asp Ala Tyr Thr Ile Asn Gly Gln Pro Gly Asp
            195                 200                 205

Leu Tyr Arg Cys Ser Lys Gln Glu Thr Val Arg Phe Pro Val Asp Pro
    210                 215                 220

Gly Glu Thr Ile Leu Leu Arg Val Ile Asn Ser Ala Met Asn Gln Glu
225             230                 235                 240

Leu Phe Phe Ala Val Ala Asn His Ile Leu Thr Val Val Ala Val Asp
                245                 250                 255

Ala Ala Cys Thr Met Pro Phe Ala Thr Ser Phe Ile Met Ile Ala Pro
            260                 265                 270

Gly Gln Thr Thr Asn Val Leu Leu Thr Ala Asp Gln Thr Pro Gly His
            275                 280                 285

Tyr Tyr Met Ala Ala His Ala Tyr Asn Ser Ala Asn Ala Pro Phe Asp
    290                 295                 300

Asn Thr Thr Thr Thr Ala Ile Leu Glu Tyr Lys Ser Ala Pro Cys Asn
305                 310                 315                 320

Ala Asn Lys Gly Lys Ser Ser Thr Pro Ile Phe Pro Gln Leu Pro Gly
            325                 330                 335

Phe Asn Asp Thr Asn Ser Ala Ile Ala Phe Thr Ser Ser Leu Arg Ser
            340                 345                 350

Pro Ser Lys Val Asn Val Pro Leu Gln Ile Asp Glu Asn Leu Phe Phe
    355                 360                 365

Thr Val Gly Phe Gly Leu Ile Asn Cys Thr Asn Pro Asn Ser Pro Arg
370             375                 380

Cys Gln Gly Pro Asn Gly Thr Arg Phe Ala Ala Ser Ile Asn Asn Val
385             390                 395                 400

Ser Phe Val Leu Pro Thr Arg Asn Ser Leu Met Gln Ala Tyr Tyr Gln
            405                 410                 415

Gly Gln Pro Gly Val Phe Thr Thr Asp Phe Pro Val Pro Pro Val
            420                 425                 430

Lys Phe Asp Tyr Thr Gly Asn Val Ser Arg Gly Leu Trp Gln Pro Val
    435                 440                 445

Lys Ala Thr Lys Leu Tyr Lys Leu Lys Phe Gly Ala Lys Val Gln Ile
450                 455                 460

Val Phe Gln Asp Thr Ser Thr Val Thr Val Glu Asp His Pro Met His
465                 470                 475                 480

Leu His Gly His Asn Phe Ala Val Val Gly Ser Gly Phe Gly Asn Phe
                485                 490                 495

Asn Pro Gln Thr Asp Pro Ala Lys Phe Asn Leu Ile Asn Pro Pro Tyr
            500                 505                 510

Arg Asn Thr Ile Gly Asn Pro Pro Gly Gly Trp Val Ala Ile Arg Phe
    515                 520                 525

Val Ala Asp Asn Pro Gly Ile Trp Leu Leu His Cys His Leu Asp Ser
530                 535                 540

```
His Leu Asn Trp Gly Leu Ala Met Ala Phe Leu Val Glu Asn Gly Val
545                 550                 555                 560

Gly Asn Leu Gln Ser Val Gln Pro Pro Leu Asp Leu Pro Gln Cys
                565                 570                 575

<210> SEQ ID NO 52
<211> LENGTH: 569
<212> TYPE: PRT
<213> ORGANISM: Populus trichocarpa

<400> SEQUENCE: 52

Met Leu Arg Leu Leu Phe Leu Leu Thr Cys Ala Leu Ala Leu Leu Ala
1               5                   10                  15

Ser Ser Val Ala Ser Ala Ala Ile Val Glu Arg Ser Phe Tyr Val Lys
            20                  25                  30

Asn Leu Thr Leu Arg Arg Leu Cys Ser Glu Gln Val Val Thr Ala Val
        35                  40                  45

Asn Gly Ser Leu Pro Gly Pro Thr Leu Arg Val Arg Glu Gly Asp Thr
    50                  55                  60

Leu Ile Val His Val Phe Asn Lys Ser Pro Tyr Asp Leu Ser Ile His
65                  70                  75                  80

Trp His Gly Val Phe Gln Leu Leu Ser Ala Trp Ala Asp Gly Pro Ser
                85                  90                  95

Met Val Thr Gln Cys Pro Ile Thr Pro Gly Gly Lys Tyr Thr Tyr Lys
            100                 105                 110

Phe Lys Leu Leu Gln Gln Glu Gly Thr Leu Trp Trp His Ala His Phe
        115                 120                 125

Ser Leu Leu Arg Ala Thr Val Tyr Gly Ala Leu Ile Ile Arg Pro Arg
130                 135                 140

Ser Gly His Pro Tyr Pro Phe Pro Lys Pro Asn Lys Glu Ile Pro Ile
145                 150                 155                 160

Leu Leu Gly Glu Trp Trp Asn Ala Asp Val Val Gly Ile Glu Arg Lys
                165                 170                 175

Ala Ala Ala Thr Gly Ala Pro Pro Lys Ile Ser Asp Ala Tyr Thr Ile
            180                 185                 190

Asn Gly Leu Pro Gly Asp Leu Tyr Asn Cys Ser Gln Asn Arg Met Tyr
        195                 200                 205

Lys Leu Lys Val Gln Lys Gly Lys Thr Tyr Leu Leu Arg Ile Ile Asn
210                 215                 220

Ala Ala Leu Asp Asn Gln Leu Phe Phe Lys Ile Ala Asn His Asn Met
225                 230                 235                 240

Thr Val Val Ala Val Asp Ala Gly Tyr Thr Val Pro Tyr Val Thr Asp
                245                 250                 255

Val Val Val Thr Gly Pro Gly Gln Thr Val Asp Val Leu Leu Ala Ala
            260                 265                 270

Asp Gln Glu Val Gly Ser Tyr Phe Met Ala Ala Asn Ala Tyr Ala Ser
        275                 280                 285

Ala Gly Pro Ala Pro Pro Ala Phe Pro Ala Pro Pro Phe Asp Asn
290                 295                 300

Thr Thr Thr Arg Gly Ile Val Val Tyr Glu Gly Ala Pro Thr Ser Ala
305                 310                 315                 320

Thr Pro Ile Met Pro Leu Met Pro Ala Phe Thr Asp Thr Pro Thr Ala
                325                 330                 335

His Lys Phe Phe Thr Ser Ile Thr Gly Leu Ala Gly Gly Pro His Trp
            340                 345                 350
```

Val Pro Val Pro Arg His Ile Asp Glu His Met Phe Val Thr Val Gly
            355                 360                 365

Leu Gly Leu Ser Ile Cys Pro Thr Cys Leu Asn Gly Thr Arg Leu Ser
        370                 375                 380

Ala Ser Met Asn Asn Phe Ser Phe Ala Arg Pro Ser Ser Leu Ser Met
385                 390                 395                 400

Leu Gln Ala Phe Phe Phe Asn Val Ser Gly Ile Tyr Thr Pro Asp Phe
            405                 410                 415

Pro Asp Thr Pro Pro Val Lys Phe Asp Tyr Thr Asn Val Ile Asn Ala
            420                 425                 430

Val Asn Pro Ser Leu Leu Ile Thr Pro Lys Ser Thr Ser Val Lys Val
            435                 440                 445

Leu Lys Tyr Asn Ala Thr Val Glu Met Val Leu Gln Asn Thr Ala Leu
            450                 455                 460

Leu Gly Val Glu Asn His Pro Ile His Leu His Gly Phe Asn Phe His
465                 470                 475                 480

Val Leu Ala Gln Gly Phe Gly Asn Tyr Asp Pro Val Asn Asp Pro Lys
            485                 490                 495

Lys Phe Asn Leu Ile Asn Pro Leu Ser Arg Asn Thr Ile Asn Val Pro
            500                 505                 510

Val Gly Gly Trp Gly Val Ile Arg Phe Thr Ala Asn Asn Pro Gly Val
            515                 520                 525

Trp Phe Ile His Cys His Leu Glu Ala His Leu Pro Met Gly Leu Ala
            530                 535                 540

Thr Ala Phe Val Val Glu Asn Gly Pro Thr Pro Glu Ser Thr Leu Pro
545                 550                 555                 560

Pro Pro Pro Val Asp Leu Pro Gln Cys
            565

<210> SEQ ID NO 53
<211> LENGTH: 559
<212> TYPE: PRT
<213> ORGANISM: Populus trichocarpa

<400> SEQUENCE: 53

Met Val Lys Ile Leu Arg Leu Leu Gly Phe Ile Val Ser Leu Ile Ile
1               5                   10                  15

Gln Asn Tyr Thr Thr Ala Asn Gly Lys Ile His His Lys Phe Val
            20                  25                  30

Val Lys Ser Ala Ser Phe Thr Arg Leu Cys Asn Thr Lys Glu Ile Leu
        35                  40                  45

Thr Val Asn Gly Lys Phe Pro Gly Pro Thr Leu Glu Ala Tyr Thr Gly
    50                  55                  60

Asp Glu Leu Ile Val Thr Val Tyr Asn Arg Ala Lys Tyr Asn Ile Thr
65                  70                  75                  80

Leu His Trp His Gly Ala Arg Gln Val Arg Asn Pro Trp Ser Asp Gly
            85                  90                  95

Pro Glu Tyr Ile Thr Gln Cys Pro Ile Gln Pro Gly Arg Arg Phe Asn
            100                 105                 110

Tyr Lys Ile Thr Leu Thr Thr Glu Glu Gly Thr Ile Trp Trp His Ala
            115                 120                 125

His Asn Ser Trp Ala Arg Ala Thr Val His Gly Ala Leu Ile Ile Tyr
            130                 135                 140

Pro Lys His Gly Ser His Tyr Pro Phe Pro Lys Pro His Ala Glu Phe

```
            145                 150                 155                 160
        Gly Glu Trp Trp Lys Lys Asp Val Met Lys Ile Pro Gly Asp Ala Asn
                        165                 170                 175

Ile Thr Gly Gly Glu Pro Thr Leu Ser Ala Ala Phe Thr Ile Asn Gly
                        180                 185                 190

Glu Pro Gly Tyr Met Tyr Pro Cys Ser Lys Ala Gly Thr Phe Lys Met
                        195                 200                 205

Met Val Glu Gln Gly Lys Thr Tyr Leu Leu Arg Ile Ile Asn Ala Val
        210                 215                 220

Leu Asp Glu Asn Leu Phe Phe Ser Ile Ala Lys His Lys Leu Thr Ile
        225                 230                 235                 240

Val Gly Lys Asp Gly Cys Tyr Leu Lys Pro Phe Thr Ser Asp Tyr Leu
                        245                 250                 255

Met Ile Thr Pro Gly Gln Thr Met Asp Val Leu Phe Glu Ala Asn Gln
                        260                 265                 270

Pro Pro Ser His Tyr Ser Met Ala Ser Arg Ala Tyr Ser Ser Ala Phe
                        275                 280                 285

Gly Ala Gly Phe Asp Asn Thr Thr Thr Ala Ile Val Glu Tyr His
                        290                 295                 300

Gly Ile Tyr His Leu Pro Lys Ser Pro His Phe Ser Pro Leu Pro Pro
        305                 310                 315                 320

Tyr Asn Arg Thr Gln Ala Ser Thr Asp Phe Thr Lys Gln Phe Arg Ser
                        325                 330                 335

Pro Val Lys Ala His Val Pro Gln Lys Val Asp Thr Arg Leu Phe Phe
                        340                 345                 350

Thr Ile Ser Val Asn Leu Leu Asn Cys Ser Thr Asp Lys Pro Cys Ala
                        355                 360                 365

Gly Pro Phe Gly Lys Arg Phe Ala Ala Ser Met Asn Asn Ile Ser Phe
                        370                 375                 380

Val Asn Pro Pro Ser Leu Asp Ile Leu Gln Ala Tyr Tyr Tyr Gly Val
        385                 390                 395                 400

Ala Gly Val Phe Glu Arg Asn Phe Pro Arg Lys Pro Pro Asn Glu Phe
                        405                 410                 415

Asn Tyr Thr Ala Glu Asn Leu Pro Ala Asn Leu Leu Thr Pro Ser Phe
                        420                 425                 430

Gly Thr Glu Val Arg Val Leu Lys Tyr Asn Ala Ser Val Glu Ile Ile
                        435                 440                 445

Leu Gln Gly Thr Asn Val Leu Ala Ala Asp Asn His Pro Ile His Leu
        450                 455                 460

His Gly Tyr Ser Phe Tyr Val Val Gly Trp Gly Phe Gly Asn Phe Asp
        465                 470                 475                 480

Pro Ser Lys Asp Pro Ser Arg Tyr Asn Leu Val Asp Pro Pro Glu Glu
                        485                 490                 495

Thr Thr Val Gly Val Pro His Asn Gly Trp Ala Ala Ile Arg Phe Arg
                        500                 505                 510

Ala Asp Asn Pro Gly Val Trp Leu Leu His Cys His Ile Glu Arg His
                        515                 520                 525

Val Thr Trp Gly Met Gly Met Val Phe Leu Val Lys Asn Gly Val Ser
                        530                 535                 540

Ser Gln Ala Arg Ile Leu Lys Pro Pro Arg Asp Leu Pro Arg Cys
        545                 550                 555

<210> SEQ ID NO 54
```

<211> LENGTH: 566
<212> TYPE: PRT
<213> ORGANISM: Populus trichocarpa

<400> SEQUENCE: 54

```
Met Met Ala Ile Asn Arg Val Leu Ala Phe Gln Ile Leu Arg Phe Leu
1               5                   10                  15

Leu Phe Gly Gly Phe Leu Cys Cys Gln Ala Ile Val His His Thr Phe
            20                  25                  30

Val Val Lys Asp Val Pro Tyr Thr Arg Leu Cys Ser Thr Lys Asn Ile
        35                  40                  45

Met Thr Val Asn Gly Gln Phe Pro Gly Pro Thr Leu Tyr Val Thr Lys
    50                  55                  60

Gly Glu Thr Ile Ile Val Asp Val Ile Asn Lys Ser Pro His Asn Ile
65                  70                  75                  80

Thr Ile His Trp His Gly Val Lys Gln Pro Lys Tyr Pro Trp Ser Asp
                85                  90                  95

Gly Pro Glu Tyr Ile Thr Gln Cys Pro Ile Gln Pro Gly Gly Lys Phe
            100                 105                 110

Ser Gln Arg Val Ile Phe Ser Asn Glu Glu Gly Thr Leu Trp Trp His
        115                 120                 125

Ala His Ser Asp Trp Thr Arg Ala Thr Val Tyr Gly Ala Ile Val Ile
    130                 135                 140

Tyr Pro Lys Lys Gly Thr Glu Tyr Pro Phe Pro Met Pro His Ala Asp
145                 150                 155                 160

Val Pro Ile Ile Leu Gly Glu Trp Trp Lys Lys Asp Ile Phe Glu Ile
                165                 170                 175

Phe Asp Gln Phe Arg Ala Ser Gly Ala Asp Pro Asp Val Ser Asp Ala
            180                 185                 190

Tyr Thr Ile Asn Gly Gln Pro Gly Asp Leu Tyr Pro Cys Ser Lys Ser
        195                 200                 205

Asp Thr Phe Lys Leu Ser Val Asp Tyr Gly Lys Thr Tyr Leu Leu Arg
    210                 215                 220

Leu Ile Asn Ala Ala Leu Gln Asp Ile Leu Phe Phe Ser Ile Thr Asn
225                 230                 235                 240

His Gln Val Thr Val Val Gly Thr Asp Ala Ser Tyr Thr Lys Pro Leu
                245                 250                 255

Lys Val Asp Tyr Ile Ala Ile Ser Pro Gly Gln Thr Ile Asp Val Leu
            260                 265                 270

Leu Glu Ala Asn Gln Pro Leu Asp His Tyr Tyr Met Ala Ala Lys Val
        275                 280                 285

Tyr Ser Ser Ala Asn Gly Val Gln Tyr Asp Asn Thr Thr Ala Thr Ala
    290                 295                 300

Ile Val Gln Tyr Asn Gly Asn Tyr Thr Pro Ser Ser Thr Pro Ser Leu
305                 310                 315                 320

Pro Tyr Leu Pro Tyr Phe Asn Asp Thr Thr Ala Ser Val Asn Phe Thr
                325                 330                 335

Gly Arg Leu Arg Ser Leu Ala Asp Asn Asn His Pro Ile Tyr Val Pro
            340                 345                 350

Met Ser Ile Ser Thr Pro Leu Phe Phe Thr Val Ser Val Asn Ile Phe
        355                 360                 365

Thr Cys Ala Asn Thr Ser Cys Gly Ala Asn Gln Ser Arg Leu Ala Ala
    370                 375                 380

Ser Val Asn Asn Ile Ser Phe Gln Thr Pro Thr Arg Met Asp Ile Leu
```

```
              385                 390                 395                 400
Arg Ala Tyr Tyr Asn Gln Ile Asn Gly Val Tyr Gly Asp His Phe Pro
                    405                 410                 415
Asp Lys Pro Pro Leu Phe Phe Asn Phe Thr Ala Asp Thr Ile Pro Leu
                    420                 425                 430
Ile Tyr Lys Thr Pro Ser Lys Gly Thr Glu Val Lys Val Leu Glu Tyr
                    435                 440                 445
Asn Ser Thr Val Glu Ile Val Phe Gln Gly Thr Asn Val Ala Ala Gly
            450                 455                 460
Thr Asp His Pro Met His Ile His Gly Thr Ser Phe Tyr Val Val Gly
465                 470                 475                 480
Trp Gly Phe Gly Asn Phe Asp Lys Asp Lys Asp Pro Leu Arg Tyr Asn
                    485                 490                 495
Leu Val Asp Pro Pro Leu Gln Asn Thr Ile Val Ile Pro Lys Asn Gly
                    500                 505                 510
Trp Ser Val Ile Arg Phe Lys Ala Thr Asn Pro Gly Val Trp Phe Val
                    515                 520                 525
His Cys His Leu Glu Arg His Leu Ser Trp Gly Met Glu Met Ala Phe
            530                 535                 540
Ile Ile Lys Asn Gly Arg Gly Lys Lys Ala Gln Met Leu Pro Pro Pro
545                 550                 555                 560
Pro Tyr Met Pro Pro Cys
                565

<210> SEQ ID NO 55
<211> LENGTH: 566
<212> TYPE: PRT
<213> ORGANISM: Populus trichocarpa

<400> SEQUENCE: 55

Met Ile Pro Ile Met Arg Val Leu Ala Phe Gln Ile Leu Arg Phe Leu
1               5                   10                  15

Leu Phe Gly Gly Phe Leu Cys Cys Gln Ala Ile Val His His Thr Phe
                20                  25                  30

Val Val Lys Asp Val Pro Tyr Thr Arg Leu Cys Ser Thr Lys Asn Ile
            35                  40                  45

Met Thr Val Asn Gly Gln Phe Pro Gly Pro Thr Leu Tyr Val Thr Lys
        50                  55                  60

Gly Glu Thr Ile Ile Val Asp Val Ile Asn Lys Ser Pro His Asn Ile
65                  70                  75                  80

Thr Ile His Trp His Gly Val Asn Gln Pro Lys Tyr Pro Trp Ser Asp
                85                  90                  95

Gly Pro Glu Tyr Ile Thr Gln Cys Pro Ile Gln Pro Gly Gly Lys Phe
                100                 105                 110

Lys Gln Arg Val Ile Phe Ser Asp Glu Glu Gly Thr Leu Trp Trp His
            115                 120                 125

Ala His Ser Asp Trp Thr Arg Ala Thr Val Tyr Gly Ala Ile Val Ile
        130                 135                 140

Tyr Pro Lys Lys Gly Thr Glu Tyr Pro Phe Pro Ala Pro His Ala Asp
145                 150                 155                 160

Val Pro Ile Ile Leu Gly Glu Trp Trp Lys Lys Asp Ile Phe Glu Ile
                165                 170                 175

Phe Asp Gln Phe Arg Ala Ser Gly Ala Asp Pro Asn Val Ser Asp Ser
                180                 185                 190
```

```
Tyr Thr Ile Asn Gly Gln Pro Gly Asp Leu Tyr Pro Cys Ser Lys Ser
            195                 200                 205

Asp Thr Phe Lys Leu Ser Val Asp Tyr Gly Lys Thr Tyr Leu Leu Arg
    210                 215                 220

Leu Ile Asn Ala Ala Leu Gln Asp Ile Val Phe Phe Ser Ile Thr Asn
225                 230                 235                 240

His Gln Val Thr Val Gly Thr Asp Ala Ser Tyr Thr Lys Pro Leu
                245                 250                 255

Lys Val Asp Tyr Ile Ala Ile Ser Pro Gly Gln Thr Ile Asp Val Leu
            260                 265                 270

Leu Glu Ala Asn Gln Pro Leu Asp His Tyr Tyr Met Ala Ala Lys Val
        275                 280                 285

Tyr Ser Ser Ala Asn Gly Val Gln Tyr Asp Asn Thr Thr Thr Ala
    290                 295                 300

Ile Val Gln Tyr Asn Gly Asn Tyr Thr Pro Ser Ser Thr Leu Ser Leu
305                 310                 315                 320

Pro Tyr Leu Pro Tyr Phe Asn Asp Thr Thr Ala Ser Val Asn Phe Thr
                325                 330                 335

Gly Arg Leu Arg Ser Leu Ala Asp Asn Asn His Pro Ile His Val Pro
            340                 345                 350

Met Ser Ile Ser Thr Pro Leu Phe Phe Thr Val Ser Val Asn Ile Phe
        355                 360                 365

Thr Cys Ala Asn Thr Ser Cys Gly Ala Asn Gln Ser Arg Leu Ala Ala
    370                 375                 380

Ser Val Asn Asn Ile Ser Phe Gln Thr Pro Thr Arg Met Asp Ile Leu
385                 390                 395                 400

Arg Ala Tyr Tyr Asn Gln Ile Asn Gly Val Tyr Gly Asp His Phe Pro
                405                 410                 415

Asp Lys Pro Pro Leu Phe Phe Asn Phe Thr Ala Asp Thr Ile Pro Leu
            420                 425                 430

Ile Tyr Glu Thr Pro Ser Lys Gly Thr Glu Val Lys Val Leu Glu Tyr
        435                 440                 445

Asn Ser Thr Val Glu Ile Val Phe Gln Gly Thr Asn Val Ala Ala Gly
    450                 455                 460

Thr Asp His Pro Met His Ile His Gly Thr Ser Phe Tyr Val Val Gly
465                 470                 475                 480

Trp Gly Phe Gly Asn Phe Asp Lys Asp Lys Asp Pro Leu Arg Tyr Asn
                485                 490                 495

Leu Phe Asp Pro Pro Leu Gln Asn Thr Ile Ala Val Pro Lys Asn Gly
            500                 505                 510

Trp Ser Val Ile Arg Phe Lys Ala Thr Asn Pro Gly Val Trp Phe Val
        515                 520                 525

His Cys His Leu Glu Arg His Leu Ser Trp Gly Met Glu Met Ala Phe
    530                 535                 540

Ile Ile Lys Asn Gly Arg Gly Lys Lys Ala His Met Leu Pro Pro Pro
545                 550                 555                 560

Pro Tyr Met Pro Pro Cys
                565

<210> SEQ ID NO 56
<211> LENGTH: 562
<212> TYPE: PRT
<213> ORGANISM: Populus trichocarpa

<400> SEQUENCE: 56
```

-continued

```
Met Arg Val Leu Ala Phe Gln Ile Ser Arg Phe Leu Phe Gly Gly
 1               5                  10                 15

Phe Leu Cys Cys Gln Ala Ile Val His His Thr Phe Val Lys Asp
             20                  25                 30

Val Pro Tyr Thr Arg Leu Cys Ser Thr Lys Asn Ile Met Thr Val Asn
             35                  40                 45

Gly Gln Phe Pro Gly Pro Thr Leu Tyr Val Thr Lys Gly Glu Thr Ile
 50                      55                 60

Ile Val Asp Val Ile Asn Lys Ser Pro His Asn Ile Thr Ile His Trp
 65                  70                  75                 80

His Gly Val Lys Gln Pro Lys Tyr Pro Trp Ser Asp Gly Pro Glu Tyr
                 85                  90                 95

Ile Thr Gln Cys Pro Ile Gln Pro Gly Gly Lys Phe Ser Gln Arg Val
                 100                 105                110

Ile Phe Ser Glu Glu Gly Thr Leu Trp Trp His Ala His Ser Asp
             115                 120                125

Trp Thr Arg Ala Thr Val Tyr Gly Ala Ile Val Ile Tyr Pro Asn Glu
 130                 135                 140

Gly Thr Lys Tyr Pro Phe Leu Ala Pro His Ala Asp Val Pro Ile Ile
 145                 150                 155                160

Leu Gly Glu Trp Trp Lys Lys Asp Ile Phe Asp Ile Phe Asp Gln Phe
                 165                 170                 175

Arg Ala Ser Gly Ala Asp Pro Asn Val Ser Asp Ala Tyr Thr Ile Asn
             180                 185                 190

Gly Gln Pro Gly Asp Leu Tyr Pro Cys Ser Lys Ser Asp Thr Phe Lys
             195                 200                 205

Leu Ser Val Asp Tyr Gly Lys Thr Tyr Leu Leu Arg Leu Ile Asn Ala
 210                 215                 220

Ala Leu Gln Asp Ile Leu Phe Phe Ser Ile Thr Asp His Gln Val Thr
 225                 230                 235                240

Val Val Gly Thr Asp Ala Gly Tyr Thr Lys Pro Leu Lys Val Asp Tyr
             245                 250                 255

Val Ala Ile Ser Pro Gly Gln Thr Ile Asp Val Leu Leu Glu Ala Asn
             260                 265                 270

Gln Pro Leu Asp His Tyr Tyr Met Ala Ala Lys Val Tyr Ser Ser Ala
 275                 280                 285

Asn Gly Val Gln Tyr Asp Asn Thr Thr Thr Ala Ile Val Gln Tyr
 290                 295                 300

Asn Gly Asn Tyr Thr Pro Ser Ser Thr Ser Ser Leu Pro Tyr Leu Phe
 305                 310                 315                320

Tyr Phe Asn Asp Thr Thr Ala Leu Val Asn Phe Thr Gly Arg Leu Arg
                 325                 330                 335

Ser Leu Ala Asp Asn Asn His Pro Ile His Val Pro Leu Ser Ile Ser
             340                 345                 350

Thr Thr Leu Phe Phe Thr Val Ser Val Asn Arg Phe Thr Cys Ala Asn
             355                 360                 365

Thr Ser Cys Gly Ala Thr Gln Ser Arg Leu Ala Ala Ser Val Asn Asn
 370                 375                 380

Ile Ser Phe Gln Thr Pro Thr Arg Met Asp Ile Leu Arg Ala Tyr Tyr
 385                 390                 395                400

Asn Gln Ile Asn Gly Val Tyr Gly Asp His Phe Pro Asp Ile Pro Pro
                 405                 410                 415
```

```
Leu Phe Phe Asn Phe Thr Ala Asp Ser Ile Pro Leu Ile Tyr Glu Thr
                420                 425                 430

Pro Ser Lys Gly Thr Glu Val Lys Val Leu Glu Tyr Asn Ser Thr Val
        435                 440                 445

Glu Ile Val Phe Gln Gly Thr Asn Val Ala Ala Gly Thr Asp His Pro
    450                 455                 460

Met His Ile His Gly Thr Ser Phe Tyr Val Val Gly Trp Gly Phe Gly
465                 470                 475                 480

Asn Phe Asp Lys Asp Lys Asp Pro Leu Arg Tyr Asn Leu Val Asp Pro
                485                 490                 495

Pro Leu Gln Asn Thr Ile Ala Val Pro Lys Asn Gly Trp Ser Val Ile
        500                 505                 510

Arg Phe Lys Ala Thr Asn Pro Gly Val Trp Phe Met His Cys His Leu
    515                 520                 525

Glu Arg His Leu Ser Trp Gly Met Glu Met Thr Phe Ile Ile Lys Asn
    530                 535                 540

Gly Arg Gly Lys Lys Ala Gln Met Leu Pro Pro Pro Tyr Met Pro
545                 550                 555                 560

Pro Cys

<210> SEQ ID NO 57
<211> LENGTH: 565
<212> TYPE: PRT
<213> ORGANISM: Populus trichocarpa

<400> SEQUENCE: 57

Met Leu Phe Cys Lys Lys Thr Leu Val Phe Lys Ile Leu Trp Val Leu
1               5                   10                  15

Leu Phe Phe Ser Val His Cys Leu Ala Ala Thr His Tyr His Phe Lys
            20                  25                  30

Val Met Glu Ala Pro Tyr Thr Arg Leu Cys Ser Lys Lys Lys Ile Leu
        35                  40                  45

Thr Val Asn Gly Gln Phe Pro Gly Pro Ala Leu His Val His His Gly
    50                  55                  60

Asp Thr Ile Tyr Val Thr Val His Asn Lys Gly Arg Tyr Asn Ile Thr
65                  70                  75                  80

Ile His Trp His Gly Val Lys Leu Thr Gly Tyr Pro Trp Ser Asp Gly
                85                  90                  95

Pro Glu Tyr Ile Thr Gln Cys Pro Ile Gln Pro Gly Gly Lys Phe Lys
            100                 105                 110

Gln Lys Ile Ile Phe Ser Thr Glu Glu Gly Thr Leu Trp Trp His Ala
        115                 120                 125

His Ser Asp Trp Ser Arg Ala Thr Val His Gly Pro Ile Ile Val Tyr
    130                 135                 140

Pro Lys Ile Asn Gly Thr Gly Tyr Pro Phe Ser Lys Pro Leu Val Glu
145                 150                 155                 160

Val Pro Ile Ile Leu Gly Glu Trp Trp Lys Arg Asp Val Met Asp Val
                165                 170                 175

Leu Gln Glu Ala Val Ile Thr Gly Gly Asp Pro Ala Val Ser Asp Ala
            180                 185                 190

Phe Thr Ile Asn Gly Gln Pro Gly Asp Leu Tyr Pro Cys Ser Lys Ser
        195                 200                 205

Glu Thr Ile Lys Leu Asn Val His Gln Gly Asn Ser Tyr Leu Leu Arg
    210                 215                 220
```

```
Ile Val Asn Ala Ala Leu Asn Thr Ile Leu Phe Ser Val Ala Lys
225                 230                 235                 240

His Asn Leu Thr Val Val Gly Ile Asp Gly Ser Tyr Ala Lys Gln Leu
            245                 250                 255

Thr Ser Gly Tyr Ile Thr Ile Ala Ser Gly Gln Thr Ile Asp Ala Val
        260                 265                 270

Leu His Ala Asn Gln Asp Pro Asn His Tyr Tyr Met Ala Ala Arg Ala
    275                 280                 285

Phe Thr Ser Ser Pro Ser Val Ala Phe Asp Asn Thr Ala Thr Ala
290                 295                 300

Ile Val Gln Tyr Ser Gly Asp Tyr Thr Leu Ser Ser Phe Pro Ser Leu
305                 310                 315                 320

Pro Gln Leu Pro Tyr Tyr Asp Asp Thr Asn Ala Ala Tyr Ser Phe Leu
                325                 330                 335

Ser Ser Leu Arg Ser Leu Ala Asp Glu Asp His Pro Val Arg Val Pro
            340                 345                 350

Ser Asn Ile Thr Thr Arg Ile Val Ser Thr Leu Ser Val Asn Ala Leu
        355                 360                 365

Pro Cys His Arg Asn Arg Ser Cys Glu Gly Pro Asn Gly Thr Ile Leu
370                 375                 380

Ala Ala Ser Met Asn Asn Ile Thr Phe Val Asn Pro Ser Val Asp Ile
385                 390                 395                 400

Leu Glu Ala Tyr Tyr Lys His Ile His Gly Val Tyr Gly Ala Asp Phe
                405                 410                 415

Pro Ser Phe Pro Pro Leu Val Phe Asn Phe Thr Ala Asp Asn Leu Pro
            420                 425                 430

Leu Ile Leu Glu Val Ser Lys Thr Gly Thr Glu Val Lys Ile Leu Pro
        435                 440                 445

Phe Asn Ser Ala Val Glu Ile Ile Phe Gln Gly Thr Asn Val Val Ala
    450                 455                 460

Gly Asp Asp His Pro Met His Leu His Gly Tyr Ser Phe Tyr Ile Val
465                 470                 475                 480

Gly Trp Gly Tyr Gly Asn Phe Asp Lys Asp Lys Asp Pro Gln Asn Tyr
                485                 490                 495

Asn Leu Ile Asp Pro Pro Phe Arg Asn Thr Val Thr Val Pro Arg Asn
            500                 505                 510

Gly Trp Thr Thr Ile Arg Phe Glu Ala Thr Asn Pro Gly Val Trp Phe
        515                 520                 525

Met His Cys His Phe Asp Arg His Leu Val Trp Gly Met Glu Thr Val
    530                 535                 540

Phe Ile Val Gln Asp Gly Thr Glu Ala Arg Leu Ser Pro Pro Pro
545                 550                 555                 560

Asp Met Pro Pro Cys
                565

<210> SEQ ID NO 58
<211> LENGTH: 540
<212> TYPE: PRT
<213> ORGANISM: Populus trichocarpa

<400> SEQUENCE: 58

Met Glu Gly Val Arg Lys His Tyr Gly Ile Leu Leu Ala Ser Leu Ala
1               5                   10                  15

Ile Ile Ala Ala Ala Leu Pro Cys Cys Ser Ser Gln Thr Thr Arg Gly
            20                  25                  30
```

-continued

```
Phe Gln Phe Asn Val Glu Trp Lys Lys Val Thr Arg Leu Leu Thr Pro
         35                  40                  45
Ser Asn Gly Asp Ser Ile His Ile Lys Val Lys Asn Arg Ile Ala Gln
 50                  55                  60
Asn Thr Thr Leu His Trp His Gly Val Arg Gln Leu Arg Thr Gly Trp
 65                  70                  75                  80
Ala Asp Gly Pro Ala Tyr Val Thr Gln Cys Pro Ile Arg Gly Gly Gln
             85                  90                  95
Ser Tyr Thr Tyr Lys Phe Thr Val Thr Gly Gln Arg Gly Thr Leu Leu
             100                 105                 110
Trp His Ala His Tyr Ala Trp Gln Arg Ala Ser Val Tyr Gly Ala Phe
             115                 120                 125
Ile Ile Tyr Pro Arg Ile Gln Tyr Pro Phe Ser His Arg Ile Gln Ala
 130                 135                 140
Glu Ile Pro Ile Ile Phe Gly Glu Trp Trp Asn Gly Asp Pro Asp Glu
145                 150                 155                 160
Val Glu Lys Thr Met Leu Leu Thr Gly Gly Pro Asp Ser Ser Asn
                 165                 170                 175
Ala Tyr Thr Ile Asn Gly Leu Pro Gly Pro Leu Tyr Pro Cys Ser Asn
             180                 185                 190
Gln Asp Thr Phe Ile Gln Thr Val Glu Tyr Gly Lys Thr Tyr Leu Leu
             195                 200                 205
Arg Ile Ile Asn Ala Ala Leu Thr Asn Glu Leu Phe Phe Ala Ile Ala
 210                 215                 220
Lys His Thr Leu Thr Val Glu Val Val Ala Val Tyr Thr Lys Pro
225                 230                 235                 240
Phe Ala Thr Thr Ser Ile Met Ile Ser Pro Gly Gln Thr Thr Thr Val
             245                 250                 255
Leu Met Thr Ala Asn Lys Val Pro Asp Phe Thr Gly Met Phe Val Met
             260                 265                 270
Ala Ala Arg Pro Tyr Leu Thr Ser Val Phe Pro Ser Asn Asn Ser Thr
         275                 280                 285
Thr Ile Gly Phe Leu Arg Tyr Lys Asn Ala Arg Thr Trp Lys Gly Lys
         290                 295                 300
Ser Pro Val Asp Pro Ser Ser Leu Lys Leu His Asn Leu Pro Ala Met
305                 310                 315                 320
Glu Asp Thr Ala Phe Ala Thr Lys Phe Ser Asp Lys Ile Arg Ser Leu
             325                 330                 335
Ala Ser Ser Gln Tyr Pro Cys Asn Val Pro Lys Thr Ile Asp Lys Arg
             340                 345                 350
Val Ile Thr Thr Ile Ser Leu Asn Leu Gln Asp Cys Pro Glu Asn Lys
             355                 360                 365
Thr Cys Ser Gly Phe Lys Gly Lys Ser Phe Phe Ala Ser Met Asn Asn
 370                 375                 380
Gln Ser Phe Val Arg Pro Ser Ile Ser Ile Leu Glu Ser Tyr Tyr Lys
385                 390                 395                 400
Asn Leu Thr Lys Gly Ser Phe Ser Ser Gly Phe Pro Glu Lys Pro Pro
             405                 410                 415
Asn Asn Phe Asp Tyr Thr Val Leu Pro Tyr Gly Thr Asn Ile Glu Ile
             420                 425                 430
Val Leu Gln Asp Thr Ser Phe Leu Asn Leu Glu Asn His Pro Ile His
             435                 440                 445
```

```
Val His Gly His Asn Phe Phe Ile Val Gly Ser Gly Phe Gly Asn Phe
    450                 455                 460

Asn Glu Ala Arg Asp Pro Lys Arg Tyr Asn Leu Val Asp Pro Pro Glu
465                 470                 475                 480

Arg Asn Thr Val Ala Val Pro Ser Gly Gly Trp Ala Ala Ile Arg Ile
                485                 490                 495

Lys Ala Asp Asn Pro Gly Val Trp Phe Ile His Cys His Leu Glu Glu
                500                 505                 510

His Thr Ser Trp Gly Leu Ala Thr Gly Phe Ile Val His Asn Gly Gln
            515                 520                 525

Gly Pro Ser Gln Ser Leu Leu Pro Pro Pro Ser
530                 535                 540

<210> SEQ ID NO 59
<211> LENGTH: 480
<212> TYPE: PRT
<213> ORGANISM: Populus trichocarpa

<400> SEQUENCE: 59

Met Ser Lys Asn Phe Gln Cys Leu Lys Ile Arg Gly Gly His Ser Tyr
1               5                   10                  15

Thr Tyr Lys Phe Thr Val Thr Gly Gln Arg Gly Thr Leu Leu Trp His
                20                  25                  30

Ala His Tyr Ala Trp Gln Arg Ala Ser Val Tyr Gly Ala Phe Ile Ile
            35                  40                  45

Tyr Pro Arg Ile Pro Tyr Pro Phe Ser His Pro Ile Gln Ala Glu Ile
        50                  55                  60

Pro Ile Ile Phe Gly Glu Trp Trp Asn Gly Asp Pro Asp Glu Val Glu
65                  70                  75                  80

Lys Thr Met Leu Leu Thr Gly Gly Pro Asp Ser Ser Asn Ala Tyr
                85                  90                  95

Thr Ile Asn Gly Leu Pro Gly Pro Leu Tyr Pro Cys Ser Asn Gln Asp
                100                 105                 110

Thr Phe Ile Gln Thr Val Glu Tyr Gly Lys Thr Tyr Leu Leu Arg Ile
            115                 120                 125

Ile Asn Ala Ala Leu Thr Asn Glu Leu Phe Phe Ala Ile Ala Lys His
130                 135                 140

Thr Leu Thr Val Val Glu Val Ala Val Tyr Thr Lys Pro Phe Ala
145                 150                 155                 160

Thr Thr Ser Ile Met Ile Ser Pro Gly Gln Thr Thr Val Leu Met
                165                 170                 175

Thr Ala Asn Lys Val Pro Asp Phe Thr Gly Met Phe Val Met Ala Ala
                180                 185                 190

Arg Pro Tyr Leu Thr Ser Val Phe Pro Ser Asn Ser Thr Thr Ile
            195                 200                 205

Gly Phe Leu Arg Tyr Lys Asn Ala Arg Thr Trp Lys Gly Lys Ser Pro
        210                 215                 220

Val Asp Pro Ser Ser Leu Lys Leu His Asn Leu Pro Ala Met Glu Asp
225                 230                 235                 240

Thr Ala Phe Ala Thr Lys Phe Ser Asp Lys Ile Lys Ser Leu Ala Ser
                245                 250                 255

Pro Gln Tyr Pro Cys Asn Val Pro Lys Thr Ile Asp Lys Arg Val Ile
            260                 265                 270

Thr Thr Ile Ser Leu Asn Leu Gln Asp Cys Pro Glu Asn Lys Thr Cys
        275                 280                 285
```

```
Ser Gly Phe Lys Gly Lys Ser Phe Ala Ser Met Asn Asn Gln Ser
    290                 295                 300

Phe Val Arg Pro Ser Ile Ser Ile Leu Glu Ser Tyr Tyr Lys Asn Leu
305                 310                 315                 320

Thr Lys Gly Ser Phe Ser Gly Phe Pro Glu Lys Pro Pro Asn Asn
                325                 330                 335

Phe Asp Tyr Thr Gly Gly Asp Ser Phe Thr Gln Asn Met Asn Thr Lys
                340                 345                 350

Phe Gly Thr Lys Leu Leu Val Leu Pro Tyr Gly Thr Asn Ile Glu Ile
                355                 360                 365

Val Leu Gln Asp Thr Ser Phe Leu Asn Ser Glu Asn His Pro Ile His
    370                 375                 380

Val His Gly His Asn Phe Phe Ile Val Gly Ser Gly Leu Gly Asn Phe
385                 390                 395                 400

Asn Glu Ala Arg Asp Arg Lys Arg Tyr Asn Leu Val Asp Pro Pro Glu
                405                 410                 415

Arg Asn Thr Val Ala Val Pro Ser Gly Gly Trp Ala Ala Ile Arg Ile
                420                 425                 430

Lys Ala Asp Asn Pro Gly Val Trp Phe Ile His Cys His Leu Glu Gln
                435                 440                 445

His Thr Ser Trp Gly Leu Ala Thr Gly Phe Ile Val His Asn Gly Glu
    450                 455                 460

Gly Pro Ser Gln Cys Leu Leu Pro Pro Gln Asp Leu Pro Ser Cys
465                 470                 475                 480

<210> SEQ ID NO 60
<211> LENGTH: 556
<212> TYPE: PRT
<213> ORGANISM: Manihot esculenta

<400> SEQUENCE: 60

Met Ala Cys Ser Leu Leu Pro Thr Thr Thr Leu Leu Leu Leu Ile Phe
1               5                   10                  15

Leu Phe Pro Thr Phe Val Glu Ser Ala Ile Arg His Tyr Asn Phe Thr
                20                  25                  30

Val Val Met Lys Asn Thr Thr Lys Leu Cys Ser Ser Lys Ser Ile Ala
            35                  40                  45

Thr Ile Asn Gly Lys Phe Pro Gly Pro Thr Leu Tyr Ala Arg Glu Asp
    50                  55                  60

Asp Thr Val Asn Val Arg Val Ser Asn Asn Ile Gln Tyr Asn Val Thr
65                  70                  75                  80

Ile His Trp His Gly Val Arg Gln Leu Arg Thr Gly Trp Ser Asp Gly
                85                  90                  95

Pro Ala Tyr Ile Thr Gln Cys Pro Ile Gln Pro Gly Gln Ser Phe Leu
                100                 105                 110

Tyr Asn Phe Thr Leu Thr Gly Gln Arg Gly Thr Leu Leu Trp His Ala
                115                 120                 125

His Ile Ser Trp Leu Arg Thr Thr Ile His Gly Ala Ile Val Ile Phe
    130                 135                 140

Pro Lys Lys Gly Val Pro Tyr Pro Phe Pro Lys Pro Asp Lys Glu Lys
145                 150                 155                 160

Leu Ile Ile Leu Ser Glu Trp Trp Lys Ala Asp Thr Glu Ala Val Ile
                165                 170                 175

Asn Gln Ala Met Gln Thr Gly Leu Pro Pro Asn Ile Ser Asp Ser His
```

```
              180                 185                 190
Thr Ile Asn Gly His Val Gly Pro Ala Thr Gly Cys Thr Ser Gln Gly
            195                 200                 205
Tyr Thr Leu His Val Glu Pro Gly Lys Thr Tyr Leu Ile Arg Leu Val
            210                 215                 220
Asn Ala Ala Ile Asn Asp Glu Leu Phe Phe Lys Ile Ala Gly His Asn
225                 230                 235                 240
Leu Lys Ile Val Glu Val Asp Ala Ser Tyr Thr Lys Pro Phe Thr Thr
                245                 250                 255
Asp Thr Ile Phe Ile Gly Pro Gly Gln Thr Thr Asn Ala Leu Leu Thr
            260                 265                 270
Thr Asp Gln Ala Thr Gly Lys Tyr Leu Ile Ala Val Ser Pro Phe Met
        275                 280                 285
Asp Thr Ile Val Ala Val Asp Asn Val Thr Ala Ile Ala Phe Leu Arg
        290                 295                 300
Tyr Lys Asp Thr Leu Ala Phe Ser Pro Pro Val Leu Thr Ser Thr Pro
305                 310                 315                 320
Ala Ile Asn Ala Thr Ala Val Thr Ser Lys Phe Met Asp Asn Leu Arg
                325                 330                 335
Ser Leu Asn Ser Lys Lys Tyr Pro Ala Asn Val Pro Leu Thr Val Asp
            340                 345                 350
His Tyr Leu Tyr Phe Thr Ile Gly Val Gly Ile Asn Ser Cys Pro Thr
        355                 360                 365
Cys Val Asn Gly Ser Lys Ser Val Gly Asn Ile Asn Asn Val Ser Phe
    370                 375                 380
Val Met Pro Ser Thr Ala Leu Leu Gln Ala His Tyr Tyr Asn Ile Ser
385                 390                 395                 400
Gly Ile Phe Thr Asp Asp Phe Pro Ala Asn Pro Leu Val Pro Phe Asn
                405                 410                 415
Tyr Thr Gly Asn Phe Thr Gly Gly Ile Ser Thr Met Asn Gly Thr Arg
            420                 425                 430
Leu Phe Arg Ile Ala Phe Asn Ser Thr Val Gln Ile Val Leu Gln Gly
        435                 440                 445
Thr Gly Ile Ile Ala Pro Glu Ser His Pro Ile His Leu His Gly Phe
    450                 455                 460
Asn Phe Phe Ala Ile Ala Lys Gly Val Gly Asn Phe Asp Leu Val Asn
465                 470                 475                 480
Asp Pro Lys Lys Phe Asn Leu Val Asp Pro Val Glu Arg Asn Thr Ile
                485                 490                 495
Ser Val Pro Thr Gly Gly Trp Thr Ala Ile Arg Phe Arg Ala Asp Asn
            500                 505                 510
Pro Gly Val Trp Phe Leu His Cys His Leu Glu Val His Thr Ser Trp
        515                 520                 525
Gly Leu Lys Met Ala Phe Val Val Asp Asn Gly Lys Gly Pro Asn Glu
    530                 535                 540
Ser Leu Pro Pro Pro Ser Asp Leu Pro Gln Cys
545                 550                 555

<210> SEQ ID NO 61
<211> LENGTH: 553
<212> TYPE: PRT
<213> ORGANISM: Gossypium raimondii

<400> SEQUENCE: 61
```

```
Met Val Cys Trp Val Arg Thr Leu Leu Phe Ile Ser Val Leu Val Pro
1               5                   10                  15
Ala Phe Val Glu Cys Arg Ile Arg His Tyr His Phe Asn Val Val Val
            20                  25                  30
Lys Asn Ala Thr Lys Leu Cys Ser Thr Lys Pro Ile Val Thr Val Asn
        35                  40                  45
Gly Thr Phe Pro Gly Pro Arg Leu Tyr Ala Arg Glu Gly Asp Asn Val
    50                  55                  60
Leu Val Arg Leu Thr Asn His Val Gln Tyr Asn Val Thr Ile His Trp
65                  70                  75                  80
His Gly Val Arg Gln Leu Arg Thr Gly Trp Ser Asp Gly Pro Ala Tyr
                85                  90                  95
Ile Thr Gln Cys Pro Ile Gln Pro Gly Gln Asn Phe Leu Tyr Asn Phe
            100                 105                 110
Thr Leu Thr Gly Gln Arg Gly Thr Leu Leu Trp His Ala His Ile Ser
        115                 120                 125
Trp Leu Arg Thr Thr Val His Gly Ala Ile Val Ile Leu Pro Lys Lys
    130                 135                 140
Gly Val Pro Tyr Pro Phe Pro Lys Pro Tyr Lys Glu Lys Val Ile Val
145                 150                 155                 160
Leu Gly Glu Trp Trp Lys Ala Asp Thr Glu Ala Val Val Lys Gln Ala
                165                 170                 175
Thr Gln Thr Gly Leu Pro Pro Asn Ile Ser Asp Ala His Thr Ile Asn
            180                 185                 190
Gly His Pro Gly Pro Val Pro Asn Cys Ser Ser Asp Asp Ala Tyr Thr
        195                 200                 205
Leu His Val Glu Thr Gly Lys Thr Tyr Leu Leu Arg Val Ile Asn Ala
    210                 215                 220
Ala Val Asn Asp Glu Leu Phe Phe Lys Ile Ala Asn His Asn Leu Thr
225                 230                 235                 240
Val Val Glu Val Asp Ala Cys Tyr Thr Lys Pro Phe Glu Thr Asp Thr
                245                 250                 255
Leu Phe Leu Gly Pro Gly Gln Thr Thr Thr Ala Leu Leu Lys Ala Asp
            260                 265                 270
Gln Gly Ile Gly Lys Ser Leu Ile Ala Ile Ser Pro Phe Met Asp Thr
        275                 280                 285
Thr Val Ala Val Asn Asn Leu Thr Gly Ile Gly Tyr Leu Arg Tyr Asn
    290                 295                 300
His Thr Leu Ala Phe Thr Pro Thr Thr Phe Val Ala Ile Pro Ala Val
305                 310                 315                 320
Asn Ala Thr Pro Val Thr Ser Val Phe Ser Asp Ser Leu Arg Ser Leu
                325                 330                 335
Asn Ser Lys Gln Tyr Pro Ala Asn Val Pro Leu Thr Ile Asp His Ser
            340                 345                 350
Leu Phe Phe Thr Ile Gly Gly Ile Asn Pro Cys Ala Thr Cys Phe Asn
        355                 360                 365
Gly Ser Arg Ala Val Ala Ala Ile Asn Asn Val Ser Phe Val Met Pro
    370                 375                 380
Thr Thr Ala Ile Leu Gln Ala His Tyr Tyr Gly Ile Asn Gly Val Phe
385                 390                 395                 400
Thr Asp Asp Phe Pro Ala Lys Pro Ala Ile Pro Phe Asn Tyr Thr Gly
                405                 410                 415
Thr Pro Pro Ser Gly Val Gln Thr Met Asn Gly Thr Lys Val Tyr Arg
```

```
            420             425             430
Leu Ala Tyr Asn Ser Thr Val Gln Leu Val Ile Gln Gly Asn Thr Ile
                435             440             445
Ile Ala Pro Glu Ser His Pro Thr His Leu His Gly Ser Asn Phe Phe
    450             455             460
Val Val Gly Arg Gly Val Gly Asn Phe Asp Pro Glu Lys Asp Pro Leu
465             470             475             480
Lys Phe Asn Leu Val Asp Pro Val Glu Arg Asn Thr Val Ser Val Pro
                485             490             495
Thr Ala Gly Trp Thr Ala Ile Arg Phe Arg Ala Asp Asn Pro Gly Val
            500             505             510
Trp Phe Phe His Cys His Leu Glu Val His Thr Thr Trp Gly Leu Lys
        515             520             525
Met Ala Phe Leu Val Glu Asn Gly Arg Gly Pro Asn Glu Ser Ile Glu
    530             535             540
Pro Pro Pro Ser Asp Leu Pro Lys Cys
545             550

<210> SEQ ID NO 62
<211> LENGTH: 561
<212> TYPE: PRT
<213> ORGANISM: Eucalyptus grandis

<400> SEQUENCE: 62

Met Arg Arg Ser Glu Gly Ala Glu Met Glu Arg Trp Phe Pro Ala Met
1               5              10              15
Leu Val Val Ala Val Met Leu Pro Ala Ala Glu Gly Leu Ile Arg
                20              25              30
His Tyr Lys Phe Ser Val Val Met Lys Asn Val Thr Lys Leu Cys Ala
            35              40              45
Ser Lys Pro Ile Ala Thr Val Asn Gly Lys Phe Pro Gly Pro Thr Leu
    50              55              60
Tyr Ala Arg Glu Asp Asp Thr Val Leu Val Arg Val Val Asn His Val
65              70              75              80
Ser Tyr Asn Val Thr Ile His Trp His Gly Val Arg Gln Leu Arg Thr
                85              90              95
Gly Trp Ser Asp Gly Pro Ala Phe Ile Thr Gln Cys Pro Ile Gln Pro
            100             105             110
Gly Gln Ser Tyr Ile Tyr Asn Phe Thr Leu Thr Gly Gln Arg Gly Thr
        115             120             125
Leu Leu Trp His Ala His Ile Thr Trp Leu Arg Ser Thr Leu His Gly
    130             135             140
Ala Ile Val Ile Leu Pro Lys Arg Gly Val Pro Tyr Pro Phe Pro Lys
145             150             155             160
Pro Tyr Lys Glu Lys Thr Ile Ile Phe Gly Glu Trp Trp Lys Ala Asp
                165             170             175
Thr Glu Leu Val Leu Ser Gln Ser Val Gln Ser Gly Met Pro Pro Asn
                180             185             190
Lys Ser Asp Ser His Thr Ile Asn Gly Tyr Pro Gly Pro Leu Pro Asn
            195             200             205
Cys Ser Ser Gln Gly Tyr Glu Leu Gln Val Glu Ser Gly Lys Thr Tyr
    210             215             220
Leu Leu Arg Ile Val Asn Ala Ala Val Asn Asp Glu Leu Phe Phe Lys
225             230             235             240
```

```
Ile Ala Gly His Asn Leu Thr Val Val Glu Val Asp Ala Ser Tyr Thr
            245                 250                 255

Lys Pro Phe Ser Ile Asp Thr Ile Phe Ile Ala Pro Gly Gln Thr Thr
        260                 265                 270

Asn Ala Leu Leu Ala Ala Asp Lys Ser Gly Ser Tyr Ile Met Ala
        275                 280                 285

Ile Ser Pro Phe Met Asp Thr Val Ala Val Asp Asn Leu Thr Ala
    290                 295                 300

Thr Gly Ile Val Gln Tyr Lys Gly Thr Ile Ala Ser Ala Pro Thr Val
305                 310                 315                 320

Gln Ala Ser Ile Pro Ala Ile Asn Ala Thr Ser Phe Glu Phe Ser Phe
                325                 330                 335

Ile Asn Ser Leu Arg Ser Leu Asn Ser Lys Gln Tyr Pro Ala Lys Val
                340                 345                 350

Pro Leu Thr Val Asp His Ser Leu Phe Ile Thr Met Ser Ala Gly Val
                355                 360                 365

Asn Pro Cys Ser Thr Cys Val Asn Gly Lys Lys Leu Val Ala Ala Leu
                370                 375                 380

Asn Asn Val Ser Phe Val Met Pro Ser Thr Asp Ile Leu Glu Ala His
385                 390                 395                 400

Tyr Tyr Lys Ile Lys Gly Val Tyr Thr Asp Asp Phe Pro Gly Asn Pro
                405                 410                 415

Pro Thr Pro Phe Asn Tyr Thr Gly Thr Pro Pro Ser Asn Met Gln Thr
                420                 425                 430

Thr Asn Gly Thr Arg Val Tyr Lys Leu Ala Tyr Asn Ser Thr Val Gln
            435                 440                 445

Val Val Leu Gln Gly Thr Ser Ile Ile Ala Pro Glu Asn His Pro Thr
        450                 455                 460

His Leu His Gly Phe Asn Phe Phe Gly Ile Gly Lys Gly Leu Gly Asn
465                 470                 475                 480

Phe Asp Pro Asn Lys Asp Pro Lys Asn Phe Asn Leu Val Asp Pro Val
                485                 490                 495

Glu Arg Asn Thr Ile Gly Val Pro Thr Ala Gly Trp Thr Ala Ile Arg
                500                 505                 510

Phe Arg Ala Asp Asn Pro Gly Val Trp Phe Leu His Cys His Leu Glu
            515                 520                 525

Val His Thr Thr Trp Gly Leu Lys Met Val Phe Ile Val Glu Asp Gly
        530                 535                 540

Asp Gly Pro Asn Glu Ser Leu Leu Pro Pro Ala Asp Leu Pro Lys
545                 550                 555                 560

Cys

<210> SEQ ID NO 63
<211> LENGTH: 529
<212> TYPE: PRT
<213> ORGANISM: Medicago truncatula

<400> SEQUENCE: 63

Met Thr His Asn Val Val Leu Lys Asn Glu Thr Lys Leu Cys Ser Thr
1               5                   10                  15

Lys Ser Phe Val Ser Val Asn Gly Lys Phe Pro Gly Pro Thr Leu Tyr
            20                  25                  30

Ala Arg Glu Asp Asp Thr Leu Ile Val Arg Val Thr Asn Leu Val Gln
        35                  40                  45
```

His Asn Val Thr Ile His Trp His Gly Ile Lys Gln Leu Arg Thr Cys
 50                      55                      60

Trp Ser Asp Gly Pro Ala Tyr Val Thr Gln Cys Pro Ile Gln Thr Gly
 65                   70                   75                   80

Gln Ser Phe Val Tyr Asn Phe Thr Ile Thr Gly Gln Arg Gly Thr Leu
                      85                   90                   95

Leu Trp His Ala His Ile Thr Trp Leu Arg Ala Thr Met His Gly Ala
             100                 105                 110

Ile Val Ile Leu Pro Lys Arg Gly Thr Pro Tyr Pro Phe Pro Lys Pro
         115                 120                 125

Asp Lys Glu Lys Ile Ile Leu Gly Glu Trp Trp Lys Ser Asp Val
130                 135                 140

Glu Ala Val Val Asn Gln Ala Thr Ser Ser Gly Met Pro Pro Asn Ile
145                 150                 155                 160

Ser Asp Ala His Thr Ile Asn Gly His Pro Gly Pro Val Pro Gly Cys
                 165                 170                 175

Ile Ser Gln Gly Tyr Thr Leu His Val Glu Ser Gly Lys Thr Tyr Leu
             180                 185                 190

Leu Arg Ile Ile Asn Ala Ala Leu Asn Asp Glu Leu Phe Phe Lys Ile
         195                 200                 205

Ala Gly His Lys Leu Ile Val Val Glu Ala Asp Ala Ser Tyr Leu Lys
210                 215                 220

Pro Phe Glu Ile Asp Thr Ile Phe Leu Ser Pro Gly Gln Thr Thr Asn
225                 230                 235                 240

Val Leu Leu Thr Ala Asn Gln Pro Ile Gly Lys Tyr Leu Ile Ala Ile
                 245                 250                 255

Thr Pro Phe Met Asp Ala Pro Ile Gly Phe Asp Asn Leu Ser Ser Ile
             260                 265                 270

Ala Thr Leu Arg Tyr Lys Gly Ile Pro Pro Tyr Thr Lys Thr Ile Leu
         275                 280                 285

Thr Asn Ile Pro Pro Leu Asn Ala Thr Pro Ile Thr Lys Thr Phe Thr
290                 295                 300

Asp Ser Leu Arg Ser Leu Asn Ser Lys Thr Tyr Pro Thr Arg Val Ser
305                 310                 315                 320

Leu Thr Ile Asp His Ser Leu Leu Phe Ala Ile Thr Val Gly Leu Asn
                 325                 330                 335

Pro Cys Asp Thr Cys Ile Thr Asp Asn Lys Leu Val Ser Ala Ile Asn
             340                 345                 350

Asn Ile Thr Phe Leu Met Pro Thr Val Ser Leu Leu Gln Ala Asn Tyr
         355                 360                 365

Tyr Asn Ile Lys Gly Val Phe Thr Asp Phe Pro Ser Lys Pro Pro
370                 375                 380

Met Val Phe Asp Tyr Thr Gly Thr Asp Gln Pro Ala Asn Leu His Thr
385                 390                 395                 400

Asp Asn Gly Thr Lys Val Tyr Arg Leu Asn Phe Asn Ser Ser Val Gln
                 405                 410                 415

Ile Val Leu Gln Gly Thr Ala Met Ile Ala Pro Glu Asn His Pro Phe
             420                 425                 430

His Leu His Gly Phe Asn Phe Val Val Gly Gln Gly Leu Gly Asn
         435                 440                 445

Phe Asp Pro Glu Lys Asp Pro Leu Arg Phe Asn Leu Val Asp Pro Ile
450                 455                 460

Glu Arg Asn Thr Leu Ser Val Pro Asn Asn Gly Trp Ile Ala Ile Arg

```
                465                 470                 475                 480

Phe Arg Ala Asp Asn Pro Gly Val Trp Phe Leu His Cys His Leu Glu
                485                 490                 495

Val His Thr Thr Trp Gly Leu Lys Met Ala Phe Ile Val Asp Asn Gly
                500                 505                 510

Arg Gly Pro Ser Glu Ser Ile Leu Pro Pro Lys Asp Leu Pro Ile
                515                 520                 525

Cys

<210> SEQ ID NO 64
<211> LENGTH: 556
<212> TYPE: PRT
<213> ORGANISM: Trametes versicolor

<400> SEQUENCE: 64

Met Glu Ser Trp Leu Arg Ile Leu Phe Leu Phe Ala Cys Leu Phe Pro
1               5                   10                  15

Ala Phe Val Glu Cys Arg Ile Arg Arg Tyr Asn Phe Asn Val Met Met
                20                  25                  30

Lys Thr Thr Thr Arg Leu Cys Ser Ser Lys Pro Ile Ala Thr Val Asn
                35                  40                  45

Gly Lys Phe Pro Gly Pro Thr Ile Tyr Ala Arg Glu Gly Asp Asn Val
50                  55                  60

Leu Val Asn Val Val Asn His Val Lys Tyr Asn Val Ser Ile His Trp
65                  70                  75                  80

His Gly Val Arg Gln Leu Arg Thr Gly Trp Ser Asp Gly Pro Ala Tyr
                85                  90                  95

Ile Thr Gln Cys Pro Ile Gln Pro Gly Gln Asn Tyr Val Tyr Asn Phe
                100                 105                 110

Thr Ile Thr Gly Gln Arg Gly Thr Leu Phe Trp His Ala His Ile Leu
                115                 120                 125

Trp Leu Arg Ala Thr Met His Gly Ala Ile Val Ile Leu Pro Lys Leu
                130                 135                 140

Gly Val Pro Tyr Pro Phe Pro Lys Pro Asp His Glu Ala Val Val Val
145                 150                 155                 160

Leu Ala Glu Trp Trp Lys Ser Asp Thr Glu Ala Val Ile Asn Gln Ala
                165                 170                 175

Ile Lys Ser Gly Leu Ala Pro Asn Val Ser Asp Ala His Thr Ile Asn
                180                 185                 190

Gly His Pro Gly Ala Ile Ser Asn Cys Pro Ser Gln Gly Gly Tyr Thr
                195                 200                 205

Leu Ser Val Asp Pro Gly Lys Ser Tyr Met Leu Arg Val Ile Asn Ala
                210                 215                 220

Ala Leu Asn Glu Glu Leu Phe Phe Lys Ile Ala Gly His Lys Met Thr
225                 230                 235                 240

Val Val Glu Val Asp Ala Thr Tyr Val Lys Pro Phe Lys Thr Asp Thr
                245                 250                 255

Ile Ile Ile Ala Pro Gly Gln Thr Thr Asn Val Ile Val Thr Ala Asn
                260                 265                 270

Lys Gly Ser Gly Lys Tyr Met Val Ala Ala Ser Pro Phe Met Asp Ala
                275                 280                 285

Pro Ile Ala Val Asp Asn Val Thr Ala Thr Ala Thr Leu His Tyr Ser
                290                 295                 300

Gly Thr Leu Ala Ser Ser Ile Thr Thr Leu Thr Asn Thr Pro Pro Lys
```

```
                   305                 310                 315                 320
        Asn Ala Thr Pro Val Ala Asn Asn Phe Ile Asp Ser Leu Arg Ser Leu
                            325                 330                 335

Asn Ser Lys Lys Tyr Pro Ala Lys Val Pro Lys Lys Val Asp His Ser
                            340                 345                 350

Leu Phe Phe Thr Val Gly Leu Gly Val Asn Pro Cys Ser Ser Cys Lys
                            355                 360                 365

Gln Gly Asn Gly Ser Arg Val Val Ala Ser Ile Asn Asn Val Thr Phe
                            370                 375                 380

Val Met Pro Thr Val Ala Ile Leu Gln Ala His Phe Phe Gly Ile Lys
        385                 390                 395                 400

Gly Val Tyr Thr Thr Asp Phe Pro Gln Asn Pro Pro Phe Lys Phe Asn
                            405                 410                 415

Tyr Thr Gly Thr Pro Pro Thr Asn Leu Ala Thr Met Ser Gly Thr Lys
                            420                 425                 430

Val Tyr Leu Leu Pro Tyr Asn Ala Thr Val Gln Leu Val Leu Gln Asp
                            435                 440                 445

Thr Gly Ile Ile Ser Pro Glu Asn His Pro Ile His Leu His Gly Phe
                            450                 455                 460

Asn Phe Phe Ala Val Gly Lys Gly Ile Gly Asn Phe Asn Pro Lys Thr
        465                 470                 475                 480

Asp Pro Asn Asn Phe Asn Leu Ile Asp Pro Val Glu Arg Asn Thr Ile
                            485                 490                 495

Gly Val Pro Ser Gly Gly Trp Val Ala Ile Arg Phe Arg Ala Asp Asn
                            500                 505                 510

Pro Gly Val Trp Phe Met His Cys His Leu Glu Ile His Thr Thr Trp
                            515                 520                 525

Gly Leu Lys Met Ala Phe Leu Val Asp Asn Gly Lys Gly Pro Asn Glu
                            530                 535                 540

Ser Leu Leu Pro Pro Lys Asp Leu Pro Lys Cys
        545                 550                 555

<210> SEQ ID NO 65
<211> LENGTH: 558
<212> TYPE: PRT
<213> ORGANISM: Arabidopsis thaliana

<400> SEQUENCE: 65

Met Gly Ser His Met Val Trp Phe Leu Phe Leu Val Ser Phe Phe Ser
1               5                   10                  15

Val Phe Pro Ala Pro Ser Glu Ser Met Val Arg His Tyr Lys Phe Asn
            20                  25                  30

Val Val Met Lys Asn Val Thr Arg Leu Cys Ser Ser Lys Pro Thr Val
        35                  40                  45

Thr Val Asn Gly Arg Tyr Pro Gly Pro Thr Ile Tyr Ala Arg Glu Asp
50                  55                  60

Asp Thr Leu Leu Ile Lys Val Val Asn His Val Lys Tyr Asn Val Ser
65                  70                  75                  80

Ile His Trp His Gly Val Arg Gln Val Arg Thr Gly Trp Ala Asp Gly
                85                  90                  95

Pro Ala Tyr Ile Thr Gln Cys Pro Ile Gln Pro Gly Gln Val Tyr Thr
            100                 105                 110

Tyr Asn Tyr Thr Leu Thr Gly Gln Arg Gly Thr Leu Trp Trp His Ala
        115                 120                 125
```

```
His Ile Leu Trp Leu Arg Ala Thr Val Tyr Gly Ala Leu Val Ile Leu
    130                 135                 140

Pro Lys Arg Gly Val Pro Tyr Pro Phe Pro Lys Pro Asp Asn Glu Lys
145                 150                 155                 160

Val Ile Val Leu Gly Glu Trp Trp Lys Ser Asp Thr Glu Asn Ile Ile
                165                 170                 175

Asn Glu Ala Leu Lys Ser Gly Leu Ala Pro Asn Val Ser Asp Ser His
                180                 185                 190

Met Ile Asn Gly His Pro Gly Pro Val Arg Asn Cys Pro Ser Gln Gly
            195                 200                 205

Tyr Lys Leu Ser Val Glu Asn Gly Lys Thr Tyr Leu Leu Arg Leu Val
    210                 215                 220

Asn Ala Ala Leu Asn Glu Glu Leu Phe Phe Lys Val Ala Gly His Ile
225                 230                 235                 240

Phe Thr Val Val Glu Val Asp Ala Val Tyr Val Lys Pro Phe Lys Thr
                245                 250                 255

Asp Thr Val Leu Ile Ala Pro Gly Gln Thr Thr Asn Val Leu Leu Thr
                260                 265                 270

Ala Ser Lys Ser Ala Gly Lys Tyr Leu Val Thr Ala Ser Pro Phe Met
    275                 280                 285

Asp Ala Pro Ile Ala Val Asp Asn Val Thr Ala Thr Val His
290                 295                 300

Tyr Ser Gly Thr Leu Ser Ser Pro Thr Ile Leu Thr Leu Pro Pro
305                 310                 315                 320

Pro Gln Asn Ala Thr Ser Ile Ala Asn Asn Phe Thr Asn Ser Leu Arg
                325                 330                 335

Ser Leu Asn Ser Lys Lys Tyr Pro Ala Leu Val Pro Thr Thr Ile Asp
                340                 345                 350

His His Leu Phe Phe Thr Val Gly Leu Gly Leu Asn Ala Cys Pro Thr
            355                 360                 365

Cys Lys Ala Gly Asn Gly Ser Arg Val Val Ala Ser Ile Asn Asn Val
    370                 375                 380

Thr Phe Ile Met Pro Lys Thr Ala Leu Leu Pro Ala His Tyr Phe Asn
385                 390                 395                 400

Thr Ser Gly Val Phe Thr Thr Asp Phe Pro Lys Asn Pro Pro His Val
                405                 410                 415

Phe Asn Tyr Ser Gly Gly Ser Val Thr Asn Met Ala Thr Glu Thr Gly
            420                 425                 430

Thr Arg Leu Tyr Lys Leu Pro Tyr Asn Ala Thr Val Gln Leu Val Leu
    435                 440                 445

Gln Asp Thr Gly Val Ile Ala Pro Glu Asn His Pro Val His Leu His
450                 455                 460

Gly Phe Asn Phe Phe Glu Val Gly Arg Gly Leu Gly Asn Phe Asn Ser
465                 470                 475                 480

Thr Lys Asp Pro Lys Asn Phe Asn Leu Val Asp Pro Val Glu Arg Asn
                485                 490                 495

Thr Ile Gly Val Pro Ser Gly Gly Trp Val Val Ile Arg Phe Arg Ala
                500                 505                 510

Asp Asn Pro Gly Val Trp Phe Met His Cys His Leu Glu Val His Thr
            515                 520                 525

Thr Trp Gly Leu Lys Met Ala Phe Leu Val Glu Asn Gly Lys Gly Pro
    530                 535                 540

Asn Gln Ser Ile Leu Pro Pro Lys Asp Leu Pro Lys Cys
```

<210> SEQ ID NO 66
<211> LENGTH: 586
<212> TYPE: PRT
<213> ORGANISM: Oryza sativa

<400> SEQUENCE: 66

```
Met His Cys Thr Ala Leu Ser Pro Ala Leu Ser Ser Pro Ser Pro Ala
1               5                   10                  15

Ala Gly His Ala Ala Asn Met Ala Val Leu Pro Glu Ser Arg Arg Leu
            20                  25                  30

Ser Leu Leu Leu Met Ala Ala Cys Phe Leu Leu Gln Ala Leu Ser Ala
        35                  40                  45

His Ala Ile Thr Arg His Tyr Lys Phe Asn Val Val Met Arg Asn Met
    50                  55                  60

Thr Arg Leu Cys Ser Thr Lys Pro Ile Leu Thr Val Asn Gly Lys Phe
65                  70                  75                  80

Pro Gly Pro Thr Leu Tyr Ala Arg Glu Gly Asp Asn Val Leu Val Lys
                85                  90                  95

Val Val Asn His Val Ala His Asn Val Thr Ile His Trp His Gly Val
            100                 105                 110

Arg Gln Ile Arg Thr Gly Trp Tyr Asp Gly Pro Ala Tyr Ile Thr Gln
        115                 120                 125

Cys Pro Ile Gln Pro Gly Ser Ser Phe Leu Tyr Asn Phe Thr Ile Thr
    130                 135                 140

Gly Gln Arg Gly Thr Leu Leu Trp His Ala His Ile Asn Trp Leu Arg
145                 150                 155                 160

Ala Thr Val His Gly Ala Ile Val Ile Leu Pro Lys Leu Gly Val Pro
                165                 170                 175

Tyr Pro Phe Pro Ala Pro His Lys Glu Ala Val Ile Val Leu Gly Glu
            180                 185                 190

Trp Trp Lys Glu Asp Thr Glu Thr Val Ile Asn Gln Ala Met Gln Leu
        195                 200                 205

Gly Val Gly Pro Asn Ile Ser Asp Ser His Thr Ile Asn Gly His Pro
    210                 215                 220

Gly Pro Leu Ser Glu Cys Ala Ser Ser Gln Asp Gly Phe Lys Leu Ser
225                 230                 235                 240

Val Glu Asn Gly Lys Thr Tyr Met Leu Arg Ile Ile Asn Ala Ala Leu
                245                 250                 255

Asn Asp Asp Leu Phe Phe Lys Val Ala Gly His Glu Leu Thr Val Val
            260                 265                 270

Glu Val Asp Ala Val Tyr Thr Lys Pro Phe Lys Thr Asp Thr Leu Leu
        275                 280                 285

Ile Thr Pro Gly Gln Thr Thr Asn Val Leu Val Arg Ala Asn Gln Gly
    290                 295                 300

Ala Gly Arg Tyr Leu Leu Ser Val Ser Pro Phe Met Asp Ala Pro Val
305                 310                 315                 320

Gln Val Asp Asn Lys Thr Gly Thr Ala Thr Leu His Tyr Ala Asn Thr
                325                 330                 335

Val Ser Ser Ser Met Ala Ser Leu Thr Leu Val Lys Pro Pro Pro Gln
            340                 345                 350

Asn Ala Thr His Ile Val Ser Lys Phe Thr Asp Ser Leu His Ser Leu
        355                 360                 365
```

-continued

```
Asn Ser Lys Glu Tyr Pro Ala Asn Val Pro Gln Thr Val Asp His Ser
    370                 375                 380
Leu Leu Leu Thr Val Gly Val Gly Val Asn Pro Cys Pro Ser Cys Ile
385                 390                 395                 400
Asn Gly Thr Arg Val Val Gly Thr Ile Asn Asn Val Thr Phe Ile Met
                405                 410                 415
Pro Ser Thr Pro Ile Leu Gln Ala His Tyr Tyr Asn Ile Pro Gly Val
                420                 425                 430
Phe Thr Glu Asp Phe Pro Ala Thr Pro Leu His Lys Phe Asn Tyr Thr
                435                 440                 445
Gly Ser Gly Pro Lys Asn Leu Gln Thr Met Asn Gly Thr Arg Val Tyr
    450                 455                 460
Arg Leu Pro Tyr Asn Ala Ser Val Gln Val Val Leu Gln Asp Thr Gly
465                 470                 475                 480
Ile Ile Ser Pro Glu Ser His Pro Ile His Leu His Gly Phe Asn Phe
                485                 490                 495
Phe Val Val Gly Lys Gly Val Gly Asn Tyr Asn Pro Arg Thr Ser Pro
                500                 505                 510
Ser Thr Phe Asn Leu Ile Asp Pro Ile Glu Arg Asn Thr Ile Gly Val
                515                 520                 525
Pro Thr Gly Gly Trp Thr Ala Ile Arg Phe Arg Ser Asp Asn Pro Gly
    530                 535                 540
Val Trp Phe Met His Cys His Phe Glu Val His Thr Ser Trp Gly Leu
545                 550                 555                 560
Lys Met Ala Phe Val Val Asp Asn Gly Lys Arg Pro Ser Glu Thr Leu
                565                 570                 575
Ile Pro Pro Pro Lys Asp Leu Pro Gln Cys
                580                 585

<210> SEQ ID NO 67
<211> LENGTH: 582
<212> TYPE: PRT
<213> ORGANISM: Zea mays

<400> SEQUENCE: 67

Met Ala Thr Pro Tyr Arg Leu Pro Cys Cys Cys Tyr Ala Leu Val Thr
1               5                   10                  15
Val Leu Val Leu Phe Phe Ser Val Asp Ala Thr Glu Gly Ala Ile Arg
                20                  25                  30
Glu Tyr Gln Phe Asp Val Gln Met Thr Asn Val Thr Arg Leu Cys Ser
            35                  40                  45
Ser Lys Ser Ile Val Thr Val Asn Gly Gln Phe Pro Gly Pro Thr Val
    50                  55                  60
Phe Ala Arg Glu Gly Asp Phe Val Val Ile Arg Val Asn His Val
65                  70                  75                  80
Pro Tyr Asn Met Ser Ile His Trp His Gly Ile Arg Gln Leu Arg Ser
                85                  90                  95
Gly Trp Ala Asp Gly Pro Ala Tyr Ile Thr Gln Cys Pro Ile Gln Ser
            100                 105                 110
Gly Gln Ser Tyr Val Tyr Lys Phe Thr Ile Thr Gly Gln Arg Gly Thr
        115                 120                 125
Leu Trp Trp His Ala His Ile Ser Trp Leu Arg Ala Thr Val Tyr Gly
    130                 135                 140
Pro Ile Val Ile Leu Pro Lys Pro Gly Val Pro Tyr Pro Phe Pro Ala
145                 150                 155                 160
```

```
Pro Tyr Asp Glu Val Pro Val Leu Phe Gly Glu Trp Trp Thr Ala Asp
            165                 170                 175

Thr Glu Ala Val Ile Ser Gln Ala Leu Gln Thr Gly Gly Pro Asn
        180                 185                 190

Val Ser Asp Ala Phe Thr Ile Asn Gly Leu Pro Gly Pro Leu Tyr Asn
        195                 200                 205

Cys Ser Ala Lys Asp Thr Phe Lys Leu Lys Val Lys Pro Gly Lys Thr
        210                 215                 220

Tyr Met Leu Arg Ile Ile Asn Ala Ala Leu Asn Asp Glu Leu Phe Phe
225                 230                 235                 240

Ser Ile Ala Gly His Pro Leu Thr Val Val Asp Val Asp Ala Val Tyr
                245                 250                 255

Ile Lys Pro Ile Thr Val Glu Thr Ile Ile Ile Thr Pro Gly Gln Thr
                260                 265                 270

Thr Asn Val Leu Leu Thr Thr Lys Pro Ser Tyr Pro Gly Ala Thr Tyr
            275                 280                 285

Tyr Met Leu Ala Ala Pro Tyr Ser Thr Ala Arg Pro Gly Thr Phe Asp
        290                 295                 300

Asn Thr Thr Val Ala Gly Ile Leu Glu Tyr Glu Asp Pro Thr Ser Ser
305                 310                 315                 320

Pro Pro His Ala Ala Phe Asp Lys Asn Leu Pro Ala Leu Lys Pro
                325                 330                 335

Thr Leu Pro Gln Ile Asn Asp Thr Ser Phe Val Ala Asn Tyr Thr Ala
                340                 345                 350

Arg Leu Arg Ser Leu Ala Thr Ala Glu Tyr Pro Ala Asp Val Pro Arg
        355                 360                 365

Glu Val His Arg Arg Phe Phe Phe Thr Val Gly Leu Gly Thr His Pro
        370                 375                 380

Cys Ala Val Asn Gly Thr Cys Gln Gly Pro Thr Asn Ser Ser Arg Phe
385                 390                 395                 400

Ala Ala Ser Val Asn Asn Val Ser Phe Val Leu Pro Thr Thr Ala Leu
                405                 410                 415

Leu Gln Ser His Phe Ala Gly Lys Ser Arg Gly Val Tyr Ser Ser Asn
                420                 425                 430

Phe Pro Ala Ala Pro Leu Val Pro Phe Asn Tyr Thr Gly Thr Pro Pro
        435                 440                 445

Asn Asn Thr Asn Val Ser Asn Gly Thr Lys Leu Val Val Leu Pro Tyr
450                 455                 460

Gly Thr Ser Val Glu Leu Val Met Gln Gly Thr Ser Ile Leu Gly Ala
465                 470                 475                 480

Glu Ser His Pro Leu His Leu His Gly Phe Asn Phe Phe Val Val Gly
                485                 490                 495

Gln Gly Phe Gly Asn Phe Asp Pro Ala Lys Asp Pro Ala Lys Tyr Asn
            500                 505                 510

Leu Val Asp Pro Val Glu Arg Asn Thr Val Gly Val Pro Ala Ala Gly
        515                 520                 525

Trp Val Ala Ile Arg Phe Arg Ala Asp Asn Pro Gly Val Trp Phe Met
530                 535                 540

His Cys His Leu Glu Val His Val Ser Trp Gly Leu Lys Met Ala Trp
545                 550                 555                 560

Leu Val Leu Asp Gly Glu Arg Pro Asn Glu Lys Leu Leu Pro Pro Pro
                565                 570                 575
```

```
Ser Asp Leu Pro Thr Cys
        580
```

US 10,246,719 B2

MODULATING LACCASE ENZYME TO REGULATE CELL WALL BIOSYNTHESIS AND RECALCITRANCE IN PLANTS

CROSS REFERENCE TO RELATED APPLICATIONS

This application claims priority from U.S. Provisional Application No. 62/361,541 filed Jul. 13, 2016, the entire contents of which are incorporated herein by reference.

STATEMENT REGARDING FEDERALLY SPONSORED RESEARCH OR DEVELOPMENT

This disclosure was made with government support under a research project supported by Prime Contract No. DE-AC05-00OR22725 awarded by the U.S. Department of Energy. The government has certain rights in this invention.

INCORPORATION BY REFERENCE OF SEQUENCE LISTING

The Sequence Listing in the ASCII text file, named as 35158_3416_Seq_ST25.txt of 294 KB, created on Jul. 12, 2017, and submitted to the United States Patent and Trademark Office via EFS-Web, is incorporated herein by reference.

BACKGROUND

Production of renewable fuel from lignocellulosic plant biomass is based on extraction of sugars from plant cell wall material. This extraction process is hampered by the presence of lignin in the cell wall. Lignins contribute to plant "recalcitrance", a term referring to the inherent resistance of plant material to release polysaccharides and other desirable biomaterials from an interwoven matrix of desirable and undesirable materials (Lynd L R. et al., 1991, *Science* 251:1318-1323). Lignins are difficult to break down by physical, chemical and other methods, and processing plant materials to release sugars from lignins requires extensive thermochemical or enzymatic treatment. In addition, lignin processing creates inhibitory byproducts, such as acetylated compounds, that hamper further extraction and fermentation. Acetyl esters released during treatment of cell wall polymers can inhibit saccharification of biomass. The released acetate is also inhibitory to the organisms used to ferment the sugars into useful byproducts. Overcoming plant recalcitrance to releasing biomaterials bound in the cell wall is therefore an issue of primary importance in the development of biofuel technology. Finding ways to alter cell wall composition or structure and reduce the severity of pretreatments is a key goal in developing cost-effective biomass feedstocks for biofuel and bioproduct production. The ability to genetically modify biomass feedstocks can have a direct impact on the ability to extract sugars and therefore yield of transportation fuels from plant biomass. Identifying genes that regulate cell wall biosynthesis and composition and reduce recalcitrance is a critical step for efficient production of biofuel and bioproducts from lignocellulosic biomass.

Lignins, complex interlinking biopolymers derived from hydroxyphenylpropanoids, provide rigidity and structure to plant cell walls for plant growth and transport of water and nutrients, and are significant contributors to plant recalcitrance. Lignins are composed primarily of syringyl (S), guaiacyl (G) and p-hydroxyphenyl (hydroxyl-coumaryl) (H) monolignol subunits, which are derived from sinapyl, coniferyl and p-coumaryl alcohols, respectively. The S/G subunit ratio and resulting structure of plant lignins varies according to the genotype, environment, tissue type and maturity of the plant and as such, lignins are very heterogeneous and can vary significantly between different plants, within different tissues of a single plant and even within a single plant cell (Simmons B A et al., 2010, *Curr Opin Plant Biol.* 13:313-20). This complexity and heterogeneity hinders the development of conversion technology able to process a range of sustainable feedstocks in a cost-effective manner.

Modifying or regulating linkages of lignin with phenolics has been shown to greatly affect biomass digestibility (Li et al., 2014, *PLoS One*, 9, e105115; Wilkerson et al., 2014, *Science*, 344, 90-93). On the other hand, high-level lignin has been shown to be a positive factor on biomass saccharification in rice mutants (Li et al., 2015, *Plant Biotechnol. J.* 13, 514-525; Wu et al., 2013, Biofuels, 6, 183) and artificial cellulose-lignin interactions affect digestibility (Zhang et al., 2016, *Bioresour. Technol.* 200, 761-769), indicating the level of complexity of cell wall interactions and mechanisms. Properties of the cell wall, including composition, intermolecular interactions and interlinking, cellulose crystallinity and even the release of toxic compounds during pretreatment are all factors that affect accessibility and utilization of sugars for biofuel production.

The genus *Populus* represents an economically important tree crop that has been targeted for use in diverse applications from the pulp and paper industry, carbon sequestration and as a feedstock in the lignocellulosic biofuel industry (Dinus R J. et al., 2001, *Crit. Rev. Plant Sci.* 20:51-69).

Identification and manipulation of genes regulating cell wall biosynthesis and recalcitrance is critical both for efficient production of cellulosic sugars and biofuels from plant biomass, and for production of improved cellulose-based products, such as paper and pulp.

Laccases are copper-containing glycoproteins found in a wide range of organisms (Baldrian, 2006, *FEMS Microbiol. Rev.* 30, 215-242; Claus, 2003, *Arch. Microbiol.* 179, 145-150; Dittmer and Kanost, 2010, *Insect Biochem. Mol. Biol.* 40, 179-188; Dittmer et al., 2004, *Insect Biochem. Mol. Biol.* 34, 29-41; McCaig et al., 2005, *Planta*, 221, 619-636.). Although they share significant homology, laccases appear to have functionally diverged within and between phylogenetic clades (Dittmer et al., 2004, *Insect Biochem. Mol. Biol.* 34, 29-41). Bacterial, fungal and insect laccases have been shown to function in the degradation of lignin, whereas higher plant laccases are thought to function in the polymerization of lignin subunits (Sharma and Kuhad, 2008, *Indian J. Microbiol.* 48, 309-316). Additionally, even though laccases retained similar protein domains, molecular modelling suggests differences in protein folding and affinity for interacting with lignin, which may result in divergence of activity in lignin synthesis and degradation (Awasthi et al., 2015, *J. Biomol. Struct. Dyn.* 33, 1835-1849). Laccases are known to function in oxidation reactions involving various inorganic and organic substrates including phenolics and aromatic amines in plants. Studies in *Populus* and *Arabidopsis* suggest that laccases act not only in the biosynthesis of lignin but also may contribute to additional roles of cell wall chemistry or integrity (Ranocha et al., 2002, *Plant Physiol.* 129, 145-155; Ranocha et al., 1999, Zhao et al., 2013). In plants, it was thought that laccases may be involved in lignin biosynthesis based on their capability to oxidize lignin precursors and their localization in lignifying tissues (Bao et al., 1993, Driouich et al., 1992; Ranocha et al., 1999, *Eur. J. Biochem.* 259, 485-495; Sterjiades et al., 1992, *Plant Physiol.* 99, 1162-1168). For example, overexpression of the cotton laccase, GaLACCASE 1 (LAC1), in *Populus* leads to increased lignin content with transgenic plants showing a 2.1%-19.6% increase in total lignin, indicating that laccases are involved in lignin biosynthesis (Wang et al., 2008, *Plant Cell Tissue Organ Cult.* 93, 303-310). In *Arabidopsis*, insertional mutations in three laccase-encoding genes completely abolished lignin accumulation (Zhao et al., 2013, *Plant Cell,* 25, 3976-3987). Interestingly, the three laccases, AtLAC4, 11 and 17, are not paralogous and show homology to different subfamilies of the laccase gene family, suggesting that lignin biosynthesis is not controlled by a single subfamily. A study in *Populus* indicated that transgenic trees, in which expression of the laccase gene PtLAC3 was reduced, showed a threefold increase in phenolic content which accumulated in xylem ray parenchyma cells (Ranocha et al., 2002, *Plant Physiol.* 129, 145-155). In addition, xylem fibre cell walls were dramatically altered leading to severe deformation, indicating a defect in cell wall integrity and supporting the importance of this laccase in normal xylem cell wall structure and integrity. However, there was no significant change in lignin quantity or composition. (Ranocha et al., 2002, *Plant Physiol.* 129, 145-155).

BRIEF SUMMARY OF THE DISCLOSURE

This disclosure provides genetically modified plants characterized by a reduced expression of the LAC2 gene as compared to a control plant.

In some embodiments, the genetically modified plants belong to a genus selected from the group consisting of *Populus, Manihot, Gossypium, Eucalyptus, Medicago, Arabidopsis, Solanum, Oryza* and *Zea*.

In specific embodiments, the genetically modified plants are selected from the group consisting of *Populus balsamifera, Populus deltoides, Populus trichocarpa, Populus tremuloides, Populus tremula, Populus alba* and *Populus maximowiczii*.

In some embodiments, the reduction in LAC2 gene expression is achieved by a method selected from the group consisting of introducing a nucleic acid inhibitor, the CRISPR/Cas system, the Cre/Lox system, the TALEN system, and homologous recombination.

In some specific embodiments, a nucleic acid inhibitor is selected from the group consisting of an antisense RNA, a small interfering RNA, an RNAi microRNA, an artificial microRNA, and a ribozyme.

In another aspect, this disclosure provides improved methods of producing biofuels comprising using a genetically modified plant characterized by a reduced expression of the LAC2 gene.

In yet another aspect, this disclosure provides an expression comprising a nucleotide sequence that is transcribed into a nucleic acid inhibitor of expression of the LAC2 gene, operably linked to a regulatory region that is functional in a plant, wherein the nucleic acid inhibitor is selected from the group consisting of an antisense RNA, a small interfering RNA, an RNAi microRNA, an artificial microRNA, and a ribozyme.

In some embodiments, the regulatory region comprises an inducible promoter or a tissue-specific promoter. In a specific embodiment, the tissue-specific promoter is a xylem-specific promoter.

In some embodiments, this disclosure provides methods for increasing glucose and/or xylose release in a plant or plant cell, comprising introducing into said plant or plant cell an expression vector comprising a nucleotide sequence that is transcribed into a nucleic acid inhibitor of expression of the LAC2 gene operably linked to a regulatory region that is functional said plant or plant cell, and expressing the nucleic acid in said plant or plant cell.

Furthermore, this disclosure provides a plant or plant cell genetically modified to comprise an expression vector disclosed herein.

DETAILED DESCRIPTION OF THE DISCLOSURE

Definitions

Figure 1:
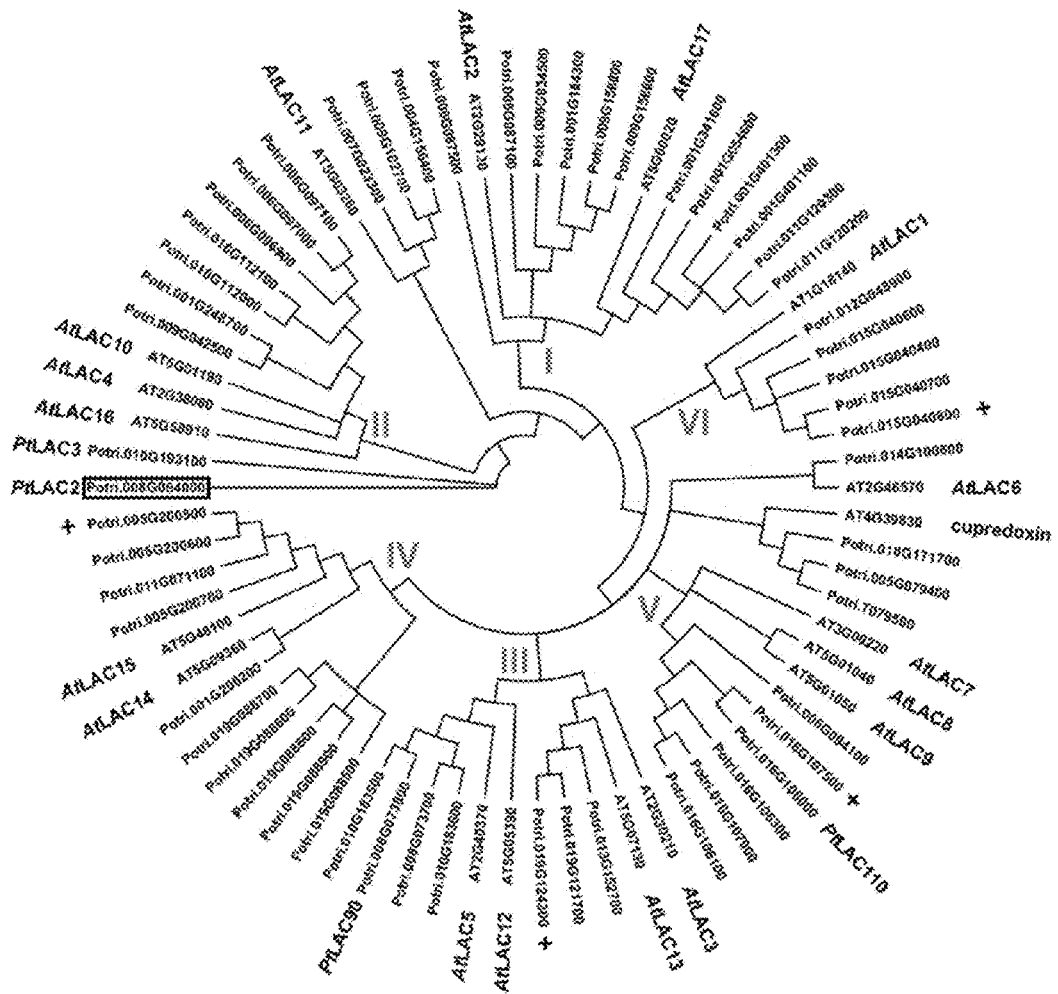
FIG. 1. Phylogenetic analysis of Laccase (LAC) genes from *Populus trichocarpa* and *Arabidopsis thaliana*. The six subfamilies, indicated by Roman numerals, were previously described by McCaig et al. (2005), (*Planta,* 221, 619-636) and *Arabidopsis* LAC genes named accordingly. *Populus trichocarpa* LAC genes were identified through BLAST from Phytozome using *Populus trichocarpa* v3.0 release. A box indicates the *Populus* LAC2 gene described in this analysis. Previously characterized *Populus* LAC genes are indicated by name. Newly annotated LAC genes in *Populus* are indicated by "+".

Unless defined otherwise, all technical and scientific terms used herein have the same meaning as commonly understood by one of ordinary skill in the art to which this invention belongs.

As used herein, the term "about" refers to an approximately +/−10% variation from a given value.

An "altered level of gene expression" refers to a measurable or observable change in the level of expression of a transcript of a gene, or the amount of its corresponding polypeptide, relative to a control plant or plant cell under the same conditions (e.g., as measured through a suitable assay such as quantitative RT-PCR, a Northern blot, a Western blot or through an observable change in phenotype, chemical profile or metabolic profile). An altered level of gene expression can include up-regulated or down-regulated expression of a transcript of a gene or polypeptide relative to a control plant or plant cell under the same conditions. Altered expression levels can occur under different environmental or developmental conditions or in different locations than those exhibited by a plant or plant cell in its native state.

The term "biofuel" refers to any type of fuel which is derived in any way from biomass. In some embodiments, the biofuel in the context of the present invention is a liquid biofuel. The biofuel may mainly comprise an extensively pure compound, thus, may be a biofuel comprising more than 95% of said compound and less than 5% of one or more other compound(s), of more than 80% of said compound and less than 20% of one or more other compound(s) or of more than 75% of said compound and less than 25% of one or more other compound(s). Alternatively, the biofuel may be a mixture of different compounds.

In some embodiments, the biofuel comprises one or more alcohol(s), one or more ester(s), one or more carbonic acid(s), one or more ketone(s), one or more aldehyde(s) or one and/or more terpene(s). In some embodiments, the biofuel comprises one or more alcohol(s), one or more ketone(s) (e.g., acetone), one or more aldehyde(s) and/or comprises one or more ester(s). In some embodiments, the biofuel comprises one or more alcohol(s) and/or comprises one or more ester(s). In some embodiments, the biofuel may comprise more than 50% (v/v), more than 70% (v/v), more than 80% (v/v), more than 90% (v/v) or more than 95% (v/v) of one or more alcohol(s). In some embodiments, these alcohols are aliphatic alcohols (e.g., methanol, ethanol, n-propanol, isopropanol and/or butanol), specifically aliphatic alcohols of the general molecular formula H—$C_nH_{2n}$—OH, even more specifically, one of the first four aliphatic alcohols with n=1-4 (i.e., methanol, ethanol, propanol and/or butanol). In the context of the present invention these alcohols may also be designated as "bioalcohols" (i.e., as "biomethanol", "bioethanol", "biopropanol" and "biobutanol"). Due to its chemical and technical characteristics, in the context of biofuel, butanol is sometimes also designated as "biogasoline". In some embodiments, the alcohol may be a di-, tri or polyalcohol such as, e.g., glycerol. In some embodiments, the biofuel in the context of the present invention comprises more than 50% (v/v), more than 70% (v/v), more than 80% (v/v), more than 90% (v/v), or more than 95% (v/v) ethanol. In a specific embodiment, the biofuel of the present invention comprises at least 90% (v/v) ethanol.

As used herein, the term "biomass" refers to any cellulosic or lignocellulosic raw material and includes materials containing cellulose, and optionally further containing hemicellulose, lignin, starch, oligosaccharides and/or monosaccharides.

The term "cellulose" (also "lignocellulose" or "cellulosic substrate") refers to a structural material that comprises much of the mass of plants. Lignocellulose is composed mainly of carbohydrate polymers (cellulose, hemicelluloses) and an aromatic polymer (lignin).

The term "control plant" as used herein refers to a plant cell, an explant, seed, plant component, plant tissue, plant organ, or whole plant used to compare against transgenic or genetically modified plant for the purpose of identifying an enhanced phenotype or a desirable trait in the transgenic or genetically modified plant. A "control plant" may in some cases be a transgenic plant line that comprises an empty vector or marker gene, but does not contain the recombinant polynucleotide of interest that is present in the transgenic or genetically modified plant being evaluated. A control plant may be a plant of the same line or variety as the transgenic or genetically modified plant being tested, or it may be another line or variety, such as a plant known to have a specific phenotype, characteristic, or known genotype. A suitable control plant would include a genetically unaltered or non-transgenic plant of the parental line used to generate a transgenic plant herein.

As used herein, the term "CRISPR" refers to a RNA-guided endonuclease comprising a nuclease, such as Cas9, and a guide RNA that directs cleavage of the DNA by hybridizing to a recognition site in the genomic DNA.

The term "DNA," as used herein, refers to a nucleic acid molecule of one or more nucleotides in length, wherein the nucleotide(s) are nucleotides. By "nucleotide" it is meant a naturally-occurring nucleotide, as well modified versions thereof. The term "DNA" includes double-stranded DNA, single-stranded DNA, isolated DNA such as cDNA, as well as modified DNA that differs from naturally-occurring DNA by the addition, deletion, substitution and/or alteration of one or more nucleotides as described herein.

The term "exogenous," as used herein, refers to a substance or molecule originating or produced outside of an organism. The term "exogenous gene" or "exogenous nucleic acid molecule," as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG)). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states.

As used herein, the term "fermentation" refers to the enzymatic and/or anaerobic breakdown of organic substances by microorganisms to produce simpler organic compounds such as alcohols. While fermentation may occur under anaerobic conditions, it is not intended that the term be solely limited to strict anaerobic conditions, as fermentation may also occur under aerobic (e.g., in the presence of oxygen) or microaerobic conditions.

The term "gene," as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically engineered" (or "genetically modified") refers to a microorganism comprising a manipulated genome or nucleic acids.

The term "hexose" refers to a monosaccharide with six carbon atoms, having the chemical formula $C_6H_{12}O_6$. Examples of hexose include glucose and fructose.

The term "homolog" means a gene related to a second gene by descent from a common ancestral DNA sequence, therefore, the corresponding polynucleotide/polypeptide has a certain degree of homology, that is to say sequence identity (preferably at least 40%, more preferably at least 60%, even more preferably at least 65%, particularly preferred at least 66%, 68%, 70%, 75%, 80%, 86%, 88%, 90%, 92%, 95%, 97% or 99%). "Type I glutamine synthetase (glnA) gene homolog" furthermore means that the function is equivalent to the function of the Type I glutamrine synthetase (glnA) gene.

"Lignin", as used herein, refers to a complex polymer composed of monolignol subunits, primarily syringyl (S), guaiacyl (G) and p-hydroxyphenyl (H) monolignols, derived from sinapyl, coniferyl and p-coumaryl alcohols, respectively. Differences in the ratio of monolignols, and differences in expression and/or activity of lignin biosynthetic anabolic enzymes, create considerable variability in lignin structures, which differ between species, within species, within different tissues of a single plant and even within a single plant cell.

Lignin "synthesis" or "biosynthesis" refers to the production of lignin in a plant, plant tissue, or plant cell. "Lignin synthesis characteristics" or "lignin biosynthesis characteristics" include the total amount of lignin ("lignin content") in a plant or plant cell, the ratio or amount of monolignol subunits, and expression and/or activity of lignin biosynthetic enzymes. Lignin content, ratio or amount of monolignols, and expression and/or activity of lignin biosynthetic enzymes, can be affected by modulation of the Potri.008G064000 gene, where one or more of these characteristics can be high or low relative to the same characteristic or characteristics in a plant that does not have the same modulation of the Potri.008G064000 gene.

As used herein, the term "nucleic acid" has its general meaning in the art and refers to refers to a coding or non coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non coding region of a genome (i.e. nuclear or mitochondrial).

A "nucleic acid inhibitor" is a nucleic acid that can reduce or prevent expression or activity of a target gene. For example, an inhibitor of expression of Potri.008G064000 can reduce or eliminate transcription and/or translation of the Potri.008G064000 gene product, thus reducing Potri.008G064000 protein expression.

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

The vectors provided herein also can include, for example origins of replication, scaffold attachment regions (SARs) and/or markers. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences typically are expressed as a fusion with the encoded polypeptide. Such tags can be inserted anywhere within the polypeptide, including at either the carboxyl or amino terminus. As described herein, plant cells can be transformed with a recombinant nucleic acid construct to express a polypeptide of interest.

General Description

Disclosed herein are genetically modified plants having modified expression of the *Populus* Potri.008G064000 (LAC2) gene. The inventors provide evidence herein for roles of the *Populus* Potri.008G064000 (LAC2) gene in cell wall chemistry. Without being limited to a particular viewpoint, it is believed that Potri.008G064000 is involved in higher order interactions of cell wall components. The inventors have shown that reduced expression of Potri.008G064000 resulted in an increase in sugar release in knock-down transgenic lines compared to control plants when samples were subjected to a relatively mild pretreatment condition. Down-regulation of LAC2 resulted in a disrupted cell wall assembly phenotype and other pleiotropic consequences, as described below, permitting a pretreatment-dependent increase in release of glucose and xylose.

Potri.008G064000 Alleles, Allelic Variants and Homologs

The inventors have described herein a laccase from *Populus*, PtLAC2, encoded by locus Potri.008G064000, whose altered expression resulted in transgenic *Populus* trees with changes in syringyl/guaiacyl ratios as well as altered sugar release phenotypes.

As used herein, "allelic variants" are alternative forms of the same gene or genetic locus. Each allelic variant has a distinct nucleic acid sequence at the locus of interest. An allelic variant of the Potri.008G064000 (PtLAC2) gene includes the Potri.008G064000 amino acid sequence shown in SEQ ID NO: 7. An allelic variant of the Potri.008G064000 (PtLAC2) gene can also can encode a polypeptide that differs by one or more amino acids from the Potri.008G064000 amino acid sequence shown in SEQ ID NO: 7. Allelic variants can encode different proteins when the difference in nucleic acid sequence results in at least one alteration or deletion in the amino acid sequence between the variants.

An allelic variant of Potri.008G064000 can encode the amino acid sequence as set forth in the Potri.008G064000 amino acid sequence shown in SEQ ID NO: 7, or an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in the Potri.008G064000 amino acid sequence shown in SEQ ID NO: 7. Sequence identity refers to the percent of exact matches between the amino acids of two sequences which are being compared. Where one allelic variant encodes a truncated protein relative to the protein encoded by another allelic variant, percent identity can be determined by comparing the amino acid sequences of the variants along the length of the shorter protein.

This disclosure also provides homologs of the polypeptide encoded by Potri.008G064000. A Potri.008G064000 homolog can be a homolog, ortholog or variant of the polypeptide having the amino acid sequence set forth in the Potri.008G064000 amino acid sequence shown in SEQ ID NO: 7. For example, a Potri.008G064000 homolog can have an amino acid sequence with at least 60% sequence identity, e.g., 60%, 65%, 70%, 75%, 78%, 80%, 81%, 82%, 83%, 84%, 85%, 86%, 87%, 88%, 89%, 90%, 95%, 97%, 98% or 99% sequence identity, to the amino acid sequence set forth in the Potri.008G064000 amino acid sequence shown in SEQ ID NO: 7.

In some embodiments, a homolog of Potri.008G064000 is a functional homolog. A functional homolog is a polypeptide that has sequence similarity to the Potri.008G064000 amino acid sequence shown in SEQ ID NO: 7 and that carries out one or more of the biochemical or physiological function(s) of the polypeptide of the Potri.008G064000 amino acid sequence shown in SEQ ID NO: 7. A functional homolog may be a natural occurring polypeptide and the sequence similarity may be due to convergent or divergent evolutionary events. As such, functional homologs are sometimes designated in the literature as homologs or orthologs or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cell wall-modulating polypeptide or by combining domains from the coding sequences for different naturally-occurring cell wall-modulating polypeptides ("domain swapping"). The term "functional homolog" can also be applied to the nucleic acid that encodes a functionally homologous polypeptide.

A homolog of Potri.008G064000 can be a native Potri.008G064000 protein, i.e., one or more additional copies of the coding sequence for a Potri.008G064000 homolog that is naturally present in the cell. Alternatively, a homolog of Potri.008G064000 can be heterologous to the cell, e.g., a transgenic *Populus* plant can contain the coding sequence for a Potri.008G064000 homolog from an *Arabidopsis* plant, for example. Potri.008G064000 homologs from multiple species are identified in Table 2 (SEQ ID NOS: 60-67). Furthermore, a Potri.008G064000 homolog in *Arabidopsis thaliana* has the Genbank Acc No: NM_129364.4 for the mRNA and NP_565881.1 for the protein.

Modulation of the Potri.008G064000 Gene is Associated with Altered Sugar Release, and S/G Ratio This disclosure further provides for modulation of the Potri.008G064000 gene. "Modulation" refers to changing the expression or activity of the Potri.008G064000 gene.

In one embodiment, the Potri.008G064000 gene can be modulated by increasing or decreasing expression of the gene itself. Methods to modulate expression are disclosed in detail below. In a specific embodiment, Potri.008G064000 gene is modulated by decreasing the expression of the gene.

Modulation of the Potri.008G064000 gene can lead to proteins with altered activity. "Altered activity" includes an increase or decrease in a known activity of a protein encoded by a gene of interest, including loss of an established or proposed function, or gain of a new function. For example, the inventors have determined that modulating the Potri.008G064000 gene, for example, by manipulating the expression of the Potri.008G064000 gene, can affect S/G ratio, and/or sugar release.

Altered S/G ratios in a plant (e.g., *Populus* species) include, for example, alterations from essentially 50% syringyl ("S"):50% guaiacyl ("G") units to essentially 100% syringyl units, or essentially 100% guaiacyl units. The terms "units" and "subunits" are used interchangeably herein. Specific S/G ratios include, for example, greater than 2:1, e.g., 2.1:1, 2.2:1, 2.5:1, 2.8:1, 3.0:1, 3.5:1, 4:1, etc; or less than 2:1, e.g., 0.5:1, 0.8:1, 1:1, 1.2:1, 1.5:1, 1.8:1, or 2:1.3, 2:1.5, 2:1.7, 2:1.9, etc. The ratio of syringyl to guaiacyl units can be increased or decreased, e.g., by 1.2-fold, 1.3-fold, 1.4-fold, 1.5-fold, 1.6-fold, 1.7-fold, 1.8-fold, 1.9-fold, 2.0-fold, 2.1-fold, 2.2-fold, 2.3-fold, 2.4-fold, 2.5-fold, 2.6-fold, 2.7-fold, 2.8-fold, 2.9-fold, 3.0-fold or more than 3.0-fold, in a plant as compared to the corresponding S/G ratio in a control plant (i.e., without the manipulation of the Potri.008G064000 gene). In some cases, the ratio of syringyl units incorporated into lignin in a plant described herein can be increased or decreased, e.g., by 5%, 10%, 15%, 20%, 25%, 30%, 35%, 40%, 45%, 50%, 60%, 70%, 80%, 90%, 100% or more than 100%, as compared to the corresponding ratio in a control plant.

By manipulating the Potri.008G064000 gene, the amount and/or rate of S subunit to G subunit biosynthesis, or the incorporation of S to G subunits into the lignin structure, can be altered. Alteration in the S/G subunit ratio alters the lignin composition of the plant cell wall. Manipulating the Potri.008G064000 gene can thus modulate the lignin composition of a plant.

G units have greater capacity for cross-linking between monomers relative to S units. Thus, increasing the ratio of S/G subunits to greater than 2:1 increases S subunits and decreases G subunits in lignin and thus decreases cross-linking between subunits incorporated into lignin. This makes plants with an S/G ratio greater than 2:1 more degradable than wild-type plants because there is less cross-linkage between lignin units and therefore plants with an S/G ratio greater than 2:1 are more susceptible to extraction processes, which decreases recalcitrance and increases sugar release. Higher S/G ratio has been shown to increase sugar release in *Populus* at values above 2.0. The exact way this occurs is not known though it is speculated that lignin remains intact during saccharification under high temperature and/or pressure. Nevertheless, biomass with an S/G ratio above 2.0 releases more sugar.

"Sugar release" includes high or low release of sugars, also referred to as low or high recalcitrance. "High" sugar release (i.e., low recalcitrance) means that sugar can be extracted more easily, or more sugar can be extracted, from a plant, under conditions that would result in less sugar release in a plant without the particular allelic variant or genetic modification. "Low" sugar release (i.e., high recalcitrance) means that sugar can be extracted less easily, or less sugar can be extracted, from a plant, under conditions that would result in more sugar release in a plant without the particular allelic variant or genetic modification. In one example, sugar release refers to the amount of 5- and 6-carbon sugars that can be recovered from a plant using standard techniques to extract these sugars from plant materials. Sugars that can be released include, but are not limited to, glucose, xylose, fructose, arabinose, lactose, ribose, mannose, galactose, and sucrose. Examples of 5-carbon sugars (pentoses) include xylose, ribose, and arabinose; examples of 6-carbon sugars include glucose, fructose, mannose, and galactose.

Sugar release can be measured, for example, by saccharification analysis. In one example of saccharification analysis, sugars are extracted with alpha-amylase and 3-glucosidase in sodium acetate, followed by an ethanol soxhlet extraction. After drying overnight, water is added, and samples are sealed and reacted. Once cooled, a buffer-enzyme mix with cellulose oxidative enzymes is added and incubated with the sample. After incubation, an aliquot of the saccharified hydrolysate is tested for sugar content/release, such as by addition of glucose oxidase/peroxidase for measuring glucose content, and/or xylose dehydrogenase to measure xylose content.

High or low sugar release can be an increase or decrease in sugar release or sugar recovery of 2%, 5%, 8%, 10%, 15%, 20%, 25%, 30%, 40%, 50%, 60%, 70%, 80%, 90%, or 100% in a plant with a particular modulation of the Potri.008G064000 gene, relative to sugar release or sugar recovery from a plant that does not have the modulation of the Potri.008G064000. In one example, "low" glucose release is glucose release of less than 0.1, 0.15, 0.2, or 0.25 g glucose per g biomass. "High" glucose release is glucose release of 0.3, 0.35, 0.4, or 0.45 g glucose per g biomass or more. "Low" glucose/xylose release is combined release of glucose and xylose of less than 0.2, 0.25, 0.3, 0.35, or 0.4 g combined glucose/xylose per g biomass. "High" glucose/xylose release is combined release of glucose and xylose above 0.4, 0.45, 0.5, 0.55, or 0.6 g combined glucose/xylose per g biomass.

Lignin forms strong bonds with sugars and interferes with access to these carbohydrates, making it difficult to extract the plant's sugars contained in cellulose and hemicellulose. Differences in lignin content alter the sugar release properties of a plant in the extraction process. Lower lignin levels in a plant are associated with higher levels of sugar release, while higher lignin levels are associated with lower levels of sugar release. Thus, sugar release and lignin content can show an inverse correlation. In addition, the higher interactions of cell wall components (including lignins) also determine the amount of sugar that can be released.

In some embodiments, gene modulation is achieved using available gene targeting technologies in the art. Examples of gene targeting technologies include the Cre/Lox system (described in Kühn, R., & M. Torres, R., 2002. *Transgenesis Techniques: Principles and Protocols*, 175-204.), homologous recombination (described in Capecchi, Mario R. 1989. *Science*, 244: 1288-1292), TALENs (described in Sommer et al., 2015. *Chromosome Research*, 23: 43-55, and Cermak et al., 2011. *Nucleic Acids Research*: gkr218.), and CRISPR Cas system as described in Ran F A et al., 2013. *Nature Protocols*.

In one embodiment, Potri.008G064000 (PtLAC2) modulation is achieved by a CRISPR/Cas system. CRISPR-Cas and similar gene targeting systems are well known in the art with reagents and protocols readily available (Mali, P. et al., 2013. *Science*, 339(6121), 823-826; Hsu, P. D. et al., 2014. *Cell*, 157.6: 1262-1278; Jiang et al., 2013. *Nature Biotechnology*, 31, 233-239). Exemplary genome editing protocols are described in Jennifer Doudna, and Prashant Mali, 2016. "*CRISPR-Cas: A Laboratory Manual*" (CSHL Press, ISBN: 978-1-621821-30-4) and Ran, F. Ann, et al. 2013. *Nature Protocols*, 8 (11): 2281-2308.

A CRISPR endonuclease comprises two components: (1) an RNA-dependent nuclease, typically microbial Cas9; and (2) a short "guide RNA" (gRNA or sgRNA) comprising a ~20 nucleotide targeting sequence that directs the nuclease to a location of interest in the genome. When co-expressed with an artificial sgRNA targeting a cellular gene, the Cas9 endonuclease generates double-stranded breaks of DNA at the targeted locus. In addition, when CRISPR endonuclease is supplemented with a stretch of DNA template homologous to the break region, the break is repaired using the supplied homologous DNA template via the process of homologous recombination (HR). CRISPR-mediated HR makes it possible to specifically edit the target DNA sequence and/or alter gene expression.

In one embodiment, modulation of the Potri.008G064000 (PtLAC2) gene is achieved by site-directed mutagenesis to create mutant gene with altered gene expression. Site-directed mutagenesis is described in *Molecular Cloning*, 3rd Ed., *Current Protocols in Molecular Biology*, and U.S. patent application Ser. No. 12/442,143

Inhibitors and Expression Vectors for Modulating the Activity or Expression of Potri.008G064000

Further disclosed herein are nucleic acid inhibitors of expression of Potri.008G064000, or inhibitors of expression of allelic variants of Potri.008G064000, which can be used to reduce expression of the Potri.008G064000 gene and allelic variants thereof, to provide high sugar release, and/or altered S/G ratio. Specific nucleic acid inhibitors include antisense RNA, small interfering RNA, RNAi, microRNA, artificial microRNA, and ribozymes.

Techniques for introducing nucleic acids (inhibitors and expression vectors) into monocotyledonous and dicotyledonous plants are known in the art and include, without limitation, *Agrobacterium*-mediated transformation, viral vector-mediated transformation, electroporation and particle gun transformation, e.g., U.S. Pat. Nos. 5,538,880, 5,204, 253, 6,329,571 and 6,013,863. If a cell or tissue culture is used as the recipient tissue for transformation, plants can be regenerated from transformed cultures if desired, by techniques known to those skilled in the art. See, e.g., Niu et al., 2000. *Plant Cell Rep. V*19:304-310; Chang and Yang, 1996. *Bot. Bull. Acad. Sin.*, V37:35-40 and Han et al., Biotechnology in Agriculture and Forestry, V44:291 (ed. by Y. P. S. Bajaj), Springer-Vernag, (1999).

Nucleic Acid Inhibitors

A number of nucleic acid based methods, including anti-sense RNA, ribozyme directed RNA cleavage, post-transcriptional gene silencing (PTGS), e.g., RNA interference (RNAi), microRNA and artificial microRNA and transcriptional gene silencing (TGS) can be used to inhibit Potri.008G064000 expression in plants. Suitable nucleic acid inhibitors, i.e., nucleic acids capable of inhibiting the expression of a target gene, include full-length nucleic acids of allelic variants of Potri.008G064000, or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant vector is then transformed into plants, as described below and the anti-sense strand of RNA is produced. The nucleic acid segment need not be the entire sequence of the gene to be repressed, but typically will be substantially complementary to at least a portion of the sense strand of the gene to be repressed.

In another method, a nucleic acid can be transcribed into a ribozyme or catalytic RNA, which affects expression of an mRNA. See, U.S. Pat. No. 6,423,885. Ribozymes can be designed to specifically pair with a target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes cleave mRNAs at locations dictated by flanking regions that form complementary base pairs with the target mRNA. See, for example, U.S. Pat. No. 5,254,678; Perriman et al., *PNAS* 92(13):6175-6179 (1995); de Feyter and Gaudron, Methods in Molecular Biology, Vol. 74, Chapter 43, Edited by Turner, P. C., Humana Press Inc., Totowa, N.J. RNA endoribonucleases which have been described, such as the one that occurs naturally in *Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof, of the polypeptide of interest. The length of the sequence that is similar or identical to the sense coding sequence can be from 10 nucleotides to 500 nucleotides, from 15 nucleotides to 300 nucleotides, from 20 nucleotides to 100 nucleotides or from 25 nucleotides to 100 nucleotides. The other strand of the stem portion of a double stranded RNA comprises a sequence that is similar or identical to the antisense strand or a fragment thereof, of the coding sequence of the polypeptide of interest and can have a length that is shorter, the same as or longer than the corresponding length of the sense sequence. In some cases, one strand of the stem portion of a double stranded RNA comprises a sequence that is similar or identical to the 3' or 5' untranslated region or a fragment thereof, of the mRNA encoding the polypeptide of interest and the other strand of the stem portion of the double stranded RNA comprises a sequence that is similar or identical to the sequence that is complementary to the 3' or 5' untranslated region, respectively or a fragment thereof, of the mRNA encoding the polypeptide of interest. In other embodiments, one strand of the stem portion of a double stranded RNA comprises a sequence that is similar or identical to the sequence of an intron or a fragment thereof in the pre-mRNA encoding the polypeptide of interest and the other strand of the stem portion comprises a sequence that is similar or identical to the sequence that is complementary to the sequence of the intron or fragment thereof in the pre-mRNA.

A construct including a sequence that is operably linked to a regulatory region and a transcription termination sequence and that is transcribed into an RNA that can form a double stranded RNA, can be transformed into plants as described below. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330 and 20030180945.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA or an intron in a pre-mRNA encoding a polypeptide of interest or a fragment of such sequences. In some embodiments, the sense or antisense sequence is identical or complementary to a sequence of the regulatory region that drives transcription of the gene encoding a polypeptide of interest. In each case, the sense sequence is the sequence that is complementary to the antisense sequence.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a P-DNA such that the left and right border-like sequences of the P-DNA are on either side of the nucleic acid.

In some embodiments, a suitable nucleic acid inhibitor can be a nucleic acid analog. Nucleic acid analogs can be modified at the base moiety, sugar moiety or phosphate backbone to improve, for example, stability, hybridization or solubility of the nucleic acid. Modifications at the base moiety include deoxyuridine for deoxythymidine and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring or peptide nucleic acids, in which the deoxyphosphate backbone is replaced by a pseudopeptide backbone and the four bases are retained. See, for example, Summerton and Weller, 1997, *Antisense Nucleic Acid Drug Dev.,* 7:187-195; Hyrup et al., *Bioorgan. Med. Chem.,* 4:5-23 (1996). In addition, the deoxyphosphate backbone can be replaced with, for example, a phosphorothioate or phosphorodithioate backbone, a phosphoroamidite or an alkyl phosphotriester backbone.

Expression Vector Modulators of Potri.008G064000 and Uses Thereof.

This disclosure provides methods of altering s/g ratio and sugar release in a plant, comprising introducing into a plant cell an exogenous nucleic acid vector comprising a nucleotide sequence that is transcribed into a nucleic acid inhibitor of expression of the LAC2 gene operably linked to a regulatory region that is functional in a plant as described above, where a tissue of a plant produced from the plant cell has an altered cell wall compared to the cell wall in tissue of a control plant that does not comprise the nucleic acid inhibitor.

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

Some suitable regulatory regions initiate transcription, only or predominantly, in certain cell types. For example, a promoter that is active predominantly in a reproductive tissue (e.g., fruit, ovule or inflorescence) can be used. Thus, as used herein a cell type- or tissue-preferential promoter is one that drives expression preferentially in the target tissue, but may also lead to some expression in other cell types or tissues as well.

Root-active and root-preferential promoters confer transcription in root tissue, e.g., root endodermis, root epidermis or root vascular tissues. Root-preferential promoters include the root-specific subdomains of the CaMV 35S promoter (Lam et al., *Proc. Natl. Acad. Sci. USA,* 86:7890-7894 (1989)), root cell specific promoters reported by Conkling et al., *Plant Physiol.,* 93:1203-1211 (1990) and the tobacco RD2 promoter.

Promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab IR promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis* SUC2 sucrose-H+ symporter promoter (Truernit et al., *Planta,* 196:564-570 (1995)) and thylakoid membrane protein promoters from spinach (psaD, psaF, psaE, PC, FNR, atpC, atpD, cab, rbcS).

Lignin biosynthesis promoters are promoters that drive transcription of nucleic acids encoding enzymes involved in lignin biosynthesis. Examples of lignin biosynthesis promoters include promoters of the switchgrass (*Panicum virgatum*), rice (*Oryza sativa*), corn (*Zea mays*) and wheat (*Triticum aestivum*) homologs of the *Populus* cinnamate 4-hydroxylase, caffeoyl-CoA O-methyltransferase and caffeic acid O-methyltransferase genes. Also suitable are promoters of *Arabidopsis* genes encoding phenylalanin ammonia lyase (genomic locus At3g10340), trans-cinnamate 4-hydroxylase (genomic locus At2g30490), 4-coumarate: CoA ligase (genomic locus At1g51680), hydroxycinnamoyl-CoA:shikimate/quinate hydroxycinnamoyltransferase (genomic locus At5g48930), p-coumarate 3-hydroxylase (genomic locus At2g40890), caffeoyl-CoA 3-O-methyltransferase (genomic locus At4g34050), cinnamoyl CoA reductase (genomic locus At1g15950), ferulate 5-hydroxylase (genomic locus At4g36220), caffeic acid O-methyltransferase (genomic locus At5g54160) and cinnamyl alcohol dehydrogenase (genomic locus At4g34230).

Useful promoters also include cell wall related promoters, such as cellulose biosynthesis promoters. Cellulose biosynthesis promoters are promoters that drive transcription of nucleic acids encoding enzymes involved in cellulose biosynthesis. Examples of cellulose biosynthesis promoters include the promoter of the rice cellulose synthase gene (genomic locus Os08g25710), the promoter of the rice cellulose synthase gene (genomic locus Os08g06380) and the promoter of the rice cellulose synthase-like A2 gene (genomic locus Os10g26630).

Examples of promoters that have high or preferential activity in vascular bundles include the glycine-rich cell wall protein GRP 1.8 promoter (Keller and Baumgartner, *Plant Cell,* 3(10):1051-1061 (1991)), the *Commelina* yellow mottle virus (CoYMV) promoter (Medberry et al., *Plant Cell,* 4(2):185-192 (1992)) and the rice tungro bacilliform virus (RTBV) promoter (Dai et al., *Proc. Natl. Acad. Sci. USA,* 101(2):687-692 (2004)). Promoters having preferential activity in the phloem region (e.g., primary phloem cells, companion cells and sieve cells), the xylem region (e.g., tracheids and vessels), the bundle sheath layer and/or the endodermis are also considered vascular tissue promoters. Promoters that have preferential activity in the pith, cortex, epidermis and/or in the vascular bundles or vascular layers of the stem are considered stem promoters. In some cases, the activity of stem promoters can also be induced by stress like drought.

Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed, but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators and inducible elements. Thus, for example, more than one regulatory region can be operably linked to the sequence of a polynucleotide encoding a Gene Y homolog or other lignin-modulating polypeptide. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Transgenic Plants/Plant Species/Plant Cells

Also disclosed herein are plants and plant cells genetically modified by introduction of the disclosed inhibitors of expression.

A plant or plant cell used in methods of the invention contains a recombinant nucleic acid construct as described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Typically, transgenic plant cells used in methods described herein constitute part or all of a whole plant. Such plants can be grown in a manner suitable for the species under consideration, either in a growth chamber, a greenhouse or in a field. Transgenic plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a transgenic plant can be grown and then selfed (or outcrossed and selfed) to obtain seeds homozygous for the nucleic acid construct. Alternatively, transgenic plants can be propagated vegetatively for those species amenable to such techniques.

Transgenic plant cells growing in suspension culture or tissue or organ culture can be useful for extraction of polypeptides or compounds of interest, e.g., lignin monomers or compounds in a lignin biosynthetic pathway. For the purposes of this invention, solid and/or liquid tissue culture techniques can be used. When using solid medium, transgenic plant cells can be placed directly onto the medium or can be placed onto a filter film that is then placed in contact with the medium. When using liquid medium, transgenic plant cells can be placed onto a floatation device, e.g., a porous membrane that contacts the liquid medium. Solid medium typically is made from liquid medium by adding agar. For example, a solid medium can be any of various mineral salt media, e.g., Murashige and Skoog (MS) medium containing agar and a suitable concentration of an auxin, e.g., 2,4-dichlorophenoxyacetic acid (2,4-D) and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days or about 1-3 days. The use of transient assays is particularly convenient for rapid analysis in different species or to confirm expression of a heterologous Potri.008G064000 allelic variant whose expression has not previously been confirmed in particular recipient cells.

Initial and immediate application of the expression of Potri.008G064000 allelic variants can be made in the bioenergy crops *Populus* and switchgrass, but the application can be extended to other bioenergy crops such as corn, other sources of lignocellulosic biomass and other model plants e.g., *Salix, Miscanthus*, rice and *Medicago*.

For example, the vectors described herein can be used to transform a number of monocotyledonous and dicotyledonous plants and plant cell systems, including alfalfa, ash, beech, birch, canola, cherry, clover, cotton, cottonseed, *eucalyptus*, flax, jatropha, mahogany, maple, mustard, oak, poplar, oilseed rape, rapeseed (high erucic acid and canola), red clover, teak, tomato, walnut and willow, as well as monocots such as barley, bluegrass, canarygrass, corn, fescue, field corn, millet, *miscanthus*, oat, rice, rye, ryegrass, *sorghum*, sudangrass, sugarcane, sweet corn, switchgrass, turf grasses, timothy and wheat. Gymnosperms such as fir, pine and spruce can also be suitable.

The methods and compositions can be used over a broad range of plant species, including species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In some embodiments, a plant is a member of the species *Festuca arundinacea, Miscanthus* hybrid (*Miscanthus×giganteus*), *Miscanthus sinensis, Miscanthus sacchariflorus, Panicum virgatum, Pennisetum purpureum, Phalaris arundinacea, Populus* spp including but not limited to *balsamifera, deltoides, tremuloides, tremula*, alba and *maximowiczii, Saccharum* spp., *Secale cereale, Sorghum almum, Sorghum halcapense* or *Sorghum vulgare*. In certain embodiments, the polynucleotides and vectors described herein can be used to transform a number of monocotyledonous and dicotyledonous plants and plant cell systems, wherein such plants are hybrids of different species.

In one aspect, a plant cell comprising a Potri.008G064000 nucleic acid inhibitor is provided. The plant cell comprises an exogenous nucleic acid, the exogenous nucleic acid comprising a regulatory region operably linked to a polynucleotide that is transcribed into an interfering RNA effective for inhibiting expression of Potri.008G064000 or a Potri.008G064000 allelic variant. The exogenous nucleic acid can further comprise a 3' UTR operably linked to the polynucleotide. The polynucleotide can be transcribed into an interfering RNA comprising a stem-loop structure. The stem-loop structure can comprise an inverted repeat of the 3' UTR.

In another aspect, a plant is provided. The plant comprises any of the plant cells described above. Progeny of the plant also are provided, where the progeny have altered S/g ratio, sugar release and cell wall structure.

Methods of Use of Transgenic Plants

Disclosed herein are methods to increase glucose and/or xylose release in a plant or plant cell, or to alter S:G ratio, by expressing the disclosed inhibitors in plants and plant cells.

Further disclosed herein are improved methods of producing biofuel from cellulosic biomass, by using plants with reduced or inhibited expression or activity of the Potri.008G064000 gene in biofuel production processes. Methods of pretreatment and saccharification of biomass to fermentable sugars, followed by fermentation of the sugars to ethanol, are known in the art.

Articles of Manufacture

The materials and methods described herein are useful for modifying biomass characteristics, such as characteristics of biomass renewable energy source plants. According to the invention, biomass may be derived from a single source, or biomass can contain a mixture derived from more than one source; for example, biomass can contain a mixture of corn cobs and corn stover, or a mixture of grass and leaves. Examples of biomass include, but are not limited to, tree crops such as *Populus*, corn grain, corn cobs, crop residues such as corn husks, corn stover, grasses, wheat, wheat straw, barley, barley straw, hay, rice straw, switchgrass, waste paper, sugar cane bagasse, *sorghum*, soy, components obtained from processing of grains, trees, branches, roots, leaves, wood chips, sawdust, shrubs and bushes, vegetables, and fruits.

Lignin itself, which can be gathered from transgenic plants provided herein, can be converted into valuable fuel additives. Lignin can be recovered from any bioethanol production process using agricultural materials such as straw, corn stalks and switchgrass engineered to have increased lignin content. Lignin can be combusted to provide heat and/or power for the ethanol process; however, increasing the value of the lignin by converting it to higher value fuel additives can significantly enhance the competitiveness of bioethanol technology. Lignins removed from wood pulp as sulphates can be used as dust suppression agents for roads, as dispersants in high performance cement applications, water treatment formulations and textile dyes or as raw materials for several chemicals, such as vanillin, DMSA, ethanol, torula yeast, xylitol sugar and humic acid.

Seeds of transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material or a label inserted within the package. The package label may indicate that the seed herein incorporates transgenes that provide altered S/G lignin ratio in one or more tissues of plants grown from such seeds.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The present disclosure is further illustrated by the following non-limiting examples.

EXAMPLES

Example 1: Materials and Methods

Phylogenic and Sequence Analysis

Protein sequences of 53 *Populus trichocarpa* laccases were collected from Phytozome v10.3 [available at the Plant Comparative Genomics portal of the Department of Energy's Joint Genome Institute website]: *Populus trichocarpa* v3.0. Protein sequences of Laccases from *Arabidopsis thaliana* were collected from TAIR [The *Arabidopsis* Information Resource (TAIR) website] (Table 1). All other laccase sequences from other plant species were collected from phytozome (Table 2). Phylogenetic tree was constructed with neighbour-joining program using MEGA (Molecular Evolutionary Genetics Analysis) software (Tamura et al., 2011, *Mol. Biol. Evol.* 28, 2731-2739). Boostrap values were calculated from 500 independent runs. Sequence alignments were generated using CLC workbench software using neighbour-joining method (CLC BIO, Aarhus, Denmark). Signal sequences were determined based on TargetP software (available from Center for Biological Sequence Analysis at the Technical University of Denmark).

Generation of Transgenic Plants

A 201-bp fragment from the 3'UTR of PdLAC2 was cloned in the binary vector pAGSM552, deposited in GenBank (KP259613) and used in *Agrobacterium*-mediated transformation on *Populus deltoides* 'WV94' at ArborGen Inc (Ridgeville, S.C.) as described previously (Biswal et al., 2015, *Biotechnol. Biofuels*, 8, 41). A total of eight independent transformation events or lines were obtained, along with five ramets for each transgenic event, together with equal numbers of ramets for empty vector transformed control plants, were propagated at Oak Ridge National Laboratory greenhouses at constant 25° C. and 16-h day length. All plants were initially grown in Leach tubes and transferred to larger pots, and after six months of growth, plant height and stem diameter were measured, stem samples were collected and air-dried for cell wall chemistry analyses. Primers used for generating RNAi fragment were as follows:

```
                                          (SEQ ID NO: 1)
PdLAC2 RNAi F:    5' GTATCGTATA GTCTGAAGATCTGG (SEQ ID NO: 2)
PdLAC2 RNAi R:    5' GGAATCAAAGTGCCAAATCC.
``` qRT-PCR Assays

Xylem samples were collected for three ramets each of the two independent transgenic lines and three independent empty vector control plants. RNA was extracted using the Spectrum Plant Total RNA Kit (Sigma, St. Louis, Mo.) with a slight modification. Such that 850 μL of prewarmed (65°

C.) cetyltrimethyl ammonium bromide (CTAB) buffer containing 10 μL of bmercaptoethanol (Sigma) was added to 100 mg fresh weight sample, vortexed for 5 min and incubated at 65° C. for 5 min. Then, 600 μL of chloroform: isoamyl alcohol (24:1 v:v) was added and supernatant was passed through a filter column (Sigma). The filtrate was diluted with 750 μL of 95% EtOH and passed through Sigma binding column. Sigma protocol was followed including on-column DNase digestion per manufactures instructions (Sigma). cDNA was created using 1 μg of RNA using Thermo Fisher Scientific 1st strand cDNA synthesis kit according to manufacturer's instructions. The 1st strand reaction was diluted to 200 and 1.4 μL used per reaction for qRT-PCR analysis. qRT-PCR was performed using STEPONEPLUS™ Real-Time PCR system (Applied Biosystems, Foster City, Calif.) using SYBR green reaction mix (Bio-Rad Life Sciences, Hercules, Calif.) according to manufacturer's recommendations for 20 μL reactions. Gene expression was calculated using DDcT method (Livak and Schmittgen, 2001, *Methods*, 25, 402-408) using 18s ribosomal subunit for template normalization. Primers used were as follows:

```
                                              (SEQ ID NO: 3)
18sqF        5' AATTGTTGGTCTTCAACGAGGAA (SEQ ID NO: 4)
18sqR        5' AAAGGGCAGGGACGTAGTCAA (SEQ ID NO: 5)
LAC2qF       5' CTTGCGCTATAAGGGAACCA (SEQ ID NO: 6)
LAC2qR       5' CCCGACACCGATAGTGAAGT
```

Molecular Beam Mass Spectrometry Assay

Four mg of dried, ground [20/80 mesh] stem biomass was placed into a pyrolysis molecular beam mass spectrometry chamber, and then, using 17 eV electron impact ionization, mass spectral data were acquired on a MerlinAutomation data system version 3.0 from 30 to 450 m/z (Sykes et al., 2009, *Methods Mol. Biol.* 581, 169-183). Lignin estimates were determined as described previously (Sykes et al., 2009, *Methods Mol. Biol.* 581, 169-183). S/G ratios were determined by summing the area under the peaks attributed to syringyl moieties (i.e. m/z 154, 167, 168, 182, 194, 208 and 210) and dividing this area by the area under the peaks attributed to guaiacyl moieties (i.e. m/z 124, 137, 138, 150, 164 and 178).

Saccharification Assay

Biomass was extracted with a-amylase (Spirizyme Ultra—0.25%) and α-glucosidase (Liquozyme SC DS—1.5%) in 0.1 M sodium acetate (24 h, 55° C., pH 5.0) to remove possible starch content (16 mL enzyme solution per 1 g biomass). This was followed by an ethanol (95% v/v) Soxhlet extraction for an additional 24 h to remove extractives. After drying overnight, 5 mg (±0.5 mg) of biomass was weighed in triplicate into one of 96 wells in a solid Hastelloy microtitre plates and 250 μL of water was added. Samples are then sealed with silicone adhesive, Teflon tape. For pretreatment, the samples were reacted at 180° C. for 17.5 min. Once cooled 40 lL of buffer-enzyme stock was added. The buffer-enzyme stock was 8% CTec2 (Novozymes, BagsvaErd, Denmark) (excess enzyme loading of 70 mg/g biomass) in 1 M sodium citrate buffer. The samples were then gently mixed and left to statically incubate at 50° C. for 70 h. After 70-h incubation, an aliquot of the saccharified hydrolysate was diluted and tested using megazymes GOPOD (glucose oxidase/peroxidase) and XDH assays (xylose dehydrogenase). Results were calculated using standard curves created from mixtures of glucose and xylose.

Glycosyl Composition and Metabolite Profiling

Cell wall glycosyl composition analysis was performed by combined gas chromatography/mass spectrometry (GC/MS) of the per-O-trimethylsilyl (TMS) derivatives of the monosaccharide methyl glycosides produced from the sample by acidic methanolysis as described previously (Santander et al., 2013, *Microbiology*, 159, 1471-1486). Briefly, the samples (between 200 and 500 μg) were heated with methanolic HCl in a sealed screw-top glass test tube for 18 h at 80° C. After cooling and removal of the solvent under a stream of nitrogen, the samples were treated with a mixture of methanol, pyridine and acetic anhydride for 30 min. The solvents were evaporated, and the samples were derivatized with TRI-SIL® (Pierce, Waltham, Mass.) at 80° C. for 30 min. GC/MS analysis of the TMS methyl glycosides was performed on an Agilent 7890A GC interfaced to a 5975C MSD, using an Supelco Equity-1 fused silica capillary column (30 m 9 0.25 mm ID).

For metabolite profiling, 25 mg of actively dividing xylem tissues lyophilized and ground with a Wiley mill were twice extracted from each transgenic line and controls with 2.5 mL 80% ethanol overnight and then the extracts combined prior to drying a 0.50-mL aliquot in a nitrogen stream. As an internal standard, 75 μL of sorbitol at 1.0 mg/mL was added to the first extract. Dried extracts were dissolved in acetonitrile, followed by TMS derivatization and analysed by GC-MS, as described elsewhere (Jung et al., 2009, *Science*, 324, 89-91; Li et al., 2012, *Biotechnol. Biofuels* C7-2, 5, 1-13). Metabolite peaks were extracted using characteristic mass-to-charge (m/z) ratio and quantified by area integration, and the concentrations were normalized to the quantity of the internal standard (sorbitol) recovered and the amount of sample extracted, derivatized and injected. A large user-defined database of mass spectral electron impact ionization fragmentation patterns of TMS-derivatized compounds (~2300 signatures) was used to identify the metabolites of interest. Unidentified metabolites were represented by their retention time and key m/z ratios. The metabolite data were presented as fold changes of the transgenic line vs. the average of the control lines. Student's t-tests were used to determine whether differences were statistically significant ($P \leq 0.05$).

Example 2: Phylogenetic Analysis of *Populus* LAC2

As a first step to understanding the phylogenetic diversity of *Populus* laccases, the *Populus* and *Arabidopsis* genomes were queried for laccase-like genes using BLAST in both Phytozome and TAIR databases (Goodstein et al., 2012, *Nucleic Acids Res.* 40, D1178-D1186; Huala et al., 2001, *Nucleic Acids Res.* 29, 102-105). A total of 17 *Arabidopsis* laccases were found, as previously described (McCaig et al., 2005, *Planta*, 221, 619-636; Turlapati et al., 2011, *Planta*, 233, 439-470), along with 53 *Populus* laccases, 49 of which were previously described utilizing an earlier draft of the *Populus trichocarpa* genome (Lu et al., 2013, *Proc. Natl Acad. Sci. USA*, 110, 10848-10853). Utilizing the new draft annotation, four additional laccases distributed across different subfamily categories were identified.

Utilizing the 53 *Populus* and the 17 *Arabidopsis* laccases and a cupredoxin-like gene as an out-group, an amino acid-based phylogeny was constructed for the *Populus* and *Arabidopsis* laccases based on the neighbor-joining method (FIG. 1). The tree created from this analysis places the *Populus* laccases in generalized subfamilies relative to previously reported *Arabidopsis* laccase phylogeny (McCaig et al., 2005, *Planta*, 221, 619-636; Turlapati et al., 2011, *Planta*, 233, 439-470). That is, *Arabidopsis* laccases have been clustered into six arbitrary subfamilies with the expanded *Populus* laccases distributed fairly equally across all subfamilies. PtLAC3, which was previously shown to affect xylem fibre cell wall integrity (Ranocha et al., 2002, *Plant Physiol.* 129, 145-155), is placed in subfamily II. AtLAC4 and AtLAC11 are also found within subfamily II and, when disrupted together with AtLAC17, completely abolished lignin accumulation in *Arabidopsis* (Zhao et al., 2013, *Plant Cell*, 25, 3976-3987). PtLAC3 shows highest homology to PtLAC2 (i.e. 90% amino acid identity).

To characterize the protein domain structure of PtLAC2, we identified the closest related laccases from a number of higher plant species including *Manihot esculenta* (Cassava), *Gossypium raimondii* (cotton), *Eucalyptus grandis*, *Medicago truncatula*, *Arabidopsis thaliana*, *Solanum tuberosum* (potato), *Oryza sativa* (rice) and *Zea mays* (corn). Sequences were derived from BLAST search performed from genomes available in Phytozome, and alignments were based on amino acid sequence (SEQ ID NOS: 7-59). Closer examination of the encoded protein domains of PtLAC2 and its homologs indicates that these homologs all contain the four conserved copper-binding regions (CBR), including all ten histidines and one cysteine embedded in the CBR I (HWHG) [position 108-111 based on PtLAC2], CBR II (HAH) [position 153-155], CBR III (HP 9 HLH) [position 506-512] and CBR IV (HCH) [position 568-570] (FIGS. 7 and 8). Analysis of conservation of the CBR for all *Populus* laccases indicated all contain these conserved motifs except Potri.015G040800 which appears to be missing the N-terminal region of the protein including CBR I. PtLAC2 does contain a predicted N-terminal signal sequence between residues 1 and 23 and a predicted cleavage site between residues 23 and 24, placing this laccase in the secretory pathway (Petersen et al., 2011, *Nat. Methods*, 8, 785-786). Additional analysis of all *Populus* laccases with respect to the presence of signal sequence indicated all laccases except for four (PtLAC3, Potri.005G200600, Potri.005G200500 and Potri.015G040800) contained a predicted signal sequence.

Figure 2:
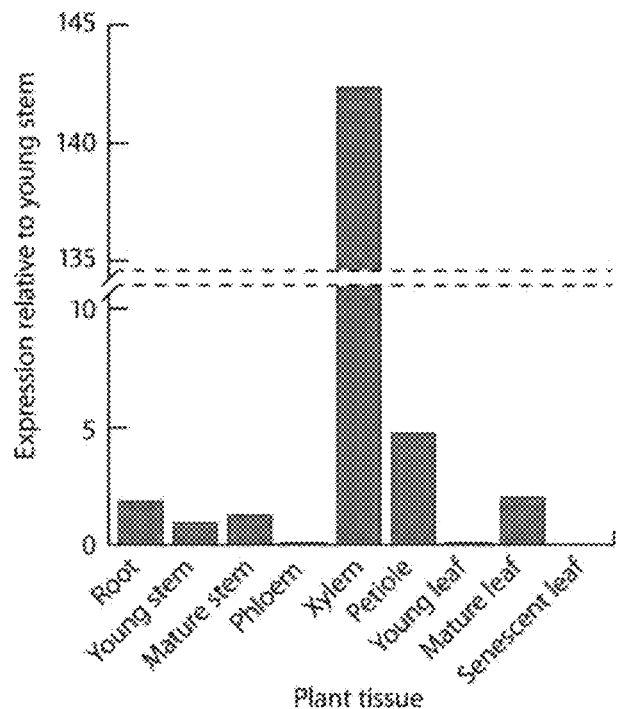
FIG. 2. Expression of PdLAC2 across *Populus deltoides* tissue types. Relative fold expression was calculated using $\Delta\Delta C_t$ relative to young stem.

In the qRT-PCR analysis, LAC2 had the highest expression in xylem tissue compared to other analysed tissues from *Populus deltoides* (FIG. 2). Based on previous expression analysis of *Populus* laccases (Lu et al., 2013, *Proc. Natl Acad. Sci. USA*, 110, 10848-10853), all laccase paralogs clustering in subfamily II also showed high xylem expression with the exception of Potri.001G248700 which showed relatively low xylem expression compared to other analyzed tissues. The overlapping expression profiles of the *Populus* laccases and sequence similarities suggest there may be functional redundancy within this group.

Example 3: Reduction in PtLAC2 Expression Leads to Altered Growth Phenotypes in *Populus*

Figure 3:
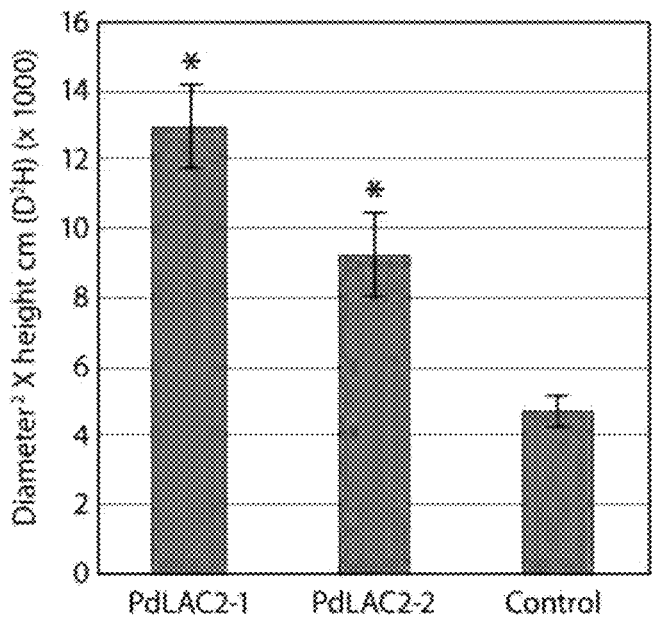
FIG. 3. Estimated above-ground biomass of transgenic *Populus* samples. Above-ground biomass was estimated using the formula Diameter$^2$×Height cm (D$^2$H). *Significant compared to the control, P-value≤0.01.
Figure 4:
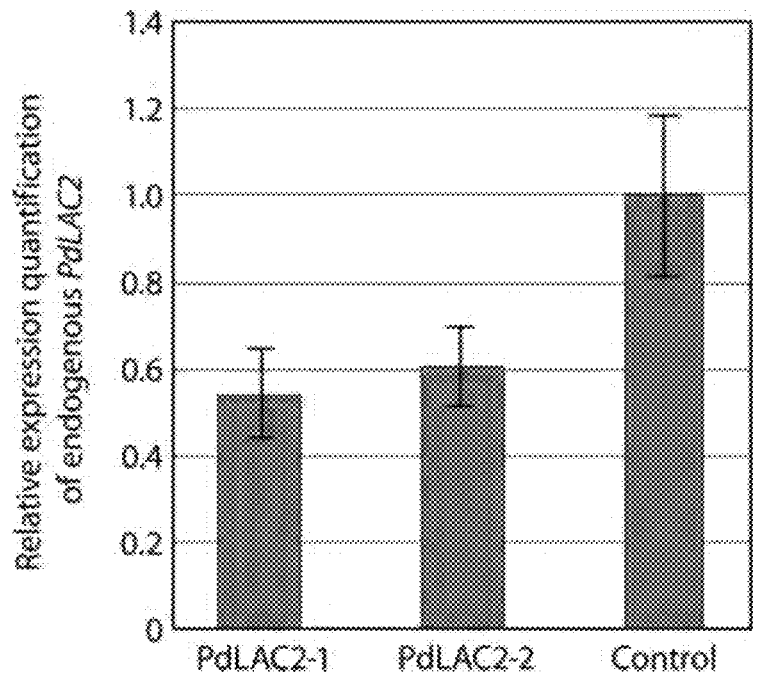
FIG. 4. Relative gene expression of endogenous PdLAC2 in RNAi transgenic lines. PdLAC2-1 and PdLAC2-2 show reduced expression of endogenous PdLAC2 by 50% and 40%, respectively, compared to control plants.

Previous analysis of *Populus* laccases based on antisense expression of PtLAC1, PtLAC3, PtLAC90 and PtLAC110 did not show any change in lignin quantity or composition which was attributed to functional redundancy or specialized function outside of lignin biosynthesis (Ranocha et al., 2002, *Plant Physiol.* 129, 145-155). The only observed defects were observed in PtLAC3 antisense lines which showed deformed xylem fibre cell walls and an accumulation of undefined phenolics preferentially in xylem (Ranocha et al., 2002, *Plant Physiol.* 129, 145-155). To gain further understanding of the function of laccases in subfamily II in *Populus*, transgenic lines expressing an RNAi fragment which specifically targeted LAC2 in *P. deltoides* were created. This genetic background was utilized for the ease of transformation. The RNAi fragment was designed using the 3' UTR of PdLAC2, and expression was driven by the UBIQUITIN3 constitutive promoter. Eight independent transgenic lines were generated for analysis. Here, the results for the two top performing lines, PdLAC2-1 and PdLAC2-2 are presented. Analysis of transgenic lines compared to empty vector control plants showed an increase in above-ground biomass in the two lines, as measured by diameter$^2$×height ($D^2H$) (FIG. 3). Utilizing single stem biomass has previously been shown to provide an estimation of above-ground biomass (Crow, 1978, *Forest Sci.* 24, 110-114; Ter-Mikaelian and Korzukhin, 1997, *Forest Ecol. Manag.*, 97, 1-24; Tuskan and Rensema, 1992, *Can. J. For. Res.* 22, 348-354). Besides the significant increase in growth, no other developmental or anatomical phenotype was observed in these transgenic lines. To confirm that the biomass phenotype was consistent with a reduction in transcript level due to overexpression of PdLAC2 RNAi fragment, qRT-PCR analysis was performed on these lines and the level of PdLAC2 endogenous expression was determined. Three independent empty vector control lines were pooled together and represented in the analysis as control. Both PdLAC2 RNAi lines showed a reduction in PdLAC2 transcript by 40% and 50%, for PdLAC2-1 and PdLAC2-2, respectively (FIG. 4), confirming a reduction in PdLAC2 transcript in the RNAi transgenic lines.

Figure 5:
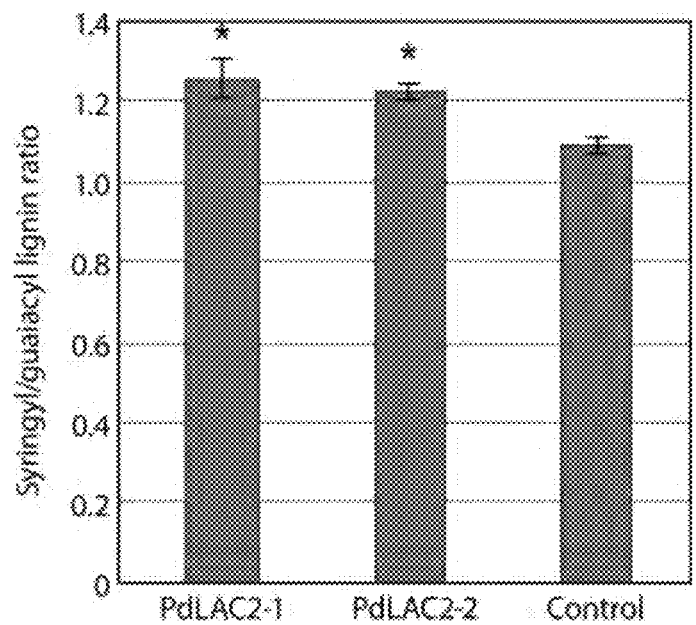
FIG. 5. Syringyl/guaiacyl lignin ratio in PdLAC2 RNAi transgenic lines. Both PdLAC2-1 and PdLAC2-2 show an increase in S/G ratio compared to control lines. *Significant compared to the control, P-value<0.01.

Example 4: Reduction in LAC2 Transcript Leads to Alteration in S/G Ratio Although not Total Lignin Quantity Based on molecular beam mass spectrometry (MBMS) measurements from PdLAC2 RNAi lines, there were no detectable decrease in lignin content for either of the transgenic lines compared to the empty vector controls. However, the two transgenic knock-down PdLAC2 lines showed a significant increase in S/G lignin ratio (FIG. 5). Specifically, the transgenic lines showed an increase leading to 1.26 and 1.22 S/G ratios, respectively, compared to 1.10 for control lines.

Example 5: Reduction in PdLAC2 Transcript Leads to Changes in Metabolite Profiling To explore how reduction in PdLAC2 may affect cell wall-related metabolite profiles, metabolomics analysis was conducted using developing xylem tissues from PdLAC2-1 and PdLAC2-2 lines. Both RNAi lines contained reduced monosaccharides concentrations, including glucose, galactose and fructose, yet no significant effect on sucrose. The organic acids, malic acid, fumaric acid and oxalomalic acid were reduced in both lines, and succinic acid was also reduced in PtLAC2-1, although other organic acids, including maleic acid and a-ketoglutaric acid, were not affected. Citric acid and aconitic acid were increased in PtLAC2-1. Both mono- and digalactosylglycerol were elevated in both RNAi lines. PtLAC2-1 also had a large number of known and partially identified phenolic glycosides that accumulated, including coumaroyl and caffeoyl glycoside conjugates, several flavonoids, modified carbohydrates (e.g. dehydro, anhydro and methylated sugars) that were conjugated to aromatic metabolites, salicortin and its degradation product 6-hydroxy-2-cyclohexenone-1-carboxylic acid.

Among the largest accumulations observed were a 4.88-fold increase in a late-eluting (19.10 min) coumaric acid rhamnosylglucoside and a 2.81-fold increase in a dicaffeoyl shikimic acid conjugate that together are indicative of irregular cell wall assembly. Interestingly, coniferin was the only monolignol glucoside that increased, whereas syringin was unchanged, as were the detectable guaiacyl and syringyl lignans.

Figures 6A, 6B, 6C, 6D, 6E, 6F:
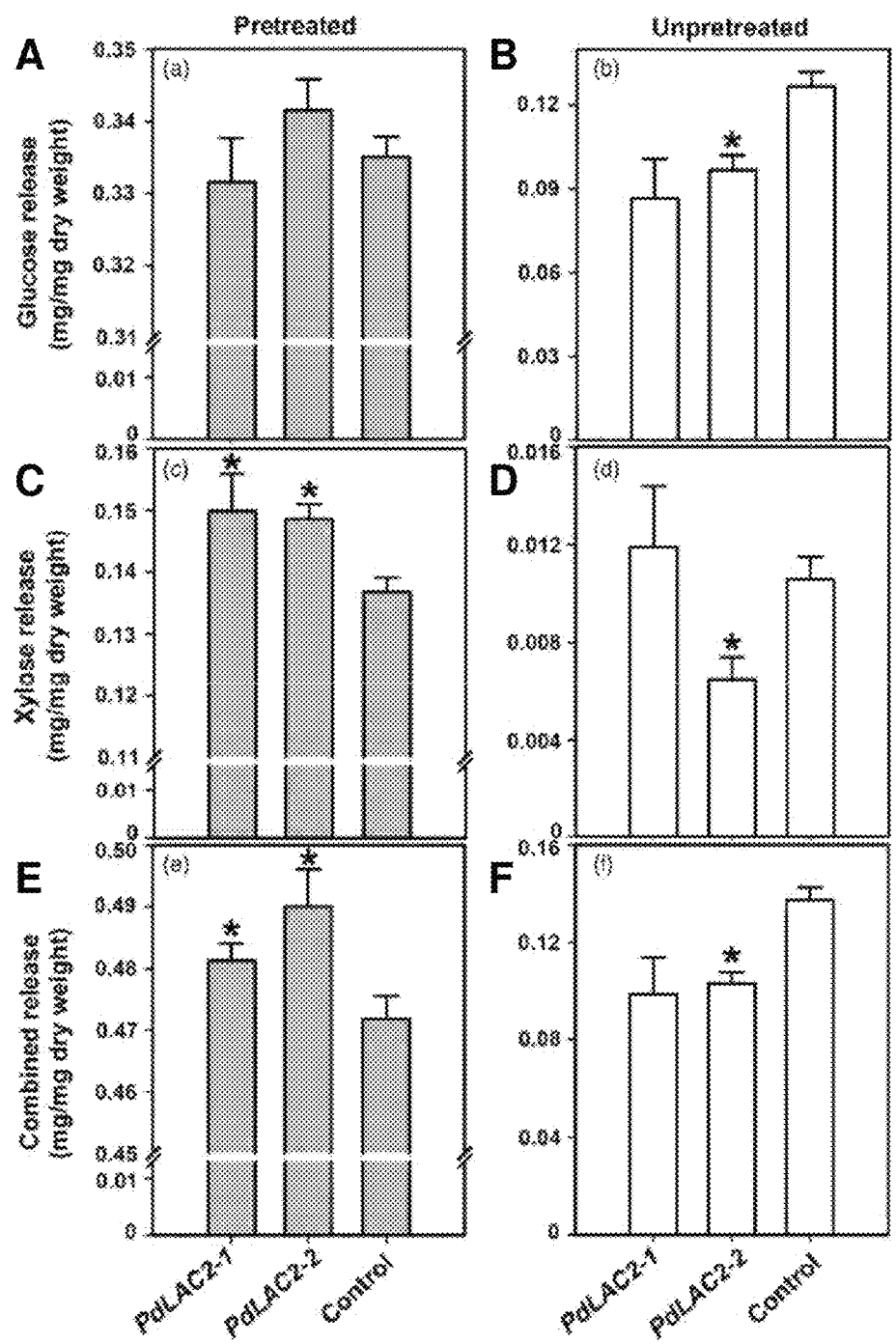
FIGS. 6A-6F. Xylose and glucose release assay of transgenic samples under liquid hot water (LHW) pretreatment and un-pretreated. Samples were collected with mild LHW pretreatment (A, C, E) and no pretreatment prior to sugar extraction (B, D, F). Rates of xylose release from LHW pretreatment and un-pretreatment are shown in (A) and (B). Rates of glucose release from LHW pretreatment and un-pretreatment are shown in (C) and (D). Rates of combined xylose and glucose release are shown in (E) and (F). *Significant compared to the control, P-value<0.01.

Example 6: Reduction in PdLAC2 Transcript Leads to Increased Five and Six Carbon Sugar Release To assess the effect of irregular cell wall assembly on extracting sugars, a mild pretreatment condition of hydrothermal, or liquid hot water (LHW), as well as no pretreatment (unpretreated) extraction procedure were evaluated for sugar release. FIG. 6 shows the xylose and glucose release from the transgenic samples from both no pretreatment and LHW pretreatment. As expected, biomass treated with LHW showed greater sugar release, a 10-fold difference, compared to un-pretreated biomass. This mild pretreatment led to a small but significantly greater release of xylose (FIG. 6C). However, with no pretreatment, control lines generally showed a greater release of glucose and xylose with the exception of PdLAC2-1 (FIG. 6B and FIG. 6D). This discrepancy in saccharification of PdLAC2 RNAi lines compared to controls using the LHW pretreatment vs the un-pretreated conditions could be attributed to a difference in the manner in which lignin is interacting with the polysaccharides in the cell wall of the PdLAC2 RNAi lines. That is, there may be structural differences within the cell walls that require some thermal or chemical incubation leading to perturbed recalcitrance with a mild pretreatment.

In order to eliminate the possibility that the PdLAC2 RNAi lines simply contain more total sugars prior to extraction, the total carbohydrates for each line including the controls were quantified. And in fact, the PdLAC2 RNAi lines did not contain higher fractions of sugars in cell walls compared to controls. Interestingly, control lines showed higher sugar quantification but with LHW pretreatment still show lower total sugar release thus providing additional evidence for a possible mechanism involving disruption of interlinked structural components in PdLAC2 knockdown cell walls.

In summary, the examples herein demonstrate that the reduction in the LAC2 expression through RNAi mediated knock-down resulted in biomass with altered cell wall chemistry leading to a pretreatment-dependent reduction of recalcitrance seen through increased xylose and combined xylose and glucose release. It was observed that the knockdown transgenic plants also exhibited increases in S/G ratio and a significant change in metabolite profiles showing an increase in phenolic compounds related to hydroxycinnamoyl glycoside conjugates, salicortin metabolism and flavonoid production. In addition, the knock-down transgenic trees also showed an increase in above-ground biomass compared to controls. Without being limited by one explanation or theory, it is postulated that LAC2 is involved in higher order interactions of cell wall components. An increase in sugar release was only observed in knock-down transgenic lines when samples were subjected to a relatively mild pretreatment condition (FIG. 6A, FIG. 6C and FIG. 6E), therefore the major components of the cell wall have not been disrupted by the reduction in LAC2 expression. Total lignin content as well as quantities of major sugar components were also unchanged in LAC2 knockdown plants. However, when energy is added to the LAC2 transgenic samples, through hot water pretreatment, a significant increase in sugar release was observed, suggesting that cell wall components are less associated and more amenable to deconstruction.

TABLE 1

The list of *Populus trichocarpa* laccases and their GenBank accession numbers.

| Potri.ID (v3.0) | Genebank ID | SEQ ID NO |
|---|---|---|
| Potri.001G054600 | XP_002299296 | 21 |
| Potri.001G184300 | XP_002298223 | 27 |
| Potri.001G206200 | XP_002299682 | 53 |
| Potri.001G248700 | XP_002299828 | 14 |
| Potri.001G341600 | XP_002300066 | 20 |
| Potri.001G401100 | XP_006370270 | 25 |
| Potri.001G401300 | XP_006370271 | 22 |
| Potri.004G156400 | XP_002305436 | 18 |
| Potri.005G200500 | XP_002307536 | 55 |
| Potri.005G200600 | XP_002307537 | 54 |
| Potri.005G200700 | XP_002307538 | 57 |
| Potri.006G087100 | XP_002308164 | 23 |
| Potri.006G087500 | XP_002309069 | 19 |
| Potri.006G094100 | XP_002308196 | 36 |
| Potri.006G096900 | XP_002308208 | 15 |
| Potri.006G097000 | XP_002308209 | 12 |
| Potri.006G097100 | XP_006387495 | 13 |
| Potri.007G023300 | XP_002310245 | 16 |
| Potri.008G064000 | XP_002311202 | 7 |
| Potri.008G073700 | XP_002312186 | 32 |
| Potri.008G073800 | XP_002312187 | 33 |
| Potri.009G034500 | XP_002313424 | 26 |
| Potri.009G042500 | XP_002314124 | 9 |
| Potri.009G102700 | XP_002313847 | 17 |
| Potri.009G156600 | XP_006379352 | 28 |
| Potri.009G156800 | XP_006379354 | 24 |
| Potri.010G183500 | XP_002315130 | 34 |
| Potri.010G183600 | XP_002315131 | 31 |
| Potri.010G193100 | XP_002316233 | 8 |
| Potri.011G071100 | XP_006377535 | 56 |
| Potri.011G120200 | XP_002317504 | 30 |
| Potri.011G120300 | XP_002317505 | 29 |
| Potri.012G048900 | XP_002317883 | 39 |
| Potri.013G152700 | XP_002319955 | 38 |
| Potri.014G100600 | XP_002320207 | 42 |
| Potri.015G040400 | XP_002322091 | 35 |
| Potri.015G040600 | XP_006374192 | 37 |
| Potri.015G040700 | XP_006374190 | 58 |
| Potri.015G040800 | XP_006374190 | 59 |
| Potri.016G106000 | XP_006373961 | 45 |
| Potri.016G106100 | XP_002322939 | 52 |
| Potri.016G106300 | XP_006373964 | 49 |
| Potri.016G107500 | XP_006373961 | 43 |
| Potri.016G107900 | XP_002322939 | 50 |
| Potri.016G112000 | XP_002322961 | 10 |
| Potri.016G112100 | XP_002322962 | 11 |
| Potri.019G088500 | XP_006371480 | 44 |
| Potri.019G088600 | XP_002325572 | 41 |
| Potri.019G088700 | XP_002325572 | 46 |
| Potri.019G088800 | XP_006371482 | 47 |
| Potri.019G088900 | XP_002325575 | 40 |
| Potri.019G121700 | XP_002326089 | 48 |
| Potri.019G124300 | XP_002326089 | 51 |

TABLE 2

LAC2 homologs.

| Name | Organism | SEQ ID NO |
|---|---|---|
| Manes.07G125000.1 | *Manihot esculenta* | 60 |
| Gorai.011G279600.1 | *Gossypium raimondii* | 61 |
| Eucgr.G03028.1 | *Eucalyptus grandis* | 62 |
| Medtr5g081810.1 | *Medicago truncatula* | 63 |
| PGSC0003DMT400049383 | *Trametes versicolor* | 64 |
| AT2G38080 | *Arabidopsis thaliana* | 65 |
| LOC_Os11g48060.1 | *Oryza sativa* | 66 |
| GRMZM2G072808_T01 | *Zea mays* | 67 |

What is claimed is:

1. A genetically modified plant characterized by a reduced expression of the LAC2 gene as compared to a control plant, wherein the genetic modification is specifically targeted at the LAC2 gene or the LAC2 mRNA to reduce the LAC2 gene expression.

2. The genetically modified plant of claim 1, wherein said genetically modified plant belongs to a genus selected from the group consisting of *Populus, Manihot, Gossypium, Eucalyptus, Medicago, Arabidopsis, Solanum, Oryza* and *Zea*.

3. The genetically modified plant of claim 2, wherein the plant is selected from the group consisting of *Populus balsamifera, Populus deltoides, Populus trichocarpa, Populus tremuloides, Populus tremula, Populus alba* and *Populus maximowiczii*.

4. The genetically modified plant of claim 1, wherein the reduced expression of the LAC2 gene is achieved by a method selected from the group consisting of introducing a nucleic acid inhibitor, the CRISPR/Cas system, the Cre/Lox system, the TALEN system, and homologous recombination.

5. The genetically modified plant of claim 4, wherein said nucleic acid inhibitor is selected from the group consisting of an antisense RNA, a small interfering RNA, an RNAi microRNA, an artificial microRNA, and a ribozyme.

6. A method for biofuel production, comprising using the plant of claim 1 in a biofuel fermentation process.

7. An expression vector, comprising a nucleotide sequence that is transcribed into a nucleic acid inhibitor of expression of the LAC2 gene, operably linked to a regulatory region that is functional in a plant, wherein the nucleic acid is selected from the group consisting of an antisense RNA, a small interfering RNA, an RNAi microRNA, an artificial microRNA, and a ribozyme.

8. The expression vector of claim 7, wherein the regulatory region comprises an inducible promoter or a tissue-specific promoter.

9. The expression vector of claim 8 wherein the tissue-specific promoter is a xylem-specific promoter.

10. A method for increasing glucose and/or xylose release in a plant or plant cell, comprising introducing the expression vector of claim 7 in said plant or plant cell, and expressing the nucleic acid in plant or plant cell.

11. A plant or plant cell comprising the expression vector of claim 7.

* * * * *